United States Patent
Stoeckius

(10) Patent No.: US 12,405,264 B2
(45) Date of Patent: Sep. 2, 2025

(54) ELECTROPHORETIC SYSTEM AND METHOD FOR ANALYTE CAPTURE

(71) Applicant: 10x Genomics, Inc., Pleasanton, CA (US)

(72) Inventor: Marlon Stoeckius, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/150,997

(22) Filed: Jan. 15, 2021

(65) Prior Publication Data

US 2021/0223227 A1    Jul. 22, 2021

Related U.S. Application Data

(60) Provisional application No. 62/962,559, filed on Jan. 17, 2020.

(51) Int. Cl.
  G01N 33/487   (2006.01)
  B01L 3/00     (2006.01)
  G01N 27/447   (2006.01)

(52) U.S. Cl.
  CPC ...... *G01N 33/48721* (2013.01); *B01L 3/5025* (2013.01); *G01N 27/44791* (2013.01); *B01L 2400/0421* (2013.01)

(58) Field of Classification Search
  CPC .. B01L 2400/0421; B01L 3/5025; B01L 9/52; B01L 3/508; B01L 3/50851; B01L 3/50853; B01L 2300/047; B01L 2300/0809; B01L 2300/0829; B01L 2200/0689; B01L 2300/043; B01L 2300/048; B01L 2300/0618; B01L 2300/0822; B01L 2300/0858; B01L 2300/123; B01L 3/5085;
(Continued)

(56) References Cited

U.S. PATENT DOCUMENTS 4,557,903 A    12/1985  McCormick
4,574,729 A     3/1986  Wells
(Continued)

FOREIGN PATENT DOCUMENTS

AU    2003200718    10/2006
CA    3054046        3/2020
(Continued)

OTHER PUBLICATIONS

Bibikova et al., "Quantitative gene expression profiling in formalin-fixed paraffin-embedded tissues using universal bead arrays," The American Journal of Pathology, Nov. 1, 2004, 165(5):1799-1807.
(Continued)

*Primary Examiner* — Christopher L Chin
*Assistant Examiner* — Ellis Follett Lusi
(74) *Attorney, Agent, or Firm* — Fish & Richardson P.C.

(57) ABSTRACT

An electrophoretic system is provided for analyte capture from a biological sample. The electrophoretic system can be used to permeabilize the sample to allow analytes to be released from the sample. For example, the sample can be contacted with capture probes attached to a substrate, and an electric field created by the electrophoretic system can cause analytes to be released from the cell, and effectively migrate toward and bind to the capture probes attached to the substrate.

20 Claims, 29 Drawing Sheets

FIG. 3A

(58) Field of Classification Search
CPC ....... G01N 27/44791; G01N 33/48721; G01N 27/447; G01N 27/44786; C12M 23/12; C12M 1/05; B65D 5/643
USPC ....... 435/971, 204, 205, 40, 287.9, 2, 287.1, 435/287.2, 288.3, 288.4, 7.1; 436/7, 775, 436/151, 205, 501, 516; 204/450, 451, 204/452

See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,061,049 A | 10/1991 | Hornbeck |
| 5,130,238 A | 7/1992 | Malek |
| 5,183,053 A | 2/1993 | Ych et al. |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,559,032 A | 9/1996 | Pomeroy |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,716,825 A | 2/1998 | Hancock et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,962,271 A | 10/1999 | Chenchik et al. |
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,083,761 A | 7/2000 | Kedar et al. |
| 6,130,073 A | 10/2000 | Eggerding |
| 6,136,592 A | 10/2000 | Leighton |
| 6,143,496 A | 11/2000 | Brown |
| 6,153,389 A | 11/2000 | Haarer |
| 6,157,432 A | 12/2000 | Helbing |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,221,654 B1 | 4/2001 | Quake |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,337,472 B1 | 1/2002 | Garner et al. |
| 6,344,316 B1 | 2/2002 | Lockhart |
| 6,344,329 B1 | 2/2002 | Lizardi et al. |
| 6,348,990 B1 | 2/2002 | Igasaki et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,485,982 B1 | 11/2002 | Charlton |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,565,727 B1 | 5/2003 | Shenderov |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,673,620 B1 | 1/2004 | Loeffler |
| 6,737,236 B1 | 5/2004 | Pieken et al. |
| 6,770,441 B2 | 8/2004 | Dickinson |
| 6,773,566 B2 | 8/2004 | Shenderov |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,911,132 B2 | 6/2005 | Pamula |
| 6,911,345 B2 | 6/2005 | Quake |
| 6,913,881 B1 | 7/2005 | Aizenstein et al. |
| 6,913,921 B2 | 7/2005 | Fischer |
| 6,942,968 B1 | 9/2005 | Dickinson et al. |
| 6,969,488 B2 | 11/2005 | Bridgham |
| 6,977,033 B2 | 12/2005 | Becker |
| 7,001,792 B2 | 2/2006 | Sauer et al. |
| 7,011,944 B2 | 3/2006 | Prudent et al. |
| 7,052,244 B2 | 5/2006 | Fouillet |
| 7,057,026 B2 | 6/2006 | Barnes |
| 7,083,980 B2 | 8/2006 | Reznikoff et al. |
| 7,098,041 B2 | 8/2006 | Kaylor et al. |
| 7,115,400 B1 | 10/2006 | Adessi |
| 7,118,883 B2 | 10/2006 | Inoue |
| 7,163,612 B2 | 1/2007 | Sterling |
| 7,166,431 B2 | 1/2007 | Chee et al. |
| 7,192,735 B2 | 3/2007 | Lambalot |
| 7,211,414 B2 | 5/2007 | Hardin |
| 7,223,371 B2 | 5/2007 | Hayenga et al. |
| 7,244,559 B2 | 7/2007 | Rothberg |
| 7,255,994 B2 | 8/2007 | Lao |
| 7,258,976 B2 | 8/2007 | Mitsubashi |
| 7,264,929 B2 | 9/2007 | Rothberg |
| 7,282,328 B2 | 10/2007 | Kong et al. |
| 7,297,518 B2 | 11/2007 | Quake |
| 7,328,979 B2 | 2/2008 | Decre |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,456,012 B2 | 11/2008 | Ryttsen et al. |
| 7,462,449 B2 | 12/2008 | Quake |
| 7,473,767 B2 | 1/2009 | Dimitrov |

(56) References Cited

U.S. PATENT DOCUMENTS

| | | |
|---|---|---|
| 7,499,806 B2 | 3/2009 | Kermani et al. |
| 7,501,245 B2 | 3/2009 | Quake |
| 7,537,897 B2 | 5/2009 | Brenner |
| 7,547,380 B2 | 6/2009 | Velev |
| 7,561,336 B2 | 7/2009 | Osaka et al. |
| 7,563,576 B2 | 7/2009 | Chee |
| 7,579,153 B2 | 8/2009 | Brenner |
| 7,582,420 B2 | 9/2009 | Oliphant et al. |
| 7,595,883 B1 | 9/2009 | El Gamal |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,641,779 B2 | 1/2010 | Becker |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,785,869 B2 | 8/2010 | Belgrader et al. |
| 7,803,943 B2 | 9/2010 | Mao |
| 7,858,321 B2 | 12/2010 | Glezer et al. |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,278,034 B2 | 10/2012 | Muraca |
| 8,288,103 B2 | 10/2012 | Oliphant |
| 8,288,122 B2 | 10/2012 | O'Leary et al. |
| 8,330,087 B2 | 12/2012 | Domenicali |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,637,242 B2 | 1/2014 | Shen |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,778,849 B2 | 7/2014 | Bowen |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,900,529 B2 | 12/2014 | Shaikh et al. |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,951,781 B2 | 2/2015 | Reed |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,557,330 B2 | 1/2017 | Siciliano |
| 9,574,230 B2 | 2/2017 | Van Eijk |
| 9,582,877 B2 | 2/2017 | Fu |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,799,992 B2 | 10/2017 | Hirose et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 9,975,122 B2 | 5/2018 | Masquelier et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,032,064 B2 | 7/2018 | Hoyt |
| 10,035,992 B2 | 7/2018 | Gloeckner et al. |
| 10,041,949 B2 | 8/2018 | Bendall et al. |
| 10,053,723 B2 | 8/2018 | Hindson et al. |
| 10,059,989 B2 | 8/2018 | Giresi et al. |
| 10,059,990 B2 | 8/2018 | Boyden et al. |
| 10,071,377 B2 | 9/2018 | Bharadwaj et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |

(56) References Cited

U.S. PATENT DOCUMENTS

| | | |
|---|---|---|
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,662,468 B2 | 5/2020 | Chee |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,214,796 B2 | 1/2022 | Shirai et al. |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 12,128,403 B2 | 10/2024 | Kim et al. |
| 12,129,516 B2 | 10/2024 | Tentori et al. |
| 12,157,124 B2 | 12/2024 | Cox et al. |
| 12,180,543 B2 | 12/2024 | Uytingco et al. |
| 12,195,790 B2 | 1/2025 | Sukovich et al. |
| 12,203,134 B2 | 1/2025 | Nagendran et al. |
| 12,209,280 B1 | 1/2025 | Mignardi et al. |
| D1,064,308 S | 2/2025 | Alimsijah et al. |
| 12,223,751 B2 | 2/2025 | Li et al. |
| 12,228,544 B2 | 2/2025 | Kim et al. |

(56) References Cited

U.S. PATENT DOCUMENTS

| | | |
|---|---|---|
| 12,234,505 B2 | 2/2025 | Chee |
| 12,241,060 B2 | 3/2025 | Kim et al. |
| 12,241,890 B2 | 3/2025 | Delaney et al. |
| 12,249,085 B2 | 3/2025 | Tentori et al. |
| 12,265,079 B1 | 4/2025 | Bent |
| 12,270,077 B2 | 4/2025 | Schnall-Levin et al. |
| 12,275,988 B2 | 4/2025 | Galonska et al. |
| 12,281,357 B1 | 4/2025 | Tentori et al. |
| 12,286,673 B2 | 4/2025 | Bava |
| 12,287,264 B2 | 4/2025 | Cox et al. |
| 12,297,486 B2 | 5/2025 | Patterson et al. |
| 12,297,487 B2 | 5/2025 | Chee |
| 12,297,488 B2 | 5/2025 | Chee |
| 2001/0055764 A1 | 12/2001 | Empendocles et al. |
| 2002/0022261 A1 | 2/2002 | Anderson et al. |
| 2002/0040275 A1 | 4/2002 | Cravatt |
| 2002/0045272 A1 | 4/2002 | McDevitt et al. |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0150909 A1 | 10/2002 | Stuelpnagel |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0092624 A1 | 5/2003 | Wang et al. |
| 2003/0113713 A1 | 6/2003 | Glezer |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0175947 A1 | 9/2003 | Liu et al. |
| 2003/0190744 A1 | 10/2003 | McGarry et al. |
| 2003/0205632 A1 | 11/2003 | Kim et al. |
| 2003/0211489 A1 | 11/2003 | Shen et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0050699 A1 | 3/2004 | Goncalves |
| 2004/0067492 A1 | 4/2004 | Peng et al. |
| 2004/0082058 A1 | 4/2004 | Schleifer et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0121456 A1 | 6/2004 | Fischer |
| 2004/0219588 A1 | 11/2004 | Furuta |
| 2004/0235103 A1 | 11/2004 | Reznikoff et al. |
| 2004/0241660 A1 | 12/2004 | Wojtowicz et al. |
| 2004/0248287 A1 | 12/2004 | Hu et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima |
| 2005/0106617 A1 | 5/2005 | Besemer et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0226780 A1 | 10/2005 | Sandell et al. |
| 2005/0227271 A1 | 10/2005 | Kwon |
| 2005/0239119 A1 | 10/2005 | Tsukada et al. |
| 2005/0239192 A1 | 10/2005 | Nasarabadi et al. |
| 2005/0260653 A1 | 11/2005 | LaBaer |
| 2005/0266417 A1 | 12/2005 | Barany et al. |
| 2006/0039823 A1 | 2/2006 | Yamakawa et al. |
| 2006/0041385 A1 | 2/2006 | Bauer et al. |
| 2006/0046313 A1 | 3/2006 | Roth |
| 2006/0063160 A1 | 3/2006 | West et al. |
| 2006/0084078 A1 | 4/2006 | Zhao |
| 2006/0105352 A1 | 5/2006 | Qiao et al. |
| 2006/0127946 A1 | 6/2006 | Montagu et al. |
| 2006/0134669 A1 | 6/2006 | Casasanta |
| 2006/0154286 A1 | 7/2006 | Kong et al. |
| 2006/0164490 A1 | 7/2006 | Kim et al. |
| 2006/0180489 A1 | 8/2006 | Guiney et al. |
| 2006/0188901 A1 | 8/2006 | Barnes et al. |
| 2006/0194331 A1 | 8/2006 | Pamula et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0023292 A1 | 2/2007 | Kim et al. |
| 2007/0026430 A1 | 2/2007 | Andersen et al. |
| 2007/0036511 A1 | 2/2007 | Lundquist et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0116612 A1 | 5/2007 | Williamson |
| 2007/0128071 A1 | 6/2007 | Shea et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0166725 A1 | 7/2007 | McBride et al. |
| 2007/0172873 A1 | 7/2007 | Brenner et al. |
| 2007/0184456 A1 | 8/2007 | Chee et al. |
| 2007/0207482 A1 | 9/2007 | Church et al. |
| 2007/0215466 A1 | 9/2007 | Okada |
| 2007/0243634 A1 | 10/2007 | Pamula et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009071 A1 | 1/2008 | Sogard |
| 2008/0009420 A1 | 1/2008 | Schroth et al. |
| 2008/0043235 A1 | 2/2008 | Oldham et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0218838 A1 | 9/2008 | Rey-Mermet |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0011943 A1 | 1/2009 | Drmanac et al. |
| 2009/0018024 A1 | 1/2009 | Church et al. |
| 2009/0023148 A1* | 1/2009 | Moyle ............... B01L 3/50851 435/7.1 |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0169089 A1 | 7/2009 | Hunt et al. |
| 2009/0170713 A1 | 7/2009 | van Eijk et al. |
| 2009/0192044 A1 | 7/2009 | Fouillet |
| 2009/0197326 A1 | 8/2009 | El Gamal et al. |
| 2009/0202998 A1 | 8/2009 | Schlumpberger et al. |
| 2009/0233802 A1 | 9/2009 | Bignell et al. |

(56) References Cited

U.S. PATENT DOCUMENTS

| | | |
|---|---|---|
| 2009/0239232 A1 | 9/2009 | Kurn |
| 2009/0253163 A1 | 10/2009 | Xie et al. |
| 2009/0253581 A1 | 10/2009 | van Eijk et al. |
| 2009/0253582 A1* | 10/2009 | Pena .................. B29C 45/1676 506/7 |
| 2009/0270273 A1 | 10/2009 | Burns et al. |
| 2009/0283407 A1 | 11/2009 | Van Eijk |
| 2009/0286249 A1 | 11/2009 | Bekcer et al. |
| 2009/0291854 A1 | 11/2009 | Weisinger-Mayr et al. |
| 2009/0312193 A1 | 12/2009 | Kim et al. |
| 2009/0321262 A1 | 12/2009 | Adachi et al. |
| 2010/0009871 A1 | 1/2010 | Reed et al. |
| 2010/0031757 A1 | 2/2010 | Hoyer |
| 2010/0035249 A1 | 2/2010 | Hayashizaki et al. |
| 2010/0069263 A1 | 3/2010 | Shendure et al. |
| 2010/0096266 A1 | 4/2010 | Kim et al. |
| 2010/0105052 A1 | 4/2010 | Drmanac et al. |
| 2010/0111768 A1 | 5/2010 | Banerjee et al. |
| 2010/0120097 A1 | 5/2010 | Matz et al. |
| 2010/0120098 A1 | 5/2010 | Grunenwald et al. |
| 2010/0126862 A1 | 5/2010 | Sabin et al. |
| 2010/0129874 A1 | 5/2010 | Mitra |
| 2010/0145037 A1 | 6/2010 | Brive et al. |
| 2010/0151511 A1 | 6/2010 | Gereenizer et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0267590 A1 | 10/2010 | Grudzien et al. |
| 2010/0273219 A1 | 10/2010 | May et al. |
| 2010/0273679 A1 | 10/2010 | Cuppoletti et al. |
| 2010/0282617 A1 | 11/2010 | Rothberg et al. |
| 2011/0028685 A1 | 2/2011 | Purkayastha |
| 2011/0033854 A1 | 2/2011 | Drmanac et al. |
| 2011/0045462 A1 | 2/2011 | Fu et al. |
| 2011/0048951 A1 | 3/2011 | Wu |
| 2011/0059436 A1 | 3/2011 | Hardin et al. |
| 2011/0090563 A1 | 4/2011 | Krasov |
| 2011/0111409 A1 | 5/2011 | Sinicropi et al. |
| 2011/0152111 A1 | 6/2011 | Illumina |
| 2011/0177518 A1 | 7/2011 | Kartalov et al. |
| 2011/0244448 A1 | 10/2011 | Shirai et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | Van Eijk et al. |
| 2012/0160683 A1 | 6/2012 | Ye et al. |
| 2012/0177543 A1 | 7/2012 | Battrell |
| 2012/0195810 A1 | 8/2012 | Coben et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0270305 A1 | 10/2012 | Reed et al. |
| 2012/0279954 A1 | 11/2012 | Ceremony et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0053273 A1 | 2/2013 | Juncker et al. |
| 2013/0065768 A1 | 3/2013 | Zheng et al. |
| 2013/0065788 A1 | 3/2013 | Glezer et al. |
| 2013/0079232 A1 | 3/2013 | Kain et al. |
| 2013/0146459 A1 | 6/2013 | Bazant et al. |
| 2013/0171621 A1 | 7/2013 | Luo et al. |
| 2013/0203100 A1 | 8/2013 | Otter et al. |
| 2013/0244884 A1 | 9/2013 | Jacobson et al. |
| 2013/0252847 A1 | 9/2013 | McKenna et al. |
| 2013/0260372 A1 | 10/2013 | Buermann et al. |
| 2013/0261019 A1 | 10/2013 | Lin et al. |
| 2013/0296174 A1 | 11/2013 | Peumans |
| 2013/0302801 A1 | 11/2013 | Asbury et al. |
| 2013/0338042 A1 | 12/2013 | Shen et al. |
| 2014/0011707 A1 | 1/2014 | Ye et al. |
| 2014/0066318 A1 | 3/2014 | Frisen et al. |
| 2014/0121118 A1 | 5/2014 | Warner |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0298091 A1 | 10/2015 | Weitz et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0033496 A1 | 2/2016 | Chou et al. |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0298180 A1 | 10/2016 | Chee |
| 2016/0299165 A1 | 10/2016 | Zhou |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0159109 A1 | 6/2017 | Zheng et al. |
| 2017/0166962 A1 | 6/2017 | van Eijk et al. |
| 2017/0220733 A1 | 8/2017 | Zhuang |
| 2017/0233722 A1 | 8/2017 | Scelig et al. |
| 2017/0241911 A1 | 8/2017 | Rockel et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0052082 A1 | 2/2018 | Groll et al. |
| 2018/0057873 A1 | 3/2018 | Zhou et al. |
| 2018/0074039 A1 | 3/2018 | Soper et al. |
| 2018/0080019 A1 | 3/2018 | Blainey et al. |
| 2018/0080876 A1 | 3/2018 | Rockel et al. |
| 2018/0088112 A1 | 3/2018 | Fan et al. |
| 2018/0094316 A1 | 4/2018 | Oliphant et al. |
| 2018/0095067 A1 | 4/2018 | Huff et al. |
| 2018/0104694 A1 | 4/2018 | Huff et al. |
| 2018/0104964 A1 | 4/2018 | Uemura et al. |
| 2018/0112248 A1 | 4/2018 | Lam et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |

(56) References Cited

U.S. PATENT DOCUMENTS

| | | |
|---|---|---|
| 2018/0217094 A1 | 8/2018 | Herr et al. |
| 2018/0237864 A1 | 8/2018 | Imler et al. |
| 2018/0245142 A1* | 8/2018 | So ..................... C12Q 1/6816 |
| 2018/0247017 A1 | 8/2018 | van Eijk et al. |
| 2018/0251833 A1 | 9/2018 | Daugharthy et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0099754 A1 | 4/2019 | Dupouy et al. |
| 2019/0113532 A1 | 4/2019 | Tan et al. |
| 2019/0119735 A1 | 4/2019 | Deisseroth et al. |
| 2019/0126280 A1 | 5/2019 | Gach et al. |
| 2019/0135774 A1 | 5/2019 | Orbai |
| 2019/0145982 A1 | 5/2019 | Chee et al. |
| 2019/0155835 A1 | 5/2019 | Daugharthy et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0201891 A1 | 7/2019 | Pallas et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0049599 A1 | 2/2020 | Alexander et al. |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0298241 A1 | 9/2020 | Kabaha et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0393343 A1 | 12/2020 | Kennedy-Darling et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava et al. |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |

(56) References Cited

U.S. PATENT DOCUMENTS

| | | |
|---|---|---|
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0031305 A1 | 2/2023 | Hernandez Neuta et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183684 A1 | 6/2023 | Gallant et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0212650 A1 | 7/2023 | Chew et al. |
| 2023/0212655 A1 | 7/2023 | Chee |
| 2023/0212656 A1 | 7/2023 | Chow et al. |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416807 A1 | 12/2023 | Chee |
| 2023/0416808 A1 | 12/2023 | Sukovich et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |

(56) References Cited

U.S. PATENT DOCUMENTS

2024/0253036 A1 8/2024 Kim et al.
2024/0263218 A1 8/2024 Katiraee et al.
2024/0271190 A1 8/2024 Stoeckius et al.
2024/0271195 A1 8/2024 Mikhaiel et al.
2024/0279747 A1 8/2024 Williams
2024/0287600 A1 8/2024 Iyer et al.
2024/0294971 A1 9/2024 Galonska
2024/0294974 A1 9/2024 Galonska et al.
2024/0294975 A1 9/2024 Lin et al.
2024/0301488 A1 9/2024 Stoeckius
2024/0301489 A1 9/2024 Chew et al.
2024/0360494 A1 10/2024 Costa et al.
2024/0368711 A1 11/2024 Giacomello et al.
2024/0377297 A1 11/2024 Cox et al.
2024/0385088 A1 11/2024 Kim et al.
2024/0392349 A1 11/2024 Frisen et al.
2024/0392351 A1 11/2024 Chee
2024/0392352 A1 11/2024 Stahl et al.
2024/0392353 A1 11/2024 Engblom et al.
2024/0401109 A1 12/2024 Kim et al.
2024/0401117 A1 12/2024 Bava
2024/0401118 A1 12/2024 Tentori et al.
2024/0404301 A1 12/2024 Li et al.
2024/0408593 A1 12/2024 Kim et al.
2024/0416315 A1 12/2024 Bava
2024/0417783 A1 12/2024 Chew et al.
2024/0417784 A1 12/2024 Sukovich et al.
2025/0002980 A1 1/2025 Tentori et al.
2025/0002982 A1 1/2025 Stoeckius et al.
2025/0003956 A1 1/2025 Delaney et al.
2025/0019689 A1 1/2025 Galonska et al.
2025/0019749 A1 1/2025 Katiraee et al.
2025/0066762 A1 2/2025 Man et al.
2025/0066770 A1 2/2025 Costa
2025/0073719 A1 3/2025 Cox et al.
2025/0075261 A1 3/2025 Kim
2025/0101501 A1 3/2025 Chee
2025/0101502 A1 3/2025 Chee
2025/0101504 A1 3/2025 Nagendran et al.
2025/0122564 A1 4/2025 Mignardi et al.
2025/0122565 A1 4/2025 Schnall-Levin et al.
2025/0129412 A1 4/2025 Uytingco et al.
2025/0129421 A1 4/2025 Schnall-Levin et al.
2025/0137043 A1 5/2025 Tentori
2025/0146057 A1 5/2025 Schnall-Levin et al.
2025/0146071 A1 5/2025 Schnall-Levin et al.
2025/0146072 A1 5/2025 Schnall-Levin et al.
2025/0154565 A1 5/2025 Chee
2025/0154566 A1 5/2025 Chee
2025/0154567 A1 5/2025 Chee
2025/0154568 A1 5/2025 Friscn et al.
2025/0154569 A1 5/2025 Stoeckius et al.
2025/0154571 A1 5/2025 Ramachandran Iyer et al.
2025/0154588 A1 5/2025 Ramachandran Iyer et al.
2025/0155446 A1 5/2025 Uytingco et al.

FOREIGN PATENT DOCUMENTS

| | | |
|---|---|---|
| CN | 1273609 | 11/2000 |
| CN | 1425133 | 6/2003 |
| CN | 1537953 | 10/2004 |
| CN | 1680604 | 10/2005 |
| CN | 1749752 | 3/2006 |
| CN | 1898398 | 1/2007 |
| CN | 1981188 | 6/2007 |
| CN | 101142325 | 3/2008 |
| CN | 101221182 | 7/2008 |
| CN | 101522915 | 9/2009 |
| CN | 202548048 | 11/2012 |
| CN | 102851369 | 1/2013 |
| CN | 104513785 | 4/2015 |
| CN | 107849606 | 3/2018 |
| CN | 108949924 | 12/2018 |
| EP | 0961110 | 12/1999 |
| EP | 1782737 | 5/2007 |
| EP | 1878502 | 1/2008 |
| EP | 1910562 | 4/2008 |
| EP | 1923471 | 5/2008 |
| EP | 2002017 | 12/2008 |
| EP | 2130913 | 12/2009 |
| EP | 2292788 | 3/2011 |
| EP | 2302070 | 3/2011 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1999/063385 | 12/1999 |
| WO | WO 2000/17390 | 3/2000 |
| WO | WO 2001/06012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2003/106973 | 12/2003 |
| WO | WO 2004/015080 | 2/2004 |
| WO | WO 2004/028955 | 4/2004 |
| WO | WO 2004/067759 | 8/2004 |
| WO | WO 2004/081225 | 9/2004 |
| WO | WO 2004/108268 | 12/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/056861 | 6/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/120241 | 10/2007 |
| WO | WO 2007/123744 | 11/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/157801 | 12/2008 |
| WO | WO 2009/032167 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2011/102903 | 8/2011 |
| WO | WO 2012/049316 | 4/2012 |
| WO | WO 2012/058096 | 5/2012 |

(56) References Cited

FOREIGN PATENT DOCUMENTS

| | | |
|---|---|---|
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2012/168003 | 12/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/128129 | 8/2014 |
| WO | WO 2014/130576 | 8/2014 |
| WO | WO 2014/142841 | 9/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/048871 | 3/2017 |
| WO | WO 2017/075293 | 5/2017 |
| WO | WO 2017/112957 | 6/2017 |
| WO | WO 2017/096158 | 7/2017 |
| WO | WO 2017/143155 | 8/2017 |
| WO | WO 2017/144338 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/075436 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/148471 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/104337 | 5/2019 |
| WO | WO 2019/113457 | 6/2019 |
| WO | WO 2019/126313 | 6/2019 |
| WO | WO 2019/140201 | 7/2019 |
| WO | WO 2019/140334 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/051152 | 3/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/098810 | 5/2022 |
| WO | WO 2022/099037 | 5/2022 |
| WO | WO 2022/103712 | 5/2022 |
| WO | WO 2022/109181 | 5/2022 |
| WO | WO 2011/019964 | 6/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |

(56) References Cited

FOREIGN PATENT DOCUMENTS

| | | |
|---|---|---|
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/015913 | 11/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |

OTHER PUBLICATIONS

Choi et al., "Multiplexed detection of mRNA using porosity-tuned hydrogel microparticles," Analytical chemistry, Sep. 28, 2012, 84(21):9370-9378.

Fan et al., "A versatile assay for high-throughput gene expression profiling on universal array matrices," Genome Research, May 1, 2004, 14(5):878-885.

Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.

Kim, "Development of Microdevices for Applications to Bioanalysis," Dissertation for the degree of Doctor of Philosophy, University of Texas at Austin, Aug. 2007, 176 pages.

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Boulé et al., "Terminal deoxynucleotidyl transferase indiscriminately incorporates ribonucleotides and deoxyribonucleotides," J Biol Chem., Aug. 2001, 276(33):31388-93.

Burgess, "Spatial transcriptomics coming of age," Nat Rev Genet., Jun. 2019, 20(6):317, 1 page.

Caliari et al., "A practical guide to hydrogels for cell culture," Nat Methods., Apr. 2016, 13(5):405-14.

Evers et al., "The effect of formaldehyde fixation on RNA: optimization of formaldehyde adduct removal," J Mol Diagn., May 2011, 13(3):282-8.

Gansauge et al., "Single-stranded DNA library preparation from highly degraded DNA using T4 DNA ligase, " Nucleic Acids Res., Jun. 2017, 45(10):e79, 10 pages.

Hafner et al., "Identification of microRNAs and other small regulatory RNAs using cDNA library sequencing," Methods, Jan. 2008, 44(1):3-12.

Hanauer et al., "Separation of nanoparticles by gel electrophoresis according to size and shape," Nano Lett., Sep. 2007, 7(9):2881-5.

Hattersley et al., "Development of a microfluidic device for the maintenance and interrogation of viable tissue biopsies," Lab Chip., Nov. 2008, 8(11):1842-6.

Ho et al., "Characterization of an ATP-Dependent DNA Ligase Encoded by Chlorella Virus PBCV-1," Journal of Virology, Mar. 1997, 71(3):1931-1937.

Hsuih et al., "Novel, Ligation-Dependent PCR Assay for Detection of Hepatitis C Virus in Serum," Journal of Clinical Microbiology, Mar. 1996, 34(3):501-507.

Kumar et al., "Template-directed oligonucleotide strand ligation, covalent intramolecular DNA circularization and catenation using click chemistry," J Am Chem Soc., May 2007, 129(21):6859-64.

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ozsolak et al., "Digital transcriptome profiling from attomole-level RNA samples," Genome Res., Apr. 2010, 20(4):519-25.

Slomovic et al., "Addition of poly(A) and poly(A)-rich tails during RNA degradation in the cytoplasm of human cells," Proc Natl Acad Sci USA, Apr. 2010, 107(16):7407-12.

Taylor et al., "Microfluidic local perfusion chambers for the visualization and manipulation of synapses, " Neuron., Apr. 2010, 66(1):57-68, 25 pages.

Thomas et al., "A chamber for the perfusion of in vitro tissue with multiple solutions," J. Neurophysiol., Jul. 2013, 110:269-277.

Toy et al., "A Simple Plastic Perfusion Chamber for Continuous Maintenance and Cinematography of Tissue Cultures," Experimental Cell Research, 1958, 14:97-103.

Ulery et al., "Biomedical Applications of Biodegradable Polymers," J Polym Sci B Polym Phys., Jun. 2011, 49(12):832-864.

Vandenbroucke et al., "Quantification of splice variants using real-time PCR," Nucleic Acids Research, 2001, 29(13):e68, 7 pages.

Zhang et al., "Genome-wide open chromatin regions and their effects on the regulation of silk protein genes in Bombyx mori," Sci Rep., Oct. 2017, 7(1):12919, 9 pages.

U.S. Appl. No. 63/033,348, filed Jun. 2, 2020, Bent.

Arslan et al., "Engineering of a superhelicase through conformational control (Supplementary Materials), " Science, Apr. 17, 2015, 348(6232):344-347, 18 pages.

Arslan et al., "Engineering of a superhelicase through conformational control," Science, Apr. 17, 2015, 348(6232):344-347.

Baner et al., "Signal amplification of padlock probes by rolling circle replication," Nucleic Acids Res., 1998, 26(22):5073-5078.

(56) References Cited

OTHER PUBLICATIONS

Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Efficient in situ barcode sequencing using padlock probe-based BaristaSeq," Nucleic Acids Res., 2018, 46(4): e22, 11 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Codeluppi et al., "Spatial organization of the somatosensory cortex revealed by osmFISH," Nature Methods, Nov. 2018, 15:932-935.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Faruqi et al., "High-throughput genotyping of single nucleotide polymorphisms with rolling circle amplification," BMC Genomics, Aug. 2001, 2:4, 10 pages.
Gao et al., "A highly homogeneous expansion microscopy polymer composed of tetrahedron-like monomers, " bioRxiv, Oct. 22, 2019, 23 pages (Preprint).
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Goh et al., "Highly Specific Multiplexed RNA Imaging In Tissues With Split-FISH," Nat Methods, Jun. 15, 2020, 17(7):689-693, 21 pages.
Goransson et al., "A single molecule array for digital targeted molecular analyses," Nucleic Acids Res., Nov. 25, 2009, 37(1):e7, 9 pages.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Mignardi et al., "Oligonucleotide gap-fill ligation for mutation detection and sequencing in situ," Nucleic Acids Research, Aug. 3, 2015, 43(22):e151, 12 pages.
Mohsen et al., "The Discovery of Rolling Circle Amplification and Rolling Circle Transcription," Acc Chem Res., Nov. 15, 2016, 49(11):2540-2550, 25 pages.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Takei et al., "Integrated Spatial Genomics Reveals Global Architecture Of Single Nuclei," Nature, Jan. 27, 2021, 590(7845):344-350, 53 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.

Mulder et al., "CapTCR-seq: hybrid capture for T-cell receptor repertoire profiling," Blood Advances, Dec. 2018, 2(23):3506-3514.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Chen et al. "Arrayed profiling of multiple glycans on whole living cell surfaces." Analytical chemistry, Oct. 15, 2013, 85(22):11153-11158.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Eastburn, "Microfluidic droplet enrichment for targeted sequencing," Nucleic Acids Research, 2015, 43(13):1-8.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Hobro et al., "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Schmidl et al., "ChIPmentation: fast, robust, low-input ChIP-seq for histones and transcription factors," Nature Methods, Oct. 2015, 12:963-965.
Su et al., "Restriction enzyme selection dictates detection range sensitivity in chromatin conformation capture-based variant-to-gene mapping approaches, " bioRxiv, Dec. 15, 2020, 22 pages.
10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
Kuhn et al., "A novel, high-performance random array platform for quantitative gene expression profiling," Genome Res, 2004, 14:2347-2356.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
Asp et al., "A spatiotemporal organ-wide gene expression and cell atlas of the developing human heart," Cell, Dec. 12, 2019, 179(7):1647-1660.

(56) References Cited

OTHER PUBLICATIONS

Nelson, "The Most Popular Cutting Styles of Gaskets & Their Advantages," Grand River Rubber & Plastics Blog, Feb. 18, 2020, retrieved on Dec. 3, 2024, retreived from URL <https://www.info.grrp.com/blog/the-most-popular-cutting-styles-of-gaskets-their-advantages>, 4 pages.

Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.

10xGenomics.com [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a7256eeb96bc294967/CG00238_VisiumSpatialTissueOptimizationUserGuide_Rev_A.pdf>, 46 pages.

Barnett et al., "ATAC-Me Captures Prolonged DNA Methylation of Dynamic Chromatin Accessibility Loci during Cell Fate Transitions, " Mol Cell., Mar. 2020, 77(6):1350-1364.e6.

Cruz et al., "Methylation in cell-free DNA for early cancer detection," Ann Oncol., Jun. 2018, 29(6):1351-1353.

Hamaguchi et al., "Direct reverse transcription-PCR on oligo(dr)-immobilized polypropylene microplates after capturing total mRNA from crude cell lysates," Clin Chem., Nov. 1998, 44(11):2256-63.

Ke et al., "In situ sequencing for RNA analysis in preserved tissue and cells," Nat Methods., Sep. 2013, Supplementary Materials, 29 pages.

Miner et al., "Molecular barcodes detect redundancy and contamination in hairpin-bisulfite PCR," Nucleic Acids Res., Sep. 2004, 32(17):e135, 4 pages.

Wang et al., "Tagmentation-based whole-genome bisulfite sequencing, " Nature Protocols, Oct. 2013, 8(10):2022-2032.

Dalma-Weiszhausz et al., "The affymetrix GencChip platform: an overview," Methods Enzymol., 2006, 410:3-28.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Lahiani et al., "Enabling Histopathological Annotations on Immunofluorescent Images through Virtualization of Hematoxylin and Eosin," J Pathol Inform., Feb. 2018, 9:1, 8 pages.

Lou et al., "A review of room temperature storage of biospecimen tissue and nucleic acids for anatomic pathology laboratories and biorepositories," Clin Biochem., Mar. 2014, 47(4-5):267-73.

Lykidis et al., "Novel zinc-based fixative for high quality DNA, RNA and protein analysis," Nucleic Acids Res., Jun. 2007, 35(12):e85, 10 pages.

Miller et al., "Chapter 11—Solid and Suspension Microarrays for Microbial Diagnostics, " Methods in Microbiology, 2015, 42:395-431.

Nadji et al., "Immunohistochemistry of tissue prepared by a molecular-friendly fixation and processing system, " Appl Immunohistochem Mol Morphol., Sep. 2005, 13(3):277-82.

Passow et al., "RNAlater and flash freezing storage methods nonrandomly influence observed gene expression in RNAseq experiments, " bioRxiv, Jul. 2018, 28 pages.

Porreca et al., "Polony DNA sequencing," Curr Protoc Mol Biol., Nov. 2006, Chapter 7, Unit 7.8, pp. 7.8.1-7.8.22.

Vickovic et al., "SM-Omics: An automated Platform for High-Throughput Spatial Multi-Omics," bioRxiv, Oct. 2020, 40 pages.

Wohnhaas et al., "DMSO cryopreservation is the method of choice to preserve cells for droplet-based single-cell RNA sequencing, " Scientific Reports, Jul. 2019. 9(1):10699, 14 pages.

Asp et al., "Spatially Resolved Transcriptomes-Next Generation Tools for Tissue Exploration," Bioessays, Oct. 2020, 42(10):e1900221, 16 pages.

Balakrishnan et al., "Flap endonuclease 1," Annu Rev Biochem., Jun. 2013, 82:119-138.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15): 2911-2914.

Blair et al., "Microarray temperature optimization using hybridization kinetics, " Methods Mol Biol., 2009. 529:171-96.

Bolotin et al., "MiXCR: software for comprehensive adaptive immunity profiling." Nat Methods., May 2015. 12(5):380-1.

Chen et al., "Parallel single nucleotide polymorphism genotyping by surface invasive cleavage with universal detection," Anal Chem., Apr. 2005, 77(8):2400-5.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Ciaccio et al., "Systems analysis of EGF receptor signaling dynamics with microwestern arrays," Nat Methods, Feb. 2010, 7(2):148-55.

Gerard et al., "Excess dNTPs minimize RNA hydrolysis during reverse transcription," Biotechniques, Nov. 2002, 33(5):984, 986, 988, 990.

Hessner et al., "Genotyping of factor V G1691A (Leiden) without the use of PCR by invasive cleavage of oligonucleotide probes," Clin Chem., Aug. 2000, 46(8 Pt 1):1051-6.

Hoffman et al., "Formaldehyde crosslinking: a tool for the study of chromatin complexes," J Biol Chem., Oct. 2015, 290(44):26404-11.

Hughes et al., "Microfluidic Western blotting," PNAS, Dec. 2012, 109(52):21450-21455.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by chlorella virus DNA ligase and a novel iLock assay with improved direct R.NA detection accuracy," Nucleic Acids Research, Oct. 2017, 45(18):e161, 9 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Nilsson et al., "RNA-templated DNA ligation for transcript analysis," Nucleic Acids Res., Jan. 2001. 29(2):578-81.

Olivier, "The Invader assay for SNP genotyping," Mutat. Res., Jun. 2005, 573(1-2):103-110.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Full-length RNA-seq from single cells using Smart-seq2," Nat Protoc., Jan. 2014, 9(1):171-81.

Schouten et al., "Relative quantification of 40 nucleic acid sequences by multiplex ligation-dependent probe amplification." Nucleic Acids Res., Jun. 2002, 30(12):e57, 13 pages.

Singh et al., "High-throughput targeted long-read single cell sequencing reveals the clonal and transcriptional landscape of lymphocytes," Nat Commun., Jul. 2019, 10(1):3120. 13 pages.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

(56) References Cited

OTHER PUBLICATIONS

Sutherland et al., "Utility of formaldehyde cross-linking and mass spectrometry in the study of protein-protein interactions," J. Mass Spectrom., Jun. 2008, 43(6):699-715.
Toubanaki et al.. "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Tu et al., "TCR sequencing paired with massively parallel 3' RNA-seq reveals clonotypic T cell signatures," Nature Immunology, Dec. 2019, 20(12):1692-1699.
Valley et al., "Optoelectronic tweezers as a tool for parallel single-cell manipulation and stimulation," IEEE Trans Biomed Circuits Syst., Dec. 2009, 3(6):424-31.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus, " Biosci Biotechnol Biochem., 2010, 74(9):1925-30.
Aran et al., "xCell: digitally portraying the tissue cellular heterogeneity landscape," Genome Biol., Nov. 2017, 18(1):220, 14 pages.
Plongthongkum et al., "Advances in the profiling of DNA modifications: cytosine methylation and beyond," Nature Reviews Genetics, Aug. 2014, 15(10):647-661.
Salmén et al., "Barcoded solid-phase RNA capture for Spatial Transcriptomics profiling in mammalian tissue sections, " Nature Protocols, Oct. 2018, 13(11):2501-2534.
Hayes et al., "Electrophoresis of proteins and nucleic acids: I-Theory," BMJ, Sep. 1989, 299(6703):843-6.
[No Author Listed], "Chromium Next GEM Single Cell 3' Reagent Kits v3.1 (Dual Index)—User Guide," 10x Genomics, Mar. 2021, Document No. CG000315, 61 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrNOCH17rEkOUXwd19It/e54d99fb08a8f1500aba503005a04a56/CG000238_VisiumSpatialTissueOptimizationUserGuideRevD.pdf>, 43 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.
Blanco et al., "A practical approach to FRET-based PNA fluorescence in situ hybridization," Methods, Dec. 2010, 52(4):343-51.
Czarnik, "Encoding methods for combinatorial chemistry," Curr Opin Chem Biol., Jun. 1997, 1(1):60-6.
Macbeath et al., "Printing proteins as microarrays for high-throughput function determination," Science, Sep. 2000, 289(5485):1760-1763.
Morlan et al., "Selective depletion of rRNA enables whole transcriptome profiling of archival fixed tissue," PLoS One, Aug. 2012, 7(8):e42882, 8 pages.
Pellestor et al., "The peptide nucleic acids (PNAs), powerful tools for molecular genetics and cytogenetics," Eur J Hum Genet., Sep. 2004, 12(9):694-700.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Niedringhaus et al., "Landscape of next-generation sequencing technologies," Anal Chem., Jun. 2011, 83(12):4327-41.
Qiu et al., "Combination probes with intercalating anchors and proximal fluorophores for DNA and RNA detection," Nucleic Acids Research, Sep. 2016, 44(17):e138, 12 pages.
Zhao et al., "Isothermal Amplification of Nucleic Acids," Chemical Reviews, Nov. 2015, 115(22):12491-12545.
U.S. Appl. No. 16/353,937, Frisen et al..
U.S. Appl. No. 17/707,189, Chell et al..
Wang et al., "Optimization of Process Conditions for Infected Animal Tissues by Alkaline Hydrolysis Technology," Procedia Environmental Sciences, 2016, 31:366-374.
U.S. Appl. No. 60/416,118, filed Oct. 3, 2002, Fan et al.
U.S. Appl. No. 61/267,363, filed Dec. 7, 2009, Fan et al.
U.S. Appl. No. 61/839,313, filed Jun. 25, 2013, Chee et al.
U.S. Appl. No. 61/839,320, filed Jun. 25, 2013, Chee et al.
[No Author Listed], "Chromium Next GEM Single Cell 3' Reagent Kits v3.1," User Guide, Document No. CG000204, 10x Genomics, Nov. 2019, 58 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek@ Multiplex 96x96 User Manual," Olink Proteomics, Olink Bioscience, Uppsala, Sweden, 2017, 20 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGHH3RWpd1bFVhalpexR/8baa08d9007157592b65b2cdc7130990/CG000239_VisiumSpatialGeneExpression_UserGuide_RevD.pdf>, 70 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrNOCH17rEkOUXwd19It/e54d99fb08a8f1500aba503005a04a56/CG000238_VisiumSpatialTissueOptimizationUserGuide_RevD.pdf>, 43 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Andor.com [online], "Discover new ways of seeing, " Next Generation Digital Illumination, Mosaic 3, 2020. 11 pages.
Andresen et al., "Helicase-dependent amplification: use in OnChip amplification and potential for point-of-care diagnostics," Expert Rev Mol Diagn., Oct. 2009, 9(7):645-650.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.

(56) References Cited

OTHER PUBLICATIONS

Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates, " Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29. 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bimey et al., "Identification and analysis of functional elements in 1% of the human genome by the Encode pilot project." Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35 - The Cleavase I enzyme for mutation and polymorphism scanning, " PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections, " Biotechniques, 1998, 24(1):92-100.
Calvert, "Materials science. Printing cells," Science, Oct. 2007, 318(5848):208-209.
Carter et al., "Stabilization of an optical microscope to 0.1 nm in three dimensions," Applied Optics, 2007. 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009. 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12): 1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip. Nov. 2020, 20(21):3899-3913.
Chrisey et al., "Covalent attachment of synthetic DNA to self-assembled monolayer films." Nucleic Acids Res., Aug. 1996, 24(15):3031-9.
Cockroft et al., "A single-molecule nanopore device detects DNA polymerase activity with single-nucleotide resolution," J Am Chem Soc., Jan. 2008, 130(3):818-20.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing, " PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002. 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dhindsa et al., "Virtual Electrowetting Channels: Electronic Liquid Transport with Continuous Channel Functionality." Lab Chip, 2010, 10:832-836.
Dressman et al., "Transforming single DNA molecules into fluorescent magnetic particles for detection and enumeration of genetic variations," Proc. Natl. Acad. Sci. USA, 2003. 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," Bio Techniques, 1996, 20(4):584-91.

(56) References Cited

OTHER PUBLICATIONS

Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges." Clin Chem, 2010, 56(2):186-193.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fluidigm, "Hyperion Imaging System: Visualize a new path forward," Feb. 2018, retrieved from URL <https://www.fluidigm.com/binaries/content/documents/fluidigm/search/hippo%3 Aresultset/hyperion-imaging-system-br-400326/fluidigm%3Afile>, 27 pages.
Fluidigm, "Immuno-Oncology Research with the Hyperion Imaging System: A high-parameter imaging solution at subcellular resolution to characterize the immune repertoire in the tumor microenvironment." Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.
Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile> 6 pages.
Fluidigm, "Maxpar Antibodies for Imaging Mass Cytometry," Mar. 2018, retrieved from URL <https://www.fluidigm.com/binaries/content/documents/fluidigm/search/hippo%3 Aresultset/hyperion-antibodies-for-imaging-mass-cytometry-br-101-7115/fluidigm%3Afile>, 2 pages.
Fodor et al., "Light-directed, spatially addressable parallel chemical synthesis," Science, 1995, 251(4995):767-773.
Forcucci et al., "All-plastic miniature fluorescence microscope for point-of-care readout of bead-based bioassays.," J. Biomed Opt., 2015, 20(10):105010, 15 pages.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011. 108(22):9026-9031.
Fu et al., "Repeat subtraction-mediated sequence capture from a complex genome, " Plant J., Jun. 2010. 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Genc@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation, " N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hahnke et al., "Striptease on glass: validation of an improved stripping procedure for in situ microarrays," J Biotechnol., Jan. 2007, 128(1):1-13.
Hardenbol et al., "Highly multiplexed molecular inversion probe genotyping: over 10,000 targeted SNPs genotyped in a single tube assay, " Genome Res., Feb. 2005, 15(2):269-75.
Hardenbol et al., "Multiplexed genotyping with sequence-tagged molecular inversion probes," Nature Biotechnol., Jun. 2003, 21(6):673-678.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount Arabidopsis samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hoyer et al., "Electrostatic spraying: a novel technique for preparation of polymer coatings on electrodes," Anal Chem, Nov. 1996, 68(21):3840-4.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990. 265(31):18829-32, Abstract.

(56) References Cited

OTHER PUBLICATIONS

Jamur et al., "Permeabilization of cell membranes.," Method Mol. Biol., 2010, 588:63-66.

Jemt et al., "An automated approach to prepare tissue-derived spatially barcoded RNA-sequencing libraries," Scientific Reports, 2016, 6:37137, 10 pages.

Kap et al., "Histological assessment of PAXgene tissue fixation and stabilization reagents," PLoS One, 2011, 6:027704, 10 pages.

Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.

Kaya-Okur et al., "CUT&Tag for efficient epigenomic profiling of small samples and single cells." Apr. 2019, 10(1):1930, 10 pages.

Kennedy-Darling et al., "Measuring the Formaldehyde Protein-DNA Cross-Link Reversal Rate," Analytical Chemistry, 2014, 86(12):5678-5681.

Kent et al., "Polymerase θ is a robust terminal transferase that oscillates between three different mechanisms during end-joining" Elife, Jun. 2016, 5:e13740, 25 pages.

Kirby et al., "Cryptic plasmids of *Mycobacterium avium*: Tn552 to the rescue," Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.

Korbel et al., "Paired-end mapping reveals extensive structural variation in the human genome," Science, 2007, 318(5849):420-426.

Kozlov et al., "A highly scalable peptide-based assay system for proteomics, " PLoS ONE, 2012, 7(6):c37441, 10 pages.

Kozlov et al., "A method for rapid protease substrate evaluation and optimization," Comb Chem High Throughput Screen, 2006, 9(6):481-87.

Kristensen et al., "High-Throughput Methods for Detection of Genetic Variation," BioTechniques, Feb. 2001, 30(2):318-332.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmocogenomics, Feb. 2000, 1(1):95-100.

Lage et al., "Whole genome analysis of genetic alterations in small DNA samples using hyperbranched strand displacement amplification and array-CGH," Genome Research, 2003, 13(2):294-307.

Lampe et al., "A purified mariner transposase is sufficient to mediate transposition in vitro," EMBO J., Oct. 1996, 15(19):5470-9.

Landegren et al., "Reading bits of genetic information: methods for single-nucleotide polymorphism analysis, " Genome Res., Aug. 1998. 8(8):769-76.

Langdale et al., "A rapid method of gene detection using DNA bound to Sephacryl," Gene, 1985, 36(3):201-210.

Larman et al., "Sensitive, multiplex and direct quantification of RNA sequences using a modified RASL assay," Nucleic Acids Research, 2014, 42(14):9146-9157.

Lee et al., "Fluorescent in situ sequencing (FISSEQ) of RNA for gene expression profiling in intact cells and tissues," Nature Protocols, 2015, 10(3):442-458.

Lee et al., "Improving the efficiency of genomic loci capture using oligonucleotide arrays for high throughput resequencing, " BMC Genomics, Dec. 2009, 10:646, 12 pages.

Leriche et al., "Cleavable linkers in chemical biology," Bioorganic & Medicinal Chemistry, 2012, 20:571-582.

Levene et al., "Zero-Mode Waveguides for Single-Molecule Analysis at High Concentrations," Science 299, 682-686. 2003.

Li et al., "A photocleavable fluorescent nucleotide for DNA sequencing and analysis, " Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "DNA molecules and configurations in a solid-state nanopore microscope," Nat Mater., Sep. 2003, 2(9):611-5.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lin et al., "Highly multiplexed imaging of single cells using a high-throughput cyclic immunofluorescence method," Nat Commun., Sep. 2015, 6:8390, 7 pages.

Lin et al., "Microfluidic cell trap array for controlled positioning of single cells on adhesive micropatterns," Lab Chip, Feb. 2013, 13(4):714-721.

Linnarsson, "Recent advances in DNA sequencing methods—general principles of sample preparation," Experimental Cell Rescarch, 2010, 316(8):1339-1343.

Liu et al., "High-Spatial-Resolution Multi-Omics Atlas Sequencing of Mouse Embryos via Deterministic Barcoding in Tissue," BioRxiv, 2019, 55 pages.

Lizardi et al., "Mutation detection and single-molecule counting using isothermal rolling-circle amplification," Nat. Genet., 1998, 19(3):225-232.

Lovatt et al., "Transcriptome in vivo analysis (TIVA) of spatially defined single cells in live tissue," Nature Methods, 2013, 11(2):190-196.

Lu et al., "A microfluidic electroporation device for cell lysis." Lab Chip., Jan. 2005, 5(1):23-29.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.

Lundin et al., "Increased throughput by parallelization of library preparation for massive sequencing." PLoS One, Apr. 2010, 5(4):e10029, 7 pages.

Lundquist et al.. "Parallel confocal detection of single molecules in real time," Opt. Lett. 33, 1026-1028, 2008.

Lyck et al., "Immunohistochemical markers for quantitative studies of neurons and glia in human neocortex," J Histochem Cytochem, 2008, 56(3):201-21.

MacIntyre, "Unmasking antigens for immunohistochemistry.," Br J Biomed Sci., 2001, 58(3):190-6.

Marx, "Method of the Year: spatially resolved transcriptomics," Nature Methods. 2021, 18(1):9-14.

Mccloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miele et al., "Mapping cis- and trans-chromatin interaction networks using chromosome conformation capture (3C)," Methods Mol Biol., 2009, 464:105-21.

Miller et al., "Basic concepts of microarrays and potential applications in clinical microbiology," Clinical Microbiology Reviews, 2009, 22(4):611-633.

(56) References Cited

OTHER PUBLICATIONS

Mishra et al., "Three-dimensional genome architecture and emerging technologies: looping in disease," Genome Medicine, 2017, 9(1):87. 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamH1 and Sau3A," Gene, 1982, 20(3):317-322.
Motea et al., "Terminal deoxynucleotidyl transferase: the story of a misguided DNA polymerase." Biochim Biophys Acta., May 2010, 1804(5):1151-66.
Nandakumar et al., "How an RNA Ligase Discriminates RNA versus DNA Damage," Molecular Cell, 2004, 16:211-221.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization." Anal Biochem, May 1995. 227(1):201-9.
Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen, " Proc Natl Acad Sci USA, Jun. 1992, 89(12):5577-5581.
Petterson et al., "Generations of sequencing technologies," Genomics, 2009, 93(2):105-111.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family." Curr Top Microbiol Immunol., 1996, 204:125-43.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing, " Genome Res, Jan. 2001, 11(1):3-11.
Rountenberg et al., "Microfluidic probe: a new tool for integrating microfluidic environments and electronic wafer-orobina, " Lab Chip, Oct. 2009, 10: 123-127.
Roy et al., "Assessing long-distance RNA sequence connectivity via RNA-templated DNA-DNA ligation," eLife, 2015, 4:e03700, 21 pages.
Saxonov et al., "10x Genomics, Mastering Biology to Advance Human Health, " PowerPoint, 10x. 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.
Shalon et al., "A Dna microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome." Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Soni and Meller, "Progress toward ultrafast DNA sequencing using solid-state nanopores," Clin Chem., 2007, 53:1996-2001.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo." Nat Med., Jun. 2005. 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.

(56) References Cited

OTHER PUBLICATIONS

Tijssen et al., "Overview of principles of hybridization and the strategy of nucleic acid assays" in Techniques in Biochemistry and Molecular Biology—Hybridization with Nucleic Acid Probes, 1993. 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA." Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nature Methods, 2019, 9 pages.
Vincent et al.. "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019. 116(22):10842-10851.
Wang et al., "High-fidelity mRNA amplification for gene profiling." Nature Biotechnology, Apr. 2000. 18(4):457-459.
Wang, "RNA amplification for successful gene profiling analysis." J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wheeler et al., "Microfluidic device for single-cell analysis," Analytical Chemistry, Jul. 2003, 75(14):3581-3586.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in *Bacillus anthracis*, " J Microbiol Methods, Dec. 2007, 71(3):332-5.
Wolf et al.. "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries." Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Yoda et al., "Site-specific gene expression analysis using an automated tissue micro-dissection punching system," Sci Rep., Jun. 2017. 7(1):4325, 11 pages.
Zhang et al., "Archacal RNA ligase from thermoccocus kodakarensis for template dependent ligation." RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes†." Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.

\* cited by examiner

ELECTROPHORETIC SYSTEM AND METHOD FOR ANALYTE CAPTURE

CROSS-REFERENCE TO RELATED APPLICATION

This application claims the benefit of U.S. Patent Application Ser. No. 62/962,559, titled ELECTROPHORETIC SYSTEM AND METHOD FOR PREPARING SAMPLE, filed Jan. 17, 2020, the disclosure of which is hereby incorporated by reference in its entirety.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Various methods have been used to capture analytes from a biological sample for analyzing analyte data in the sample. In some applications, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis.

SUMMARY

This document generally relates to electrophoretic apparatuses, systems, and methods for capturing analytes from a sample, such as a biological sample.

Some embodiments described herein include an electrophoretic system for analyte capture from a biological sample, such as a cell or a tissue sample including a cell. The electrophoretic system can be used to permeabilize the sample to allow analytes to be released from the sample (e.g., the cell therein). For example, the sample can be contacted with capture probes attached to a substrate (e.g., a surface of the substrate), and an electric field created by the electrophoretic system can cause analytes to be released from the cell, and effectively migrate toward and bind to the capture probes attached to the substrate. Loss of spatial resolution can occur when analytes migrate from a sample to capture probes (e.g., feature array) and a component of diffusive migration occurs in a transverse (e.g., lateral) direction, approximately parallel to the surface of the substrate on which the sample is mounted. The electrophoretic system described herein can actively direct analytes released from a cell to the capture probes, thereby improving spatial resolution by eliminating or reducing such diffusive migration in the transverse direction.

In some implementations, a substrate (e.g., slide) on which a sample (e.g., cell, tissue, etc.) is placed can include a conductive material and used as an anode in the electrophoretic system described herein. An electrode can be placed to be spaced apart from the substrate, and used as a cathode. A non-conductive spacer can be arranged between the substrate and the electrode. The substrate, the electrode, and the spacer can be at least partially immersed in a buffer. The electrophoretic system can apply a voltage between the electrodes (i.e., the substrate comprising the anode, and the electrode as the cathode) to cause analytes to release from the sample and migrate to capture probes attached to the substrate.

In some implementations, the electrophoretic system described herein can include a variety of substrate cassettes configured for analyzing multiple samples. For example, a substrate cassette can be configured to engage a substrate that has multiple substrate regions. The substrate cassette can include a plurality of apertures corresponding to the substrate regions of the substrate, respectively. The plurality of apertures can be used as a plurality of chambers for receiving buffers, respectively. The substrate can be made of a conductive material and used as a common anode for the plurality of chambers. A cathode can be configured to include a plurality of electrode plates or pins that can extend into the chambers at least partially filled with buffers, respectively. The electrophoretic system can apply a voltage between the substrate (as the anode) and the cathode (including the electrode plates or pins) to cause analytes to release from the samples in each of the substrate regions, and migrate to a capture probe provided at each of the substrate regions of the substrate.

Particular embodiments described herein include an electrophoretic system for migrating analytes in a biological sample. The system includes a substrate, a cathode, a buffer chamber, and a controller. The substrate may include a substrate region configured to place a capture probe thereon. The substrate region may be configured to receive the biological sample containing analytes. The substrate may be configured to be usable as an anode. The cathode may be spaced apart from the substrate. The buffer chamber may be disposed between the substrate and the cathode and configured to contain a buffer. The controller may be configured to generate an electric field between the substrate and the cathode such that the analytes in the biological sample migrate toward the capture probe on the substrate.

In some implementations, the system can optionally include one or more of the following features. The substrate may include a conductive material. The substrate may be coated with a conductive material. The conductive material may include at least one of tin oxide (TO), indium tin oxide (ITO), a transparent conductive oxide (TCO), aluminum doped zinc oxide (AZO), or fluorine doped tin oxide (FTO). The substrate may include an array of substrate regions configured to place capture probes thereon. The capture probe may be immobilized on the substrate region. The system may include a spacer disposed between the substrate and the cathode to define the buffer chamber. The buffer may include a permeabilization reagent. The system may include a power supply, and electrical wires connecting the power supply to the substrate and the cathode. The system may include a substrate cassette configured to hold the substrate and include a plurality of apertures configured to define a plurality of buffer chambers on the substrate.

Particular embodiments described herein include a method for migrating analytes in a biological sample to a substrate. The method may include placing the biological sample in contact with a capture probe on a substrate, the biological sample including analytes; arranging a cathode relative to the substrate at a distance; providing a buffer between the cathode and the biological sample on the substrate; and generating an electric field between the cathode and the substrate to cause the analytes to migrate toward the capture probe on the substrate.

In some implementations, the system can optionally include one or more of the following features. The capture probe may be immobilized on the substrate. The substrate may include a conductive material. The substrate may be coated with a conductive material. The conductive material may include at least one of tin oxide (TO), indium tin oxide (ITO), a transparent conductive oxide (TCO), aluminum doped zinc oxide (AZO), or fluorine doped tin oxide (FTO). The substrate may include an array of substrate regions configured to place capture probes thereon. The method may include arranging a spacer between the substrate and the cathode to contain the buffer between the substrate and the cathode. The buffer may include a permeabilization reagent. The method may include connecting electrical wires from a power supply with the substrate and the cathode, respectively.

Particular embodiments described herein include an electrophoretic system. The system may include a substrate, a substrate cassette, a cathode assembly, and a controller. The substrate may include a plurality of substrate regions including capture probes and one or more biological samples containing analytes. The substrate cassette may be configured to hold the substrate and include a plurality of apertures corresponding to the plurality of substrate regions of the substrate. The plurality of apertures may be configured to define a plurality of buffer chambers on the plurality of substrate regions of the substrate. The cathode assembly may include a plurality of electrode plates. The plurality of electrode plates may be configured to position within the plurality of buffer chambers of the substrate cassette. The controller may be configured to generate electric fields between the plurality of substrate regions and the plurality of electrode plates, respectively, such that the analytes in the biological samples migrate toward the capture probes on the substrate.

In some implementations, the system can optionally include one or more of the following features. The biological samples may be placed in contact with the capture probes on the plurality of substrate regions. The plurality of substrate regions may include a plurality of wells recessed on the substrate. The substrate cassette may include a substrate holder and a gasket. The substrate holder may include a substrate mount for securing the substrate. The gasket may include a plurality of gasket apertures configured to align with the plurality of substrate regions when the substrate is secured by the substrate holder. The plurality of apertures may include the plurality of gasket apertures. The substrate holder may include a plurality of holder apertures configured to align with the plurality of gasket apertures when the substrate is secured by the substrate holder. The plurality of apertures may include the plurality of gasket apertures and the plurality of holder apertures. The system may include a substrate cover configured to be arranged on the substrate cassette and include a plurality of cover apertures configured to align with the plurality of apertures of the substrate cassette. The cathode assembly may be mounted to the substrate cover and the plurality of electrode plates of the cathode assembly may be configured to extend through the plurality of cover apertures into the plurality of apertures of the substrate. The substrate may be coated with a conductive material. The conductive material may include at least one of tin oxide (TO), indium tin oxide (ITO), a transparent conductive oxide (TCO), aluminum doped zinc oxide (AZO), or fluorine doped tin oxide (FTO). The buffer may include a permeabilization reagent. The system may include a power supply, and electrical wires connecting the power supply to the cathode and each of the plurality of substrate regions of the substrate.

Particular embodiments described herein include a method for capturing analytes from a biological sample. The method may include placing biological samples in contact with capture probes on a substrate, the biological sample including analytes; arranging a substrate cassette onto the substrate to align a plurality of apertures of the substrate cassette with a plurality of substrate regions of the substrate and define a plurality of buffer chambers on the plurality of substrate regions; supplying buffers in the plurality of buffer chambers; arranging a cathode to place a plurality of electrode plates of the cathode within the plurality of buffer chambers; and generating electric fields between the plurality of substrate regions and the plurality of electrode plates to cause the analytes in the biological samples to migrate toward the capture probes on the substrate.

In some implementations, the system can optionally include one or more of the following features. The capture probes may be immobilized on the plurality of substrate regions. The biological samples may be placed in contact with the capture probes on the plurality of substrate regions. The plurality of substrate regions may include a plurality of wells recessed on the substrate. The substrate cassette may include a substrate holder and a gasket. The substrate holder may include a substrate mount for securing the substrate. The gasket may include a plurality of gasket apertures configured to align with the plurality of substrate regions when the substrate is secured by the substrate holder. The plurality of apertures may include the plurality of gasket apertures. The substrate holder may include a plurality of holder apertures configured to align with the plurality of gasket apertures when the substrate is secured by the substrate holder. The plurality of apertures may include the plurality of gasket apertures and the plurality of holder apertures. The method may include providing a substrate cover including a plurality of cover apertures and mounting the cathode assembly; and placing the substrate cover onto the substrate cassette such that the plurality of cover apertures of the substrate cover is aligned with the plurality of apertures of the substrate cassette, respectively, and such that the plurality of plates of the cathode assembly extends through the plurality of cover apertures into the plurality of apertures of the substrate. The substrate may be coated with a conductive material. The conductive material may include at least one of tin oxide (TO), indium tin oxide (ITO), a transparent conductive oxide (TCO), aluminum doped zinc oxide (AZO), or fluorine doped tin oxide (FTO).

The devices, system, and techniques described herein may provide one or more of the following advantages. Some embodiments described herein include an electrophoretic system configured to provide appropriate permeabilization of a sample and reduce lateral diffusion that may result from incomplete permeabilization of the sample, thereby increasing the amount of analytes captured and available for detection.

Further, the electrophoretic system described herein can eliminate or reduce additional permeabilization processes. The electrophoretic system can achieve a desired level of spatial resolution without other types of permeabilization or with reduced additional permeabilization. For example, the electrophoretic system can eliminate a need of a permeabilization agent. Alternatively, the electrophoretic system can permit for a reduced amount of permeabilization agent to be used to achieve a desired level of spatial resolution. For example, prior to electrophoresis, a sample can be contacted with a permeabilization agent only for a shorter period of time than a time for complete permeabilization of the sample. Such incomplete permeabilization of the sample can be compensated by the electrophoretic system described herein that eliminates or reduces lateral diffusion of migrating analytes (i.e., analyte diffusion in the transverse direction–orthogonal to the normal direction to the surface of the sample).

Moreover, the electrophoretic system described herein can cause analytes to actively migrate to capture probes by electrophoretic transfer, thereby permitting for the spatial location of the analytes captured by the capture probes on a substrate to be more precise and representative of the spatial location of the analytes in the biological sample than when the analytes are migrated to the capture probes under different environments.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
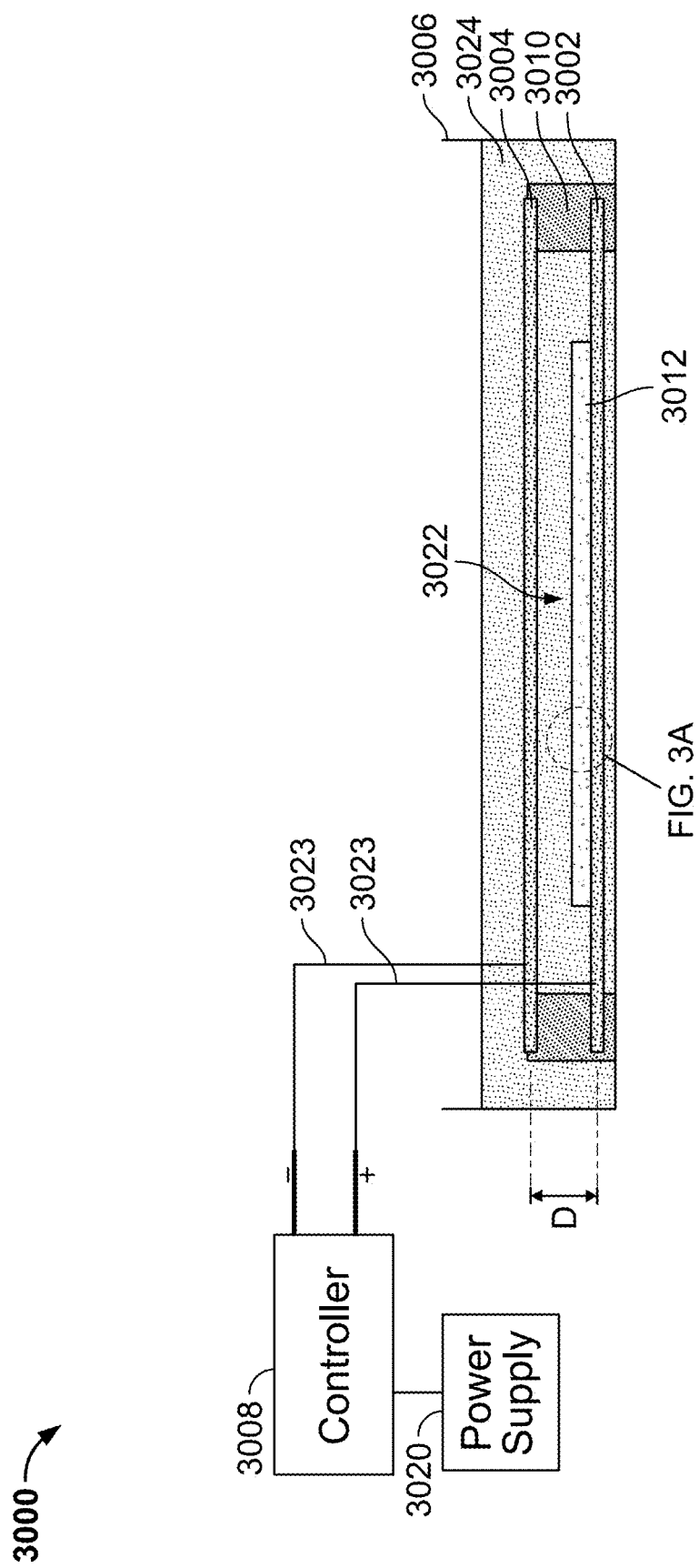
FIG. 1 schematically illustrates an example electrophoretic system.

In general, the present disclosure provides electrophoretic apparatuses, systems, and methods for preparing a sample for a spatial analysis described herein.

Some embodiments include an electrophoretic system for preparing a biological sample, such as a cell or a tissue sample including a cell. The electrophoretic system can be used to permeabilize the sample to allow analytes to be released from the sample (e.g., the cell therein). For example, the sample can be contacted with capture probes attached to a substrate (e.g., a surface of the substrate), and an electric field created by the electrophoretic system can cause analytes to be released from the cell, and effectively migrate toward and bind to the capture probes attached to the substrate. The electrophoretic system described herein can actively direct analytes released from a cell to the capture probes, thereby improving spatial resolution by eliminating or reducing diffusive migration.

In some implementations, a substrate on which a sample is placed can include a conductive material that can be used as an anode in the electrophoretic system described herein. An electrode can be placed in an arrangement in the system such that the electrode is spaced apart from the substrate. The electrode can be used as a cathode in the system. A non-conductive spacer can be arranged between the substrate and the electrode. In some embodiments, one or more conductive materials, electrodes, and/or non-conductive spacers can be used in the system described herein. The substrate, the electrode, and the spacer can be at least partially immersed in a buffer. In some embodiments, the substrate, the electrode, the spacer, or any combination thereof, can be fully immersed in a buffer. The electrophoretic system can apply a voltage between the electrodes (i.e., the substrate as the anode, and the electrode as the cathode) to cause analytes to release from the sample and migrate to capture probes attached to the substrate.

In some implementations, a variety of substrate cassettes for analyzing multiple samples can be used with the electrophoresis system provided herein. For example, a substrate cassette can be configured to engage a substrate that has multiple substrate regions. The substrate cassette can include a plurality of apertures corresponding to the substrate regions of the substrate, respectively. The plurality of apertures can be used as a plurality of chambers for receiving buffers, respectively. The substrate can be made of a conductive material and used as a common anode for the plurality of chambers. A cathode can be configured to include a plurality of electrode plates that can extend into the chambers at least partially filled with buffers, respectively. The electrophoretic system can apply a voltage between the substrate (as the anode) and the cathode (including the electrode plates) to cause analytes to release from the samples in each of the substrate regions, and migrate to a capture probe provided at each of the substrate regions of the substrate.

Referring to FIGS. 1-4, an example electrophoretic system 3000 is described for preparing a sample. FIG. 1 schematically illustrates an example configuration of the electrophoretic system 3000. In some implementations, the electrophoretic system 3000 can be used to provide electrophoretic permeabilization of a sample, and/or actively cause analytes in the sample to migrate to capture probes on a substrate. In some embodiments, the electrophoretic system 3000 can be used to enhance electrophoretic permeabilization of a sample by actively directing analytes in the sample with desired directionality. For example, electrophoretic permeabilization by the system 3000 can result in higher analyte capture events (by, e.g., driving more analytes to the capture probes) and better spatial fidelity of captured analytes (e.g., on a feature array) than random diffusion onto matched substrates without the application of an electric (e.g., increases resolution of spatial analyte detection).

In some implementations, the electrophoretic system 3000 can include a substrate 3002 as a first electrode, a second electrode 3004, an electrophoretic container 3006, and a control system 3008. The system 3000 can further include a spacer 3010.

Figure 2:
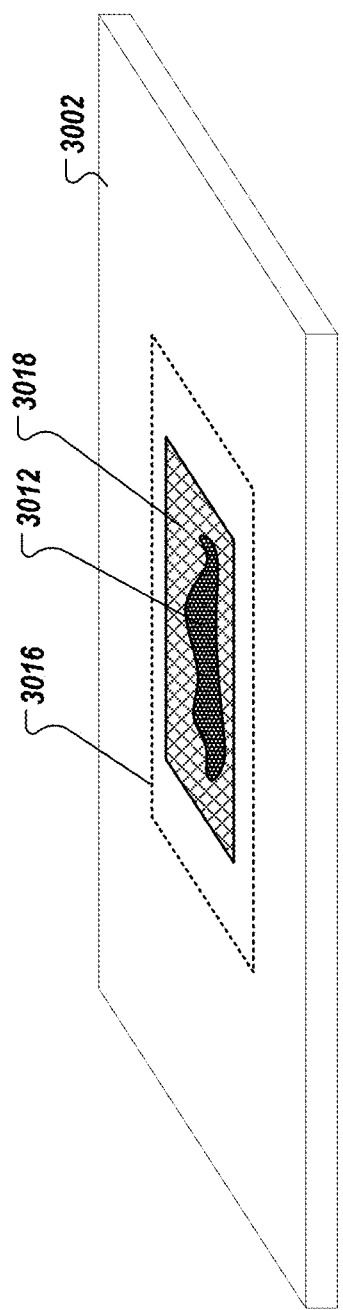
FIG. 2 schematically illustrates an example substrate.

Referring to FIG. 2, the substrate 3002 is configured to receive a sample 3012 that contains analytes. The sample 3012 includes a biological sample, such as a cell or a tissue including a cell. The substrate 3002 can include a substrate region 3016 for receiving the sample 3012 thereon. In some implementations, the substrate 3002 can place a plurality of capture probes 3018 on the substrate region 3016. The capture probes 3018 can be placed on the substrate region 3016 in various manners, such as a variety of ways generally described herein. For example, the capture probes 3018 can be directly attached to a feature that is on an array. Alternatively or in addition, the capture probes 3018 can be immobilized on the substrate region 3016 of the substrate 3002. The sample 3012 can be prepared on the substrate 3002 in various ways generally described herein.

In some implementations, the substrate 3002 is configured to be used as a first electrode in the electrophoretic system 3000. For example, the substrate 3002 can be used as an anode. In another example, the substrate 3002 can be used as a cathode.

The substrate 3002 can be configured as a conductive substrate described generally herein. For example, the substrate 3002 can include one or more conductive materials that permit for the substrate 3002 to function as an electrode (e.g., the anode). Examples of such a conductive material include tin oxide (TO), indium tin oxide (ITO), a transparent conductive oxide (TCO), aluminum doped zinc oxide (AZO), fluorine doped tin oxide (FTO), and any combination thereof. Alternatively or in addition, other materials may be used to provide desired conductivity to the substrate 3002. In some implementations, the substrate 3002 can be coated with the conductive material. For example, the substrate 3002 can include a conductive coating on the surface thereof, and the sample 3012 is provided on the coating of the substrate 3002.

Although the substrate 3002 is illustrated to include a single substrate region 3016 in FIG. 2, other implementations of the substrate 3002 can include a plurality of substrate regions that are configured to place capture probes and/or samples thereon, respectively.

In the illustrated example of FIG. 1, the substrate 3002 is used as the anode, and the second electrode 3004 is configured as a cathode. In this example, therefore, the second electrode 3004 can also be referred to as the cathode 3004. In some implementations, the cathode 3004 can include a conductive plate, one or more pins, or other suitable configurations. In other implementations, the cathode 3004 can include a conductive substrate that is similar to the substrate 3002. In this configuration, in some implementations, the cathode 3004 does not include capture probes, agents, solutions, or other substances or materials that may interact with the sample placed on the substrate 3002.

The substrate 3002 and the cathode 3004 can be arranged within the electrophoretic container 3006. The electrophoretic container 3006 can provide a buffer chamber 3022 between the substrate 3002 and the cathode 3004. The buffer chamber 3022 is configured to contain a buffer 3024. In some implementations, the substrate 3002 and the cathode 3004 can be fully immersed into the buffer 3024. In alternative implementations, either or both of the substrate 3002 and the cathode 3004 can be partially inserted into the buffer 3024 contained in the electrophoretic container 3006.

The buffer 3024 can be of various types. In some implementations, the buffer 3024 includes a permeabilization reagent. In some implementations, the buffer 3024 does not include a permeabilization reagent. The buffer 3024 is contained in the buffer chamber 3022 throughout the electrophoretic process.

The spacer 3010 can be disposed between the substrate 3002 and the cathode 3004 to space them apart at a distance D. The spacer 3010 is made of non-conductive material, such as plastic, glass, porcelain, rubber, etc. The distance D can be determined to provide a desired level of spatial resolution based on several factors, such as the strength and/or duration of electric field generated between the substrate 3002 and the cathode 3004, and other parameters described herein. The spacer 3010 can define at least part of the buffer chamber 3022 between the substrate 3002 and the cathode 3004.

The controller 3008 operates to generate an electric field (−E) between the substrate 3002 and the cathode 3004. As illustrated in FIG. 3, the analytes 3014 in the sample 3012 can migrate toward the capture probes 3018 under the electric field (−E). The controller 3008 can operate to apply a voltage between the substrate 3002 and the cathode 3004 using a power supply 3020. The power supply 3020 can include a high voltage power supply. The controller 3008 can be electrically connected to the substrate 3002 and the cathode 3004 using electrical wires 3023.

FIGS. 3A-D illustrate examples of configurations of a substrate and a sample undergoing electrophoretic process using the electrophoretic system 3000. The application of electric field (−E) causes the analytes 3014 to move towards the capture probes 3018 in the direction of the arrow shown. In some implementations, the analytes 3014 include a protein or a nucleic acid. In some embodiments, the analytes 3014 are negatively charged proteins or nucleic acids. In some embodiments, the analytes 3014 include a positively charged protein or a nucleic acid. In some embodiments, the analytes 3014 includes a negatively charged transcript. For example, the analytes 3014 include a polyA transcript. In some embodiments, the capture probes 3018 are attached to the substrate 3002. In some embodiments, the capture probes 3018 can be attached on a feature of an array array. In some embodiments, the analytes 3014 move towards the capture probes 3018 for a distance (h). In some embodiments, the buffer 3024 (e.g., including a permeabilization reagent) can be in contact with the sample 3012, the substrate 3002, the cathodes 3004, or any combination thereof. The buffer 3024 can include any of the permeabilization reagents disclosed above including but not limited to a permeabilization reagent, a permeabilization buffer, a permeabilization enzyme, a buffer without a permeabilization reagent, a permeabilization gel, and a permeabilization solution.

Figure 3A:
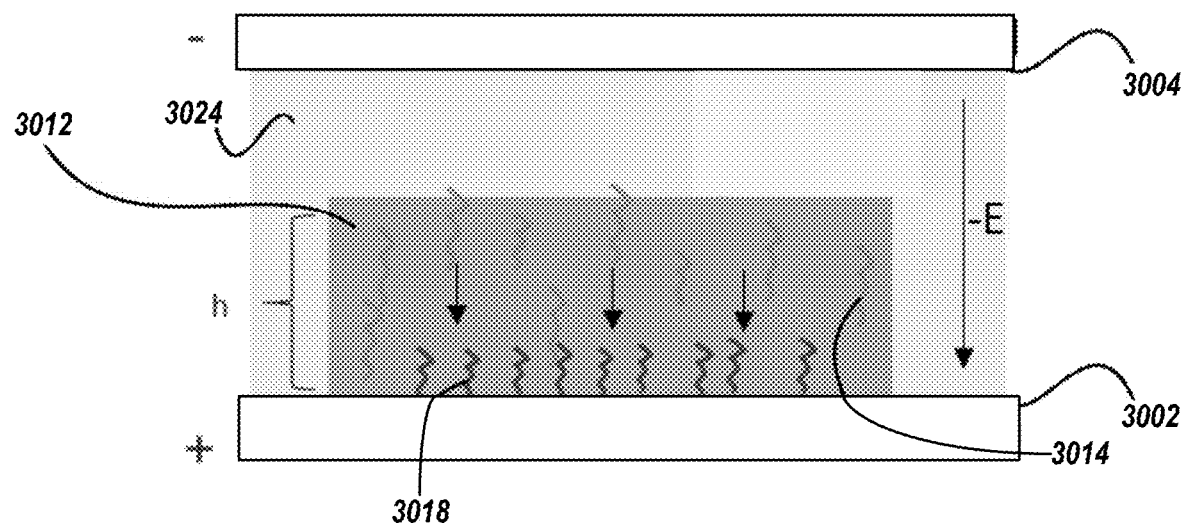
FIGS. 3A-D illustrate example substrates and samples undergoing electrophoretic process.
Figure 3B:
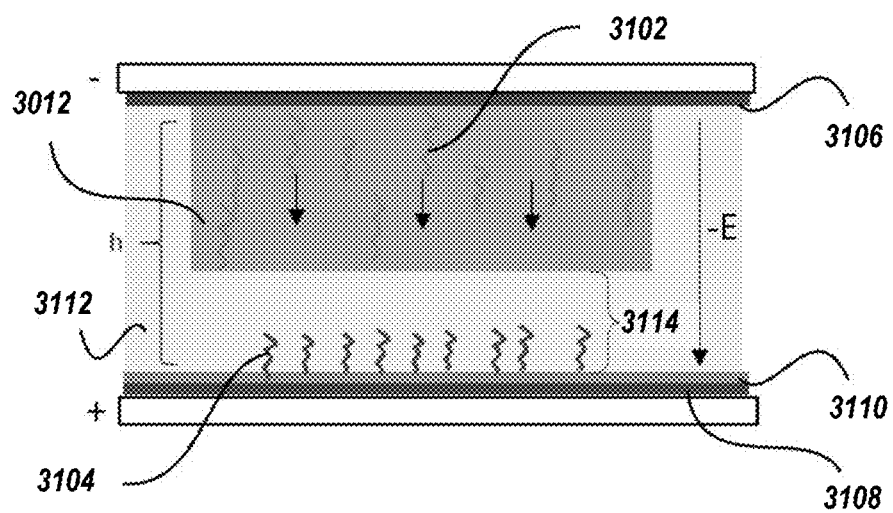
Figure 3C:
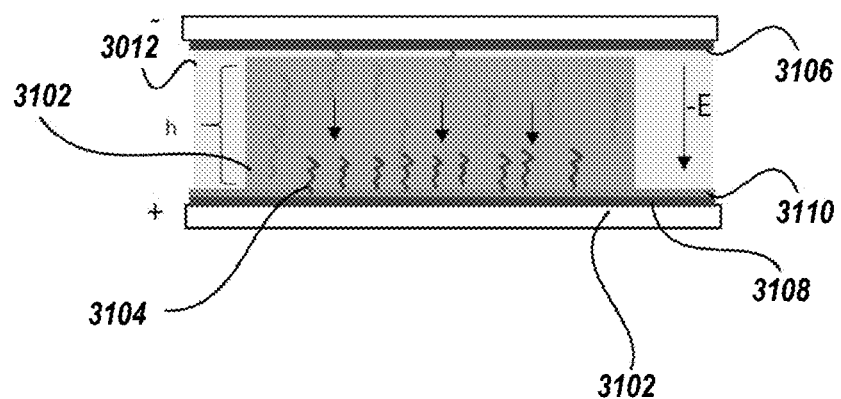
Figure 3D:
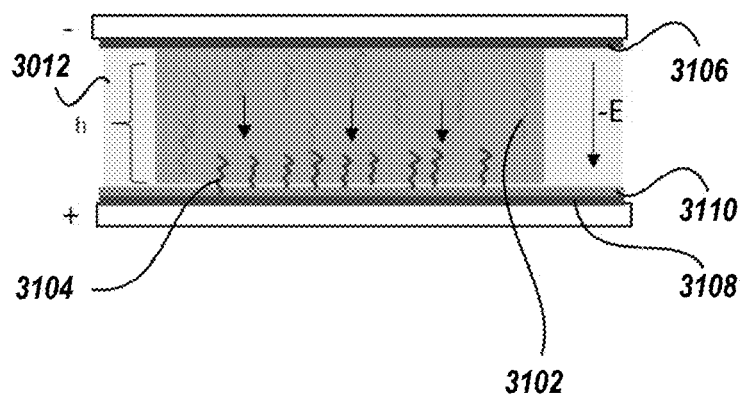

FIG. 3B shows another example configuration in which the sample 3012 is on a first substrate 3106, and there is a gap 3114 in between the sample 3012 and a coating 3110 on the surface of a second substrate 3108. The coating 3110 can be a conductive coating as described herein. For this embodiment, applied electrophoretic charge causes the analytes 3102 to migrate from the biological sample 3012 on the first substrate, through the buffer 3112 and across the gap 3114 to the capture probes 3104 disposed on the second substrate 3108. FIG. 3C shows another example configuration in which sample 3012 is on coating 3110 of the second substrate 3108, but there is no gap present in between the sample 3012 and the first substrate 3106. FIG. 3D shows another example configuration similar to that of FIG. 3B in which sample 3012 is on the first substrate 3106, but there is no or minimal gap present between the sample 3012 and the second substrate 3108 upon which is located the capture probes 3104.

Figure 4:
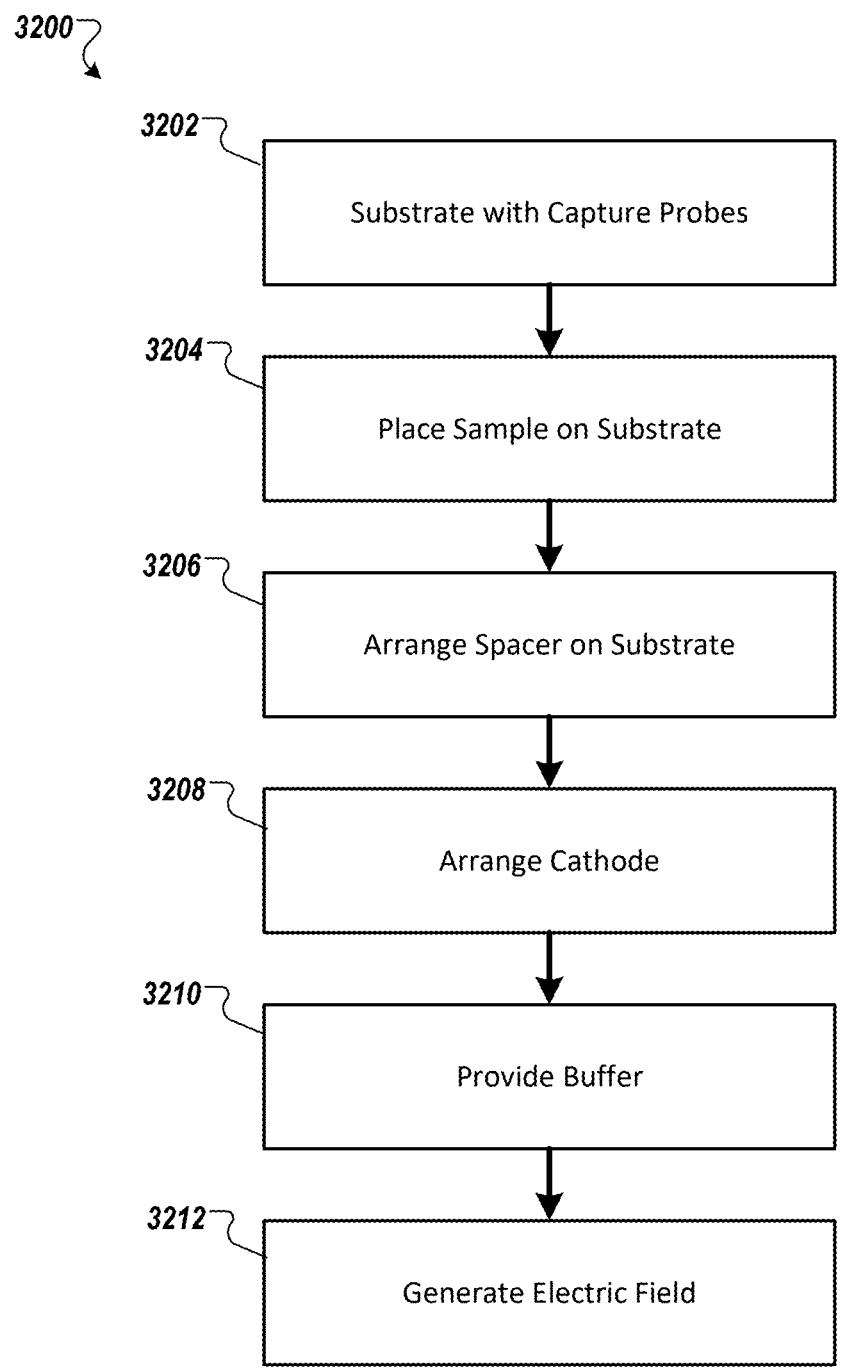
FIG. 4 is a flowchart of an example process for preparing a sample.

FIG. 4 is a flowchart of an example process 3200 for preparing a sample for use in the electrophoretic systems described herein. In some implementations, the process 3200 includes providing a substrate including capture probes (3202), and placing a sample in contact with the the substrate (3204). The capture probes can be attached to the substrate in various ways generally described herein. The sample can be placed on the substrate in various ways generally described herein. As described herein, the substrate can be configured and used as an electrophoretic electrode (also referred to herein as a first electrode). In some implementations, the substrate can be configured as a conductive substrate as described herein, such as by including a conductive material in the substrate or providing a conductive coating on an upper or lower surface of the substrate. In some implementations, the substrate can be used as an anode. In alternative implementations, the substrate can be used as a cathode.

The process 3200 can further include arranging a spacer on or above the substrate (3206). When a second electrode is arranged as described below, the spacer can be arranged between the second electrode and the first electrode (e.g., the substrate). As described herein, the spacer can be made of a non-conductive material and used to provide a buffer chamber between the first and second electrodes.

The process 3200 can include arranging a second electrode relative to the first electrode (e.g., the substrate) at a distance (3208). The second electrode can be used as a cathode when the substrate is used as an anode. Alternatively, the second electrode can be used as an anode when the substrate is used as a cathode. The second electrode can be made of various configurations. For example, the second electrode can include a conductive plate. Alternatively, the second electrode can be configured as a conductive substrate that is configured similarly to the first electrode (e.g., the substrate).

The process 3200 can include providing a buffer between the first electrode and the second electrode (3210). The buffer can be contained in the buffer chamber that is provided by the spacer and used to at least partially immerse the first electrode (e.g., the substrate), the second electrode, or both. In some implementations, the buffer can include a permeabilization reagent. Other buffers as described generally herein can be used in other implementations. In some embodiments, both electrodes are immersed in a buffer.

The process 3200 can include generating an electric field between the first electrode (e.g., the substrate) and the second electrode (3212). Under the electric field, analytes included in the sample can migrate toward the capture probe on the substrate, wherein the analytes can hybridize to the captures probes. In some implementations, the electric field is generated by applying a voltage between the first and second electrodes, using a power supply electrically connected to the first and second electrodes. For example, the process 3200 can include connecting electrical wires from the power supply with the first electrode (e.g., the substrate) and the second electrode.

Figure 5:
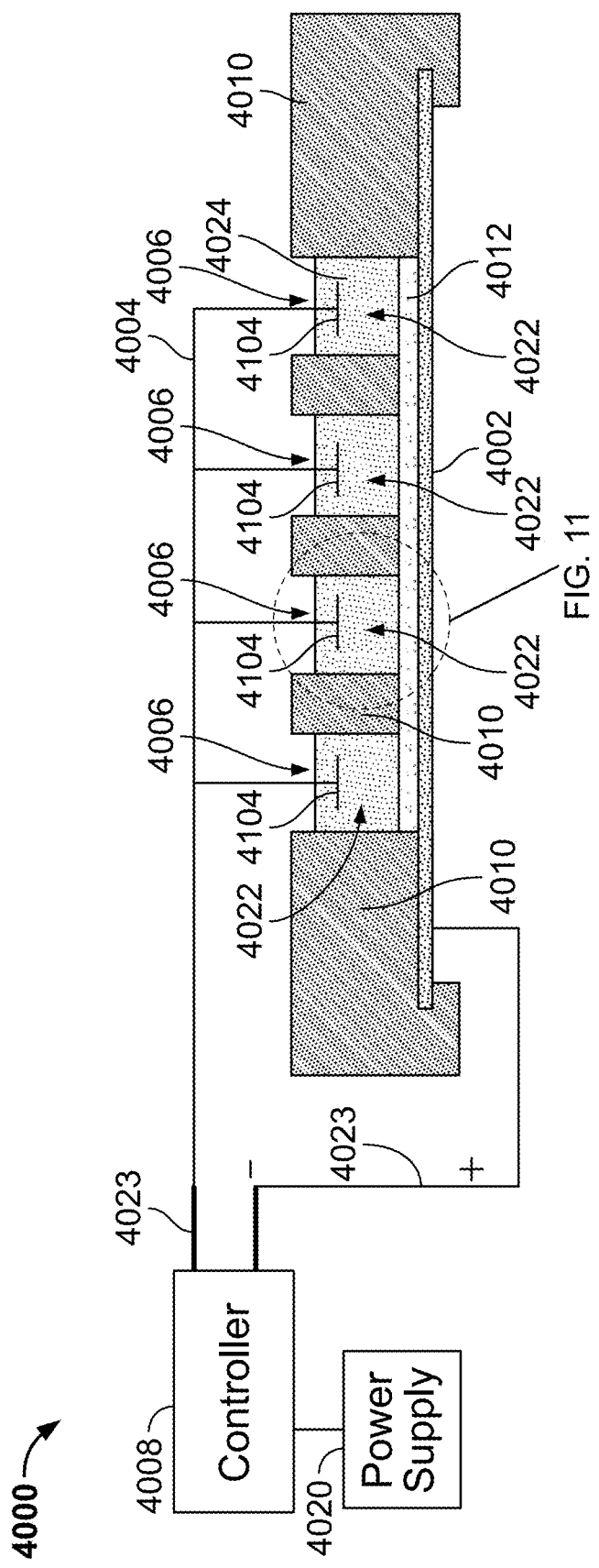
FIG. 5 schematically illustrates an example electrophoretic system.

Referring to FIGS. 5-12, another example electrophoretic system 4000 is described. FIG. 5 schematically illustrates an example configuration of the electrophoretic system 4000. In some implementations, the electrophoretic system 4000 can be used to provide electrophoretic permeabilization of a plurality of samples, and/or actively cause analytes in each sample to migrate to capture probes on a substrate. For example, electrophoretic permeabilization by the system 4000 can result in more analytes being captured by capture probes and better spatial fidelity of captured analytes (e.g., on a feature array) than random diffusion onto substrates without the application of an electric field.

In some implementations, the electrophoretic system 4000 can include a substrate 4002 as a first electrode, a second electrode 4004, a control system 4008, and a substrate cassette 4010.

Figure 6:
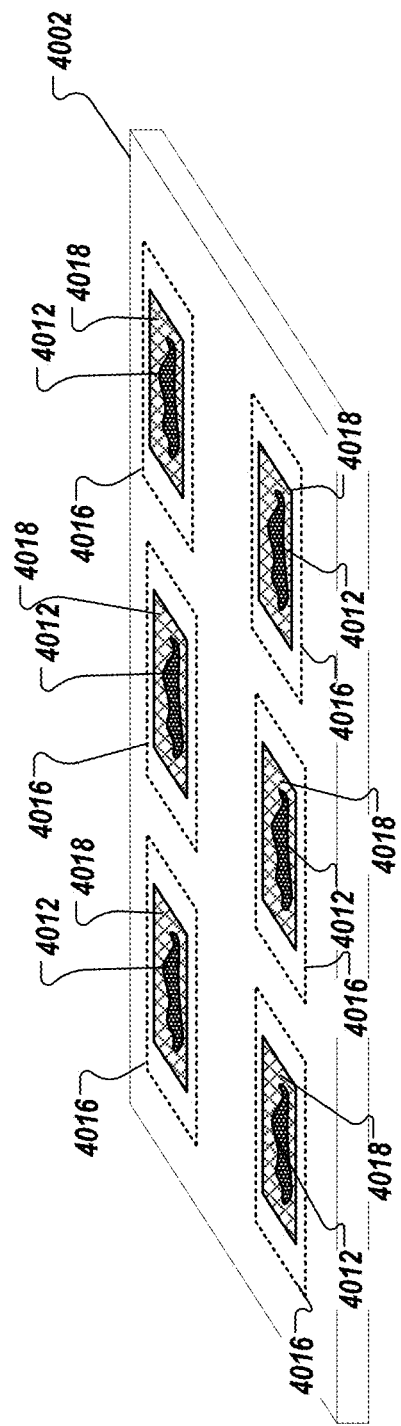
FIG. 6 schematically illustrates an example substrate.

Referring to FIG. 6, the substrate 4002 is configured to receive a plurality of samples 4012 that contain analytes. The samples 4012 can include biological samples 4012, such as a cell or a tissue including a cell. The substrate 4002 can include a plurality of substrate regions 4016 for receiving the sample 4012 thereon. In some implementations, the substrate 4002 a plurality of capture probes 4018 on each substrate region 4016. The capture probes 4018 can be placed on the substrate region 4016 in various manners, such as a variety of ways generally described herein. For example, the capture probes 4018 can be directly attached to a feature on an array. Alternatively or in addition, the capture probes 4018 can be immobilized on the substrate region 4016 of the substrate 4002. The sample 4012 can be prepared on the substrate 4002 in various ways generally described herein.

In some implementations, the substrate 4002 is configured to be used as a first electrode in the electrophoretic system 4000. For example, the substrate 4002 can be used as an anode. In another example, the substrate 4002 can be used as a cathode.

The substrate 4002 can be configured as a conductive substrate as described generally herein. For example, the substrate 4002 can include a conductive material that permits for the substrate 4002 to function as an electrode (e.g., the anode). Examples of such a conductive material include tin oxide (TO), indium tin oxide (ITO), a transparent conductive oxide (TCO), aluminum doped zinc oxide (AZO), fluorine doped tin oxide (FTO), and any combination thereof. Alternatively or in addition, other materials may be used to provide conductivity to the substrate 4002. In some implementations, the substrate 4002 can be coated with the conductive material. For example, the substrate 4002 can include a conductive coating on the surface thereof, and the sample 4012 is provided on the coating of the substrate 4002. Other examples of the substrate 4002 are further described below, for example with reference to FIG. 14.

Referring back to FIG. 5, the substrate cassette 4010 is configured to accommodate the substrate 4002. For example, the substrate cassette 4010 can be configured to immovably mount and hold the substrate 4002. The substrate cassette 4010 can include a plurality of apertures 4006. The plurality of apertures 4006 can be positioned in the substrate cassette 4110 so as to correspond to the plurality of substrate regions 4016 of the substrate 4002 when the substrate cassette 4010 mounts the substrate 4002. The plurality of apertures 4006 can define a plurality of buffer chambers 4022 on the plurality of substrate regions 4106 of the substrate 4002, respectively. The substrate cassette 4010 can be made of non-conductive material, such as plastic, glass, porcelain, rubber, etc.

Referring to FIGS. 7-10, an example substrate cassette 4190 is illustrated. The substrate cassette 4190 can be used to implement the substrate cassette 4010 in FIG. 5. The substrate cassette 4190 can include a substrate holder 4200 configured to hold a substrate.

Figure 7:
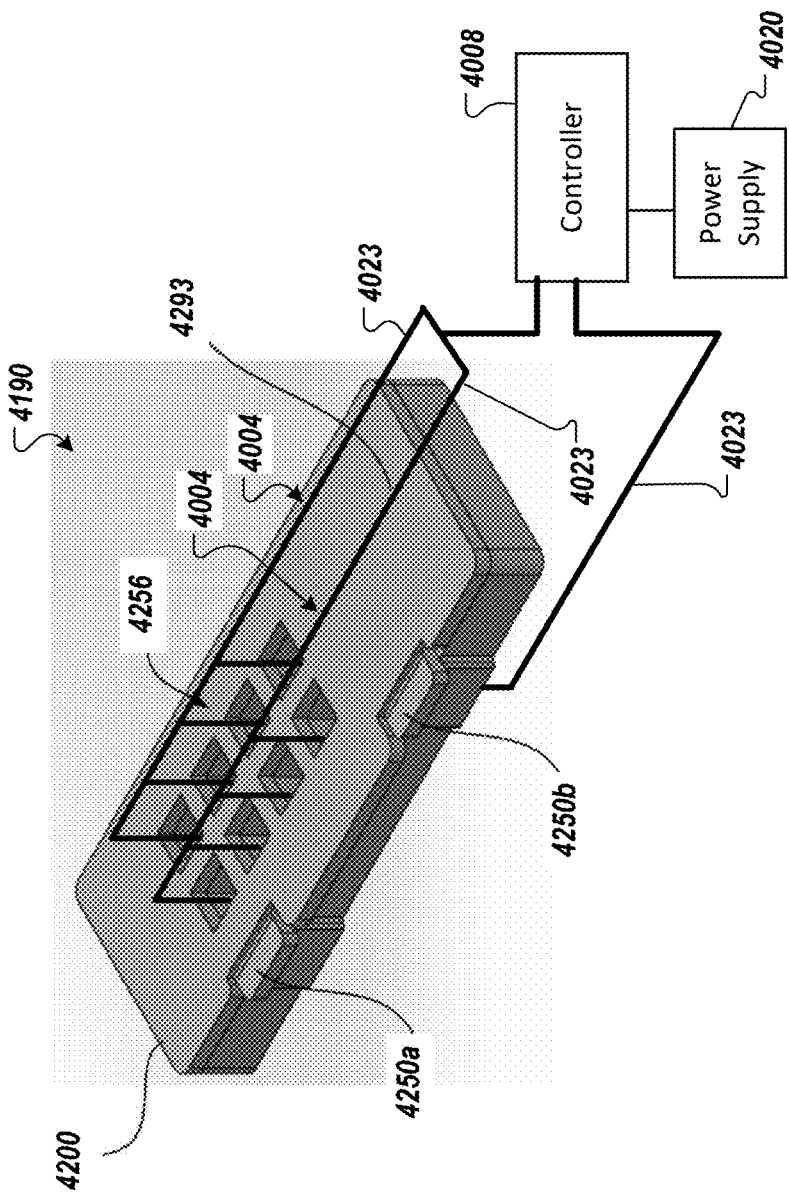
FIG. 7 shows an example substrate holder with a substrate in an assembled state.

FIG. 7 shows an example substrate holder 4200 with a substrate in an assembled state. This embodiment of the shown substrate holder 4200 can advantageously provide a single-piece component that can be arranged in an open configuration or closed configuration, when desired. In particular, FIG. 7 shows a top surface 4293 of the substrate holder 4200 in a closed position. The substrate holder 4200 includes a plurality of apertures 4256, which can be used to implement the plurality of apertures 4006 of the substrate cassette 4010 of FIG. 5.

The substrate holder 4200 can include a substrate loading mechanism for loading and holding the substrate. For example, the substrate loading mechanism can include a first tab 4250a and a second tab 4250b. In some embodiments, any type of fastener or engagement feature that allows releasable engagement can be used instead of the first and second tabs 4250a and 4250b, such as, for example, screws and press fit type connectors. In some embodiments, the substrate holder 4200 includes 5 tabs or less (e.g., 4 tabs or less, 3 tabs or less, 2 tabs or less, or 1 tab). In some embodiments, the substrate holder 4200 is a single molded unit. Any suitable plastic or polymer can be used as a suitable molding material.

In some embodiments, the substrate holder 4200 includes a substrate mount that has a first surface and a second surface, where the second surface of the substrate mount is configured to mount a substrate for receiving a sample. The substrate holder can include a first portion configured to receive a gasket. The first portion can include a plurality of ribs extending from a surface of the substrate holder. The substrate holder can include a second portion configured to receive a substrate. The first and second portions can be coupled together by a hinge. The first portion can be configured to fold over the second portion to secure the substrate between the first and second portions. In some embodiments, the substrate is a glass slide. In some embodiments, the substrate holder comprises a gasket disposed between the first portion and the second portion of the substrate holder. In some embodiments, the first portion of the substrate holder includes a releasable engagement mechanism configured to secure the first portion to the second portion when the substrate holder is in the closed state. In some embodiments, the first surface of the substrate engages with at least one of the plurality of ribs extending from a surface of the substrate holder. In some embodiments, the second portion defines a recessed cavity formed in the substrate holder configured to receive the substrate. In some embodiments, the second portion can define a cavity configured to receive the substrate.

Figure 8:
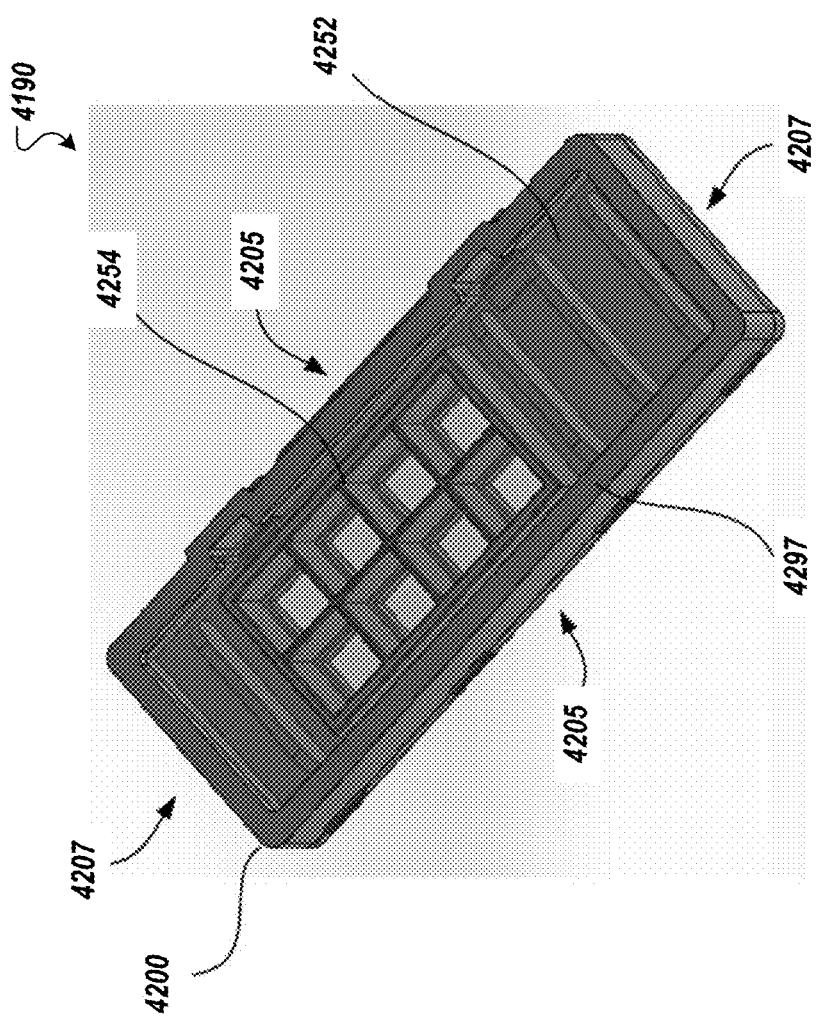
FIG. 8 shows a bottom surface of an example substrate holder including a gasket and receiving a substrate.

FIG. 8 shows the bottom surface 4297 of the top component of the substrate holder 4200 of the substrate cassette 4190, which includes a gasket 4254 and receiving a slide 4252 (e.g., the substrate). The substrate holder 4200 has longitudinal sides 4205 and latitudinal sides 4207. First and second tabs 4250a and 4250b (FIG. 9), respectively, can protrude from a longitudinal side 4205 of the substrate holder 4200. In some embodiments, the substrate holder 4200 is a single molded unit that includes the gasket 4254. That is, the substrate holder 4200 and the gasket 4254 are one part. In some embodiments, the substrate holder 4200 is overmolded with the gasket 4254. For example, the substrate holder 4200 is a first injection molded plastic part with a second part (e.g., a pliable material) molded onto it to create the gasket 4254. In some embodiments, the pliable material is an elastomer. In some embodiments, the pliable material is silicone rubber. In some embodiments, the gasket 4254 is a separate part that is not molded with the substrate holder 4200.

Figure 9A:
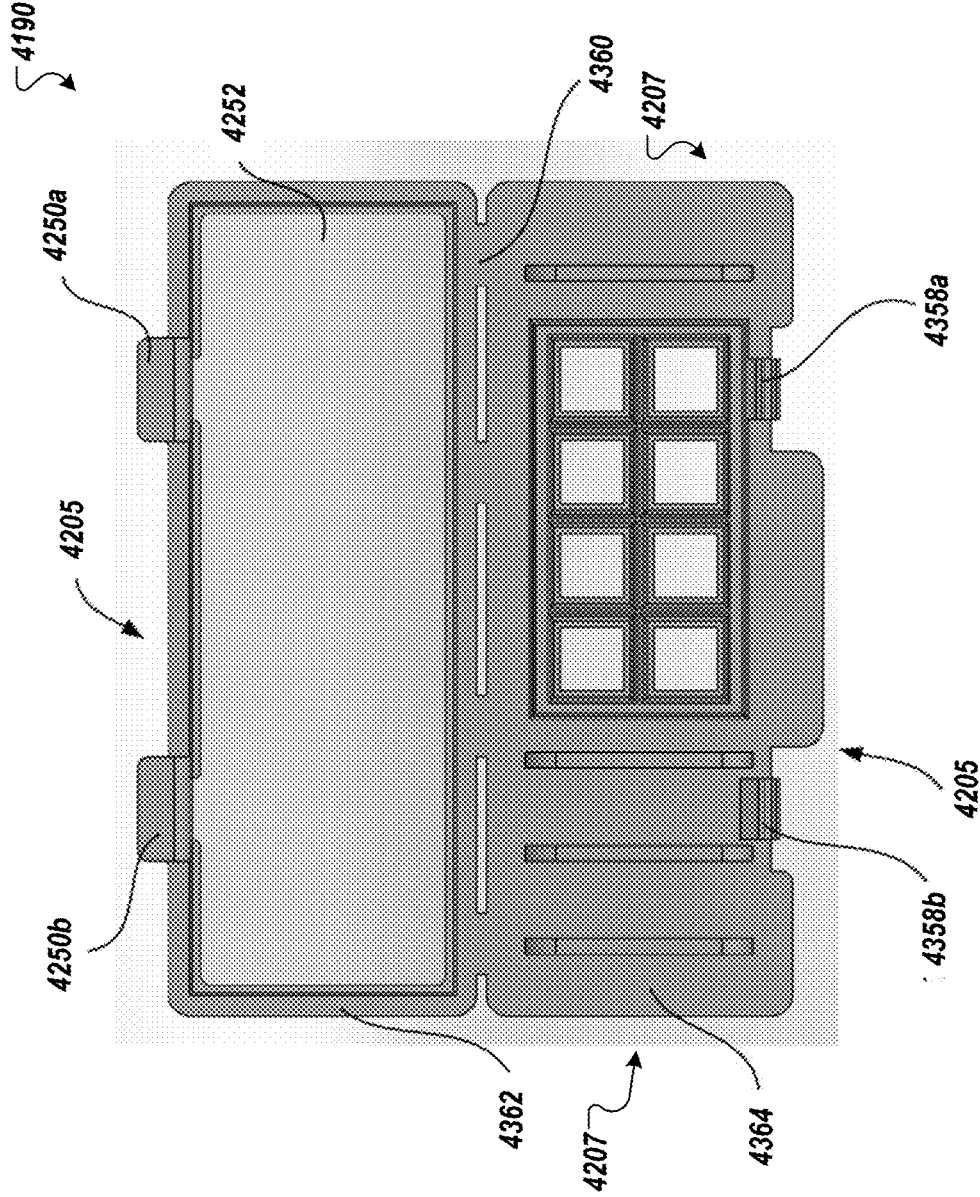
FIGS. 9A-C show A) a top view of an example substrate holder in an open position, B) a side view of a latitudinal side of the substrate holder and C) is a cross sectional view of the substrate holder.

FIG. 9A shows a top view of the substrate holder 4200 of the substrate cassette 4190 in an open position. The opening and closing mechanism of the substrate holder 4200 is a hinged mechanism. A bottom component 4362 of the substrate holder 4200 can be hinged to a top component 4364 of the substrate holder 4200 via a hinge 4360. In some embodiments, the hinge 4360 can be a living hinge. In some embodiments, the substrate holder 4200 includes 10 hinges or less (e.g., 9 hinges or less, 8 hinges or less, 7 hinges or less, 6 hinges or less, 5 hinges or less, 4 hinges or less, 3 hinges or less, 2 hinges or less, or 1 hinge). Non-limiting examples of hinges that the substrate holder 4200 can include, include a straight or flat living hinge, a butterfly living hinge, a child safe hinge, a double living hinge, and a triple living hinge.

The substrate holder 4200 further includes one or more engagement features, such as a first notch 4358a and a second notch 4358b. The first and second notches 4358a and 4358b can engage the first and second tabs 4250a and 4250b, respectively, when pressed together. The first and second notches 4358a and 4358b can protrude from a longitudinal side 4205 of the top component 4364 of the substrate holder 4200. In some embodiments, the substrate holder 4200 includes three, four, five, six, seven, eight, nine, ten or more notches. In some embodiments, the notches protrude from a latitudinal side 4207 of the substrate holder 4200. In some embodiments, the first and second notches 4358a and 4358b are rigid and do not flex when engaging the first and second tabs 4250a and 4250b, respectively. In some embodiments, the first and second notches 4358a and 4358b, respectively, can be flexible.

Figure 9B:
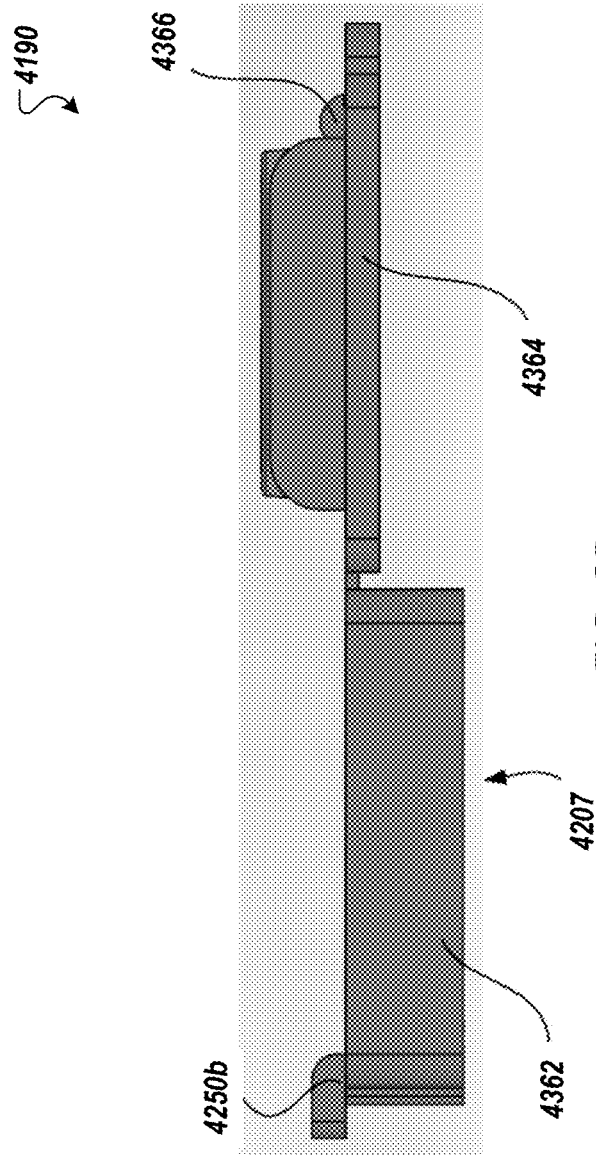
Figure 9C:
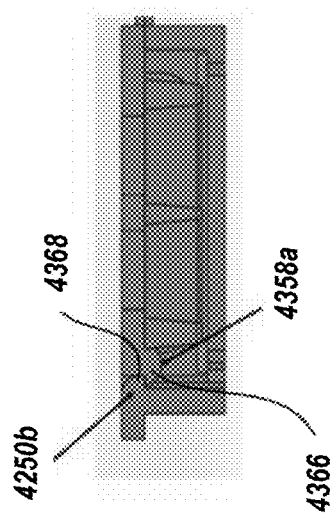

FIG. 9B shows a side view of a latitudinal side 4207 of the substrate cassette 4190. The first and second notches 4358a and 4358b can project upward and include a notch ledge 4366 that engages a tab ledge 4368, as shown in FIG. 9C. Alternatively, in some embodiments, the substrate holder 4200 includes a snap fit locking mechanism for releasably receiving and releasably securing the slide 4252. Non-limiting examples of other types of fasteners to be used in locking mechanisms of the substrate holder 4200 include a catch, a projection, a male connector, and a female connector.

Figure 10A:
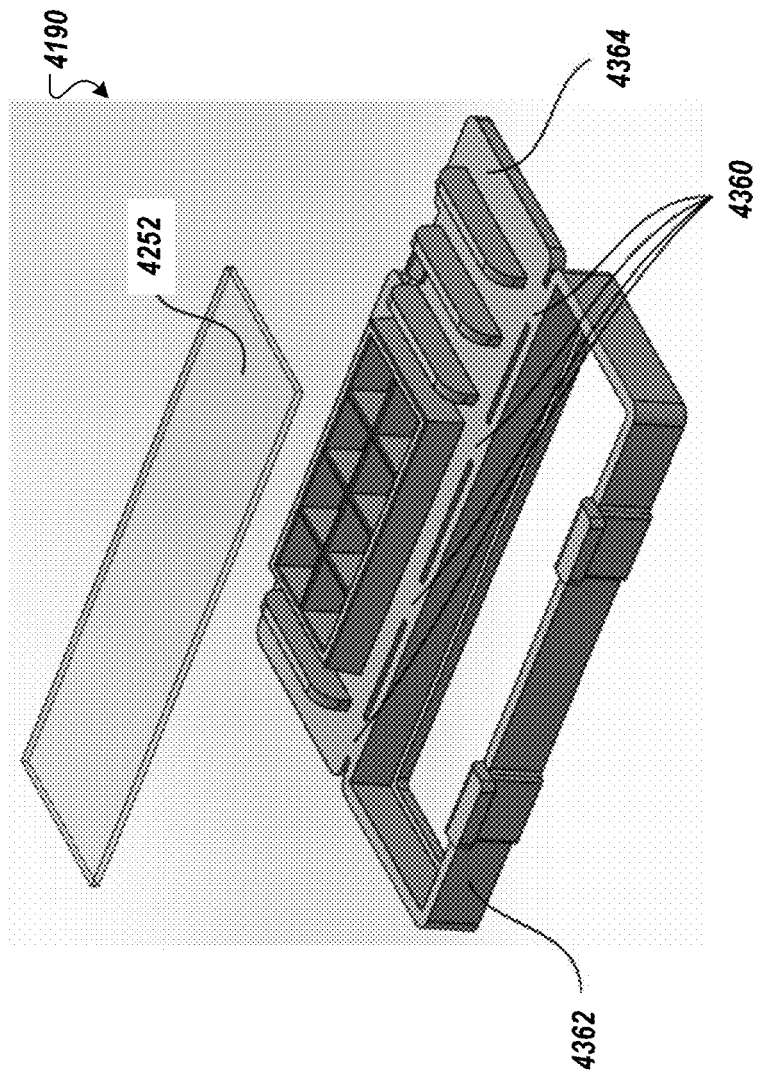
FIGS. 10A and B illustrate an example placement of a substrate into the substrate holder.
Figure 10B:
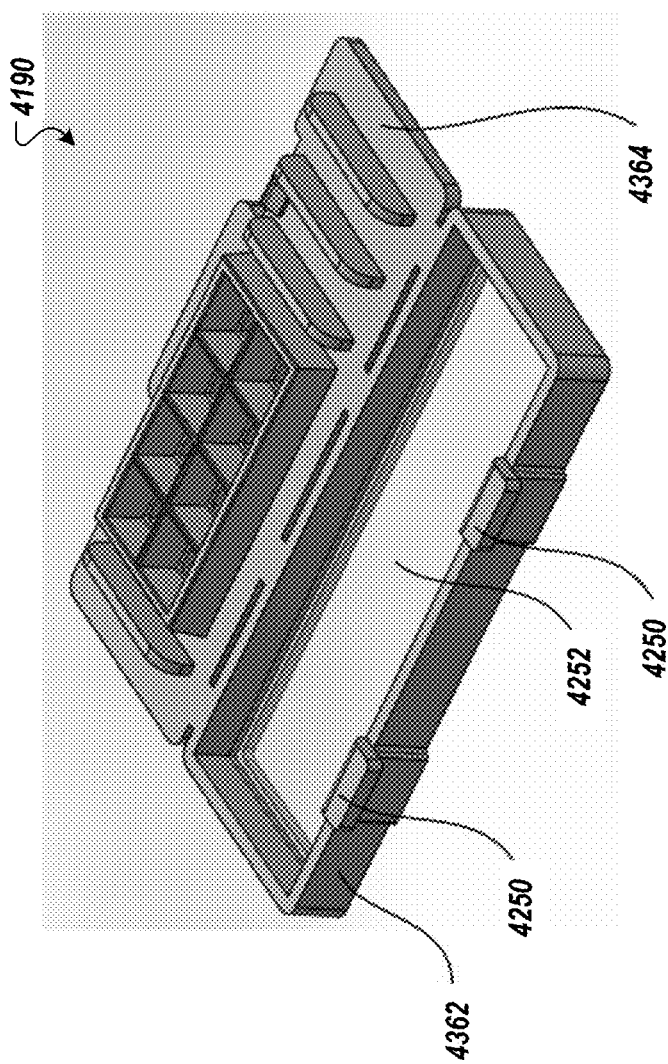

FIGS. 10A and B illustrate the placement of the slide 4252 into the substrate holder 4200 of the substrate cassette 4190. In some embodiments, the slide 4252 can be "loaded" or placed onto an inner rim or an inner edge of the bottom component 4362 of substrate holder 4200. Once loaded, the top component 4364 is closed by pressing the first notch 4358a and the second notch 4358b against the first and second tabs 4250a and 4250b, respectively, thereby forming a tight seal with the slide 4252. In some embodiments, the slide does not have to be tilted under tabs 4250 or any other tabs. In some embodiments, the substrate holder 4200 includes one or more tabs to help load the slide onto the inner rim or inner edge of the bottom component 4362 of substrate holder 4200.

Figure 15A:
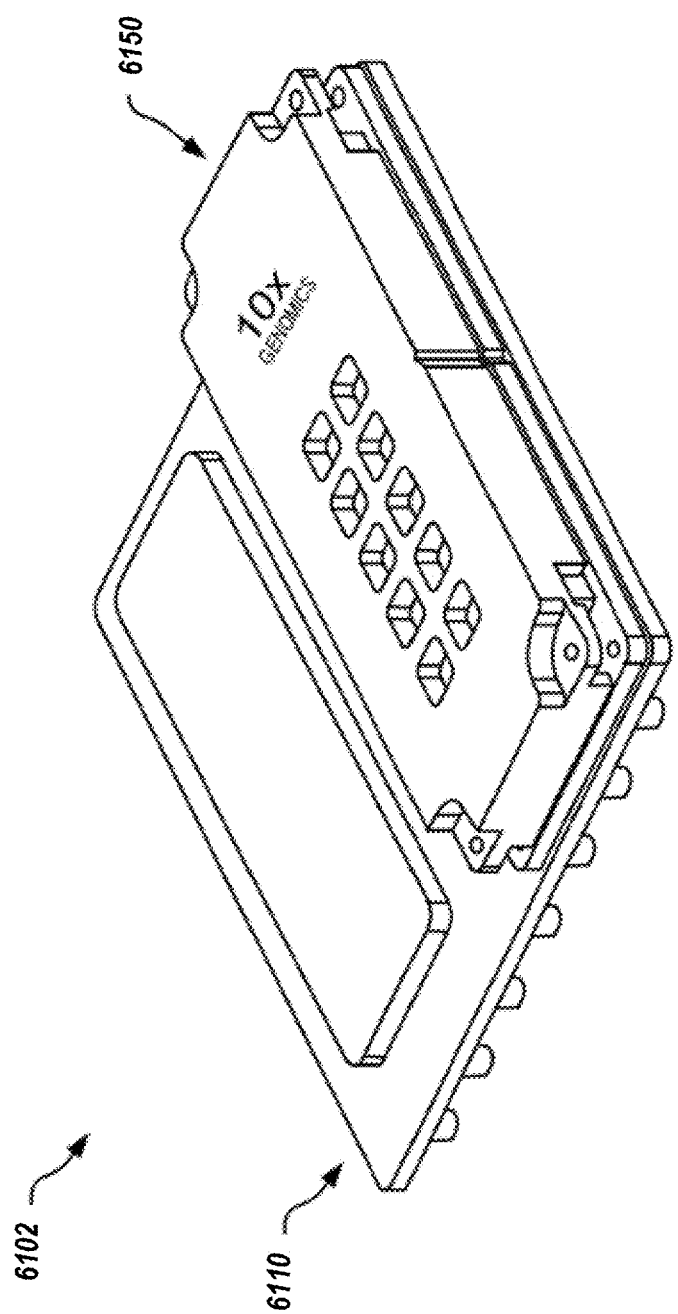
FIGS. 15A-C are A) a perspective view of an example device including a plate and a substrate holder for heating a substrate, B) top perspective view of the plate, and C) a bottom perspective view of the plate.

A variety of other configurations of substrate holder can be used to implement the substrate cassette 4010 in FIG. 5. Examples of such other configurations are further illustrated below, for example with reference to FIG. 15.

Referring back to FIG. 5, the substrate 4002 is used as the anode, and the second electrode 4004 is configured as a cathode. In this example, therefore, the second electrode 4004 can also be referred to as the cathode 4004. In some implementations, the cathode 4004 can include a conductive plate, one or more pins, or other suitable configurations. As illustrated, for example, the cathode 4004 can include a plurality of electrode plates 4104. The electrode plates 4104 are configured to be positioned within the plurality of buffer chambers 4022 of the substrate cassette 4010, respectively.

The samples 4012 on the substrate regions 4016 of the substrate 4002, respectively, can be arranged within the buffer chambers 4022 that are defined by the apertures 4006 of the substrate cassette 4010. The buffer chambers 4022 can contain buffers 4024 therein, so that the samples 4012 are fully immersed into the buffers 4024 in the buffer chambers 4022, respectively. Further, as illustrated in FIGS. 5 and 7, the electrode plates 4104 of the cathode 4004 can be arranged within the buffer chambers 4022, respectively.

Each of the electrode plates 4104 can be immersed into a buffer 4024 contained in the buffer chamber 4022. The electrode plates 4104 are arranged to be spaced apart from the corresponding substrate regions 4016 of the substrate 4002.

The buffer 4024 can be of various types. In some implementations, the buffer 4024 includes a permeabilization reagent. Alternatively or in addition, other type of buffers as generally described herein can be used. The buffer 4024 is contained in each of the buffer chambers 4022 throughout the electrophoretic process.

The controller 4008 operates to generate an electric field (−E) between the substrate (anode) 4002 and the cathode 4004. For example, the controller 4008 operates to generate an electric field between the substrate regions 4016 of the substrate 4002 and the electrode plates 4104 of the cathode 4004 that correspond to the substrate regions 4016, respectively. Thus, the electric field is generated through each of the buffer chambers 4022. In some implementations, the same electric field is generated for all of the buffer chambers 4022. In other implementations, different electric fields are generated for at least two of the buffer chambers 4022.

In some implementations, the controller 4008 can operate to apply a voltage between the entire substrate 4002 and the entire cathode 4004 using a power supply 4020. In other implementations, the controller 4008 can operate to apply voltages between the substrate regions 4016 of the substrate 4002 and the corresponding electrode plates 4104 of the cathode 4004, respectively. The power supply 4020 can include a high voltage power supply. The controller 4008 can be electrically connected to the substrate 4002 and the cathode 4004 using electrical wires 4023.

Figure 11:
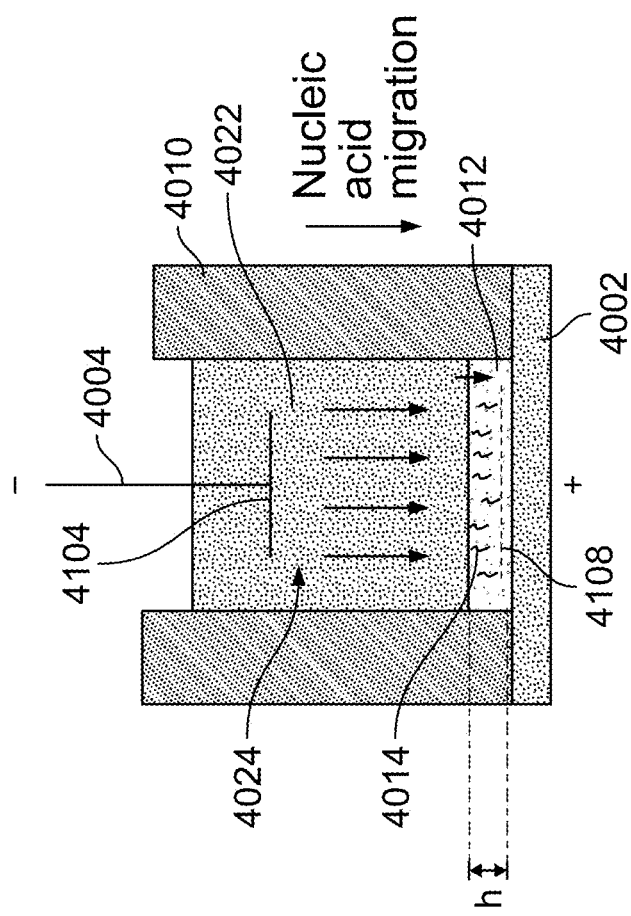
FIG. 11 schematically illustrates an example configuration of a substrate region and a sample undergoing electrophoretic process in each buffer chamber.

FIG. 11 schematically illustrates an example configuration of a substrate region and a sample undergoing electrophoretic process in each buffer chamber of the electrophoretic system 4000. In each buffer chamber 4022, the analytes 4014 in the sample 4012 can migrate toward the capture probes 4018 under the electric field (−E).

The application of electric field (−E) can cause the analytes 4014 (e.g., negatively charged analytes) to move towards the capture probes 4018 (e.g., positively charged analytes) in the direction of the arrow shown. In some implementations, the analytes 4014 include a protein or a nucleic acid. In some embodiments, the analytes 4014 are negatively charged proteins or nucleic acids. In some embodiments, the analytes 4014 include a positively charged protein or a nucleic acid. In some embodiments, the analytes 4014 includes a negatively charged transcript. For example, the analytes 4014 include a polyA transcript. In some embodiments, the capture probes 4018 are affixed on the substrate 4002 at the substrate regions 4016 of the substrate 4002. In some embodiments, the capture probes 4018 are location at a feature on the array, or can be replaced at a feature on the array. In some embodiments, the analytes 4014 move towards the capture probes 4018 for a distance (h). In some embodiments, the buffer 4024 (e.g., comprising a permeabilization reagent) can be in contact with the sample 4012, the substrate 4002 (e.g., the substrate region 4016 thereof), the cathode 4004 (e.g., the electrode plates 4104 thereof), or any combination thereof. The buffer 4024 can include any of the permeabilization reagents disclosed including but not limited to a permeabilization reagent such as a permeabilization enzyme, a permeabilization buffer, a buffer without a permeabilization reagent, a permeabilization gel, and a permeabilization solution.

In other implementations, the electrophoretic system 4000 can be configured to provide different configurations in the buffer chambers 4024, using, for example, those described in FIG. 3 above.

Figure 12:
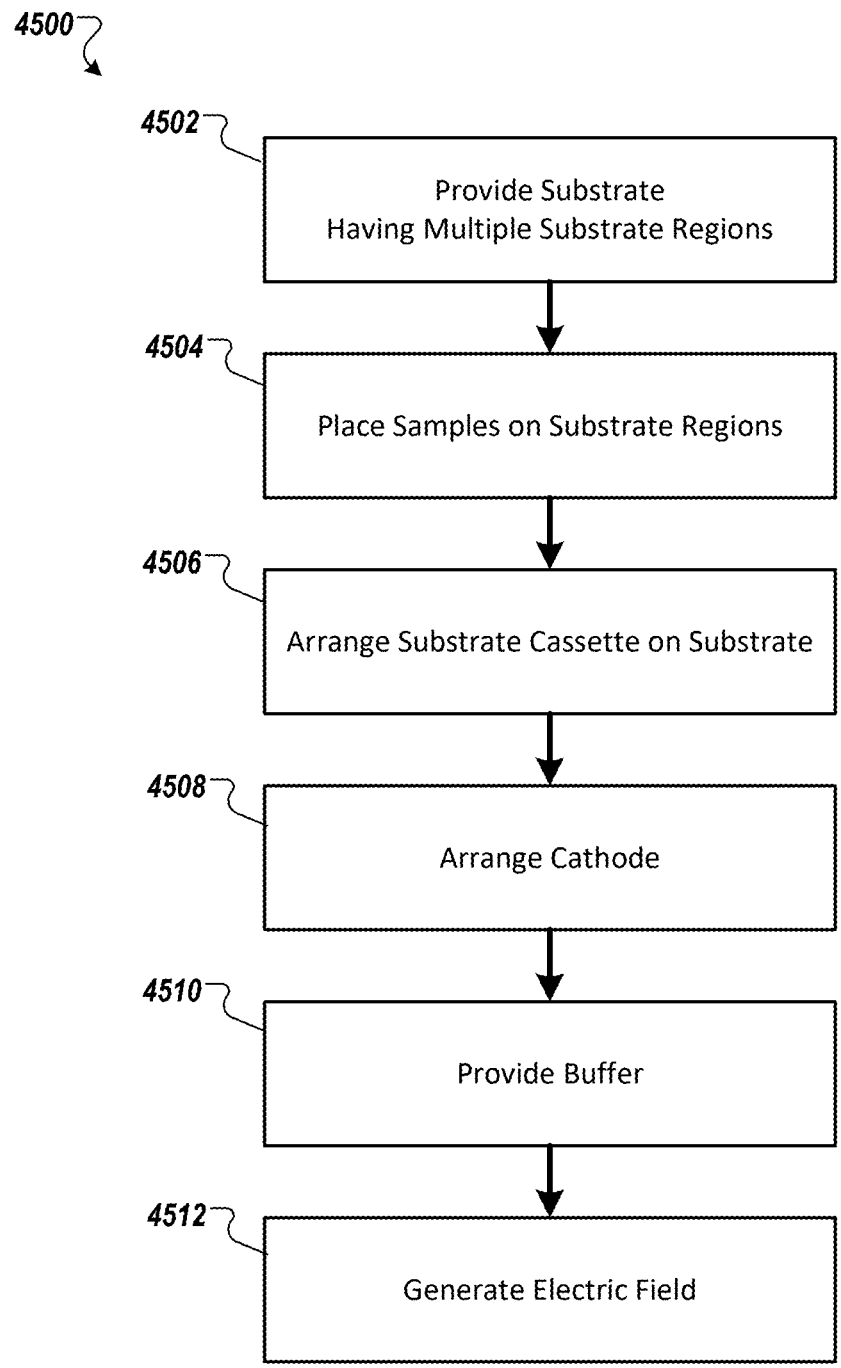
FIG. 12 is a flowchart of an example process for preparing a sample.

FIG. 12 is a flowchart of an example process 4500 for preparing a sample. In some implementations, the process 4500 includes providing a substrate including a plurality of substrate regions (4502). Each substrate region of the substrate can include a plurality of capture probes. The process 4500 can include placing multiple samples in contact with the capture probes on the substrate regions of the substrate (4504), for example, when there are two substrate regions one sample is contacted to each region, when there are three regions, there are three samples (one on each region), etc. The capture probes can be attached to the substrate regions in various ways described herein. The sample can be placed on the substrate region in various ways described herein.

The substrate can be configured and used as an electrophoretic electrode (also referred to herein as a first electrode). In some implementations, the substrate can be configured as a conductive substrate as described herein, such as by including a conductive material in the substrate or providing a conductive coating on an upper or lower surface of the substrate. In some implementations, the substrate can be used as an anode. In alternative implementations, the substrate can be used as a cathode.

Alternatively, the substrate can be configured and used such that each substrate region operates as an electrophoretic electrode (also referred to herein as a first electrode), while the other portion (e.g., at least a portion around each conductive substrate region) is non-conductive. In some implementations, each substrate region can be configured as a conductive region, such as by including a conductive material in the substrate region or providing a conductive coating on an upper or lower surface of the substrate region. In some implementations, each substrate region can be used as an anode. In alternative implementations, each substrate region can be used as a cathode.

The process 4500 can further include arranging a substrate cassette on or above the substrate (4506). The substrate cassette can be arranged such that a plurality of apertures of the substrate cassette are aligned with the substrate regions of the substrate, respectively, thereby defining a plurality of buffer chambers on the plurality of substrate regions. As described herein, the substrate cassette can be at least partially made of a non-conductive material and used to provide the buffer chambers between the first and second electrodes.

The process 4500 can include arranging a second electrode relative to the first electrode (e.g., the substrate or each substrate region) at a distance (4508). The second electrode can be used as a cathode when the substrate or each substrate region is used as an anode. Alternatively, the second electrode can be used as an anode when the substrate or each substrate region is used as a cathode. The second electrode can be made of various configurations. For example, the second electrode can include a plurality of electrode plates configured to be placed within the buffer chambers, respectively.

The process 4500 can include providing a buffer between the first electrode (e.g., the substrate or each substrate region) and the second electrode (e.g., each electrode plate) (4510). The buffer can be contained in each buffer chamber that is provided by the substrate cassette and used to at least partially immerse the first electrode (e.g., the substrate or each substrate region), the second electrode (e.g., each electrode plate), or both. In some implementations, the buffer can include a permeabilization reagent.

The process 4500 can include generating an electric field between the first electrode (e.g., the substrate or each substrate region) and the second electrode (e.g., each electrode plate) (4512). Under the electric field, analytes included in the sample can migrate toward the capture probes on each substrate region, for example in order to hybridize (e.g., captured) to the capture probe. In some implementations, the electric field is generated by applying a voltage between the first and second electrodes, using a power supply electrically connected to the first and second electrodes. For example, the process 4500 can include connecting electrical wires from the power supply with the first electrode (e.g., the substrate or each substrate region) and the second electrode (e.g., each electrode plate).

Figure 13:
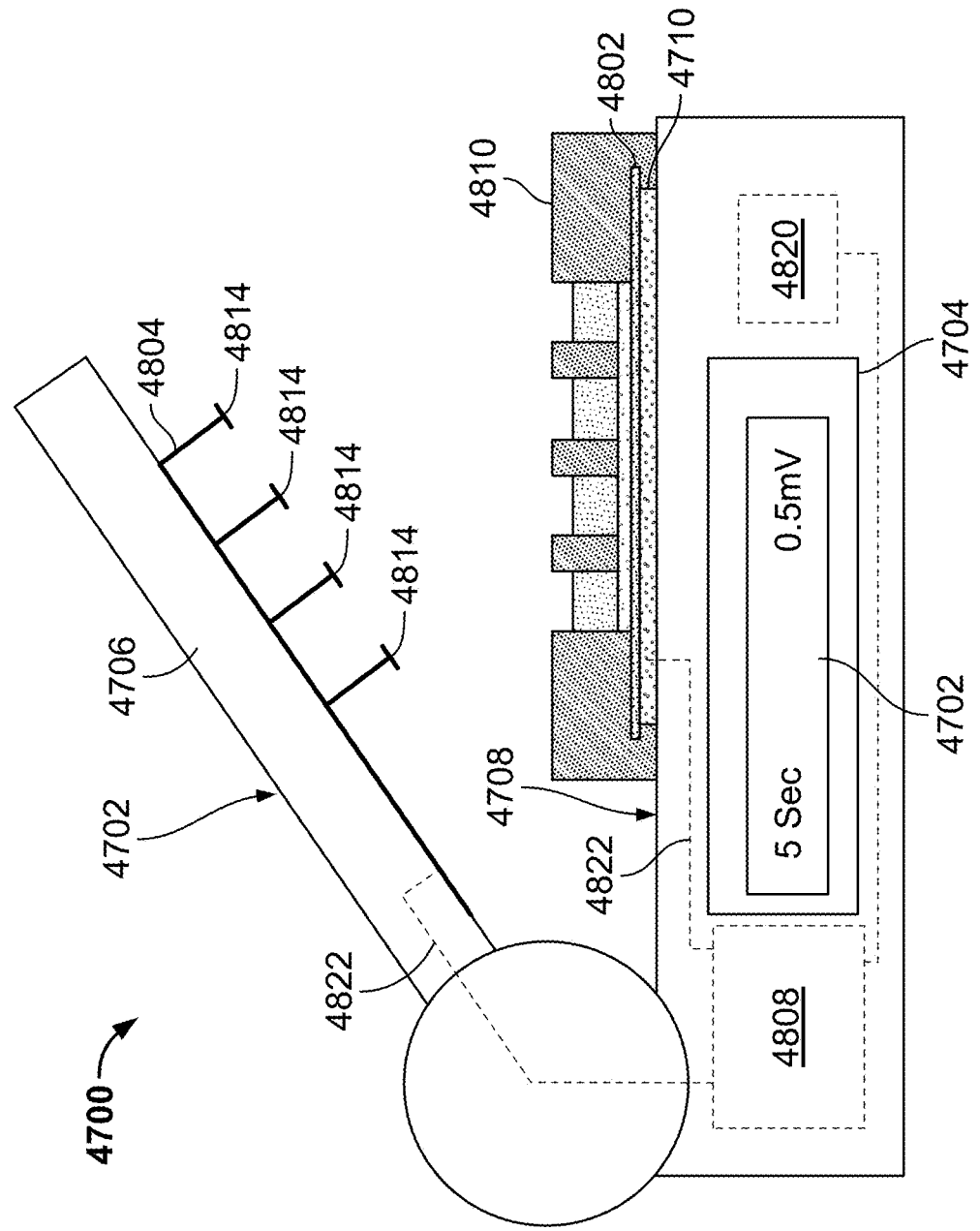
FIG. 13 schematically illustrates an example system for preparing a sample.

FIG. 13 schematically illustrates an example system 4700 for preparing a sample. The system 4700 can include a sample preparation instrument 4702, a substrate 4802 as a first electrode, a second electrode 4804, a control system 4808, and a substrate cassette 4810.

The sample preparation instrument 4702 is configured to support the substrate cassette 4810 with the substrate 4802, and provide the second electrode 4804 to generate an electric field between the substrate 4802 and the second electrode 4804. In some implementations, the sample preparation instrument 4702 includes a body 4704 and a lid 4706 configured to be place over the body 4704. For example, the lid 4706 is hingedly connected to the body 4704. Alternatively, the lid 4706 can be coupled to the body 4704 in other configurations. In yet alternative implementations, the lid 4706 is configured to be separate from the body 4704, or detachably attached to the body 4704.

In some implementations, the body 4704 provides a supporting surface 4708 configured to support the substrate cassette 4810 including the substrate 4802. The body 4704 further provides an electrical connector 4710 for electrically contacting the substrate 4802 so that the substrate 4802 can be used as an electrode (e.g., an anode) for electrophoresis. The substrate 4802 and the substrate cassette 4810 can be configured identically or similarly to the substrate 4002 and the substrate 4010, respectively. For example, the substrate 4802 includes a plurality of substrate regions that include capture probes configured to place samples thereon. The substrate cassette 4810 includes a plurality of apertures that correspond to the plurality of substrate regions and define a plurality of buffer chambers.

The lid 4706 can be configured to mount the second electrode 4804 (e.g., a cathode). The second electrode 4804 can be configured similarly to the second electrode 4004. For example, the second electrode 4804 can include a plurality of electrode plates 4814 corresponding to the buffer chambers on the substrate 4802. The second electrode 4804 is arranged such that, when the lid 4706 is closed onto the body 4704, or comes close to the body 4704, the electrode plates 4814 of the second electrode 4004 are at least partially inserted into the buffer chambers of the substrate cassette 4810.

The sample preparation instrument 4702 can include the control system 4808 that is identical or similar to the controller 4008. For example, the control system 4808 can be housed in the body 4704. Alternatively, at least part of the control system 4808 can be housed in or mounted to another part of the instrument, such as the lid 4706. Alternatively, the control system 4808 can be at least partially configured as a separate apparatus from the instrument 4702 and electrically connected to the instrument 4702. The control system 4808 can be electrically connected to the substrate 4802 (or each substrate region thereof) and the second electrode 4804 (or each electrode plate thereof) using electrical wires 4822.

The sample preparation instrument 4702 can further include a power supply 4820 configured to apply a voltage between the substrate 4802 (or each substrate region thereof) and the second electrode 4804 (or each electrode plate thereof). The power supply 4820 can be housed in the body 4704. Alternatively, the power supply 4820 can be housed in or mounted to another part of the instrument, such as the lid 4706. Alternatively, the power supply 4820 can be provided separately from the instrument 4702.

In some implementations, the sample preparation instrument 4702 can be configured to automatically start electrophoresis when the lid 4706 is closed over the body 4704, or lowered to a predetermined position (or angle) over the samples, and stop electrophoresis when the lid 4706 returns to be opened or raised from the predetermined position. Alternatively, the sample preparation instrument 4702 can provide a user interface 4720 (e.g., a button, switch, etc.) to receive a manual input of starting or stopping the electrophoretic process. The user interface 4720 can include an output device, such as a display, lamps, etc., configured to output operating parameters of the instrument 4702 (e.g., a voltage being applied, a duration of such application, etc.) or other information associated with the system 4700. The user interface 4720 can further include an input device, such as physical or virtual buttons, switches, keypads, etc., configured to receive a user input of adjusting the operating parameters of the instrument 4702 or other information associated with the system 4700.

Figure 14:
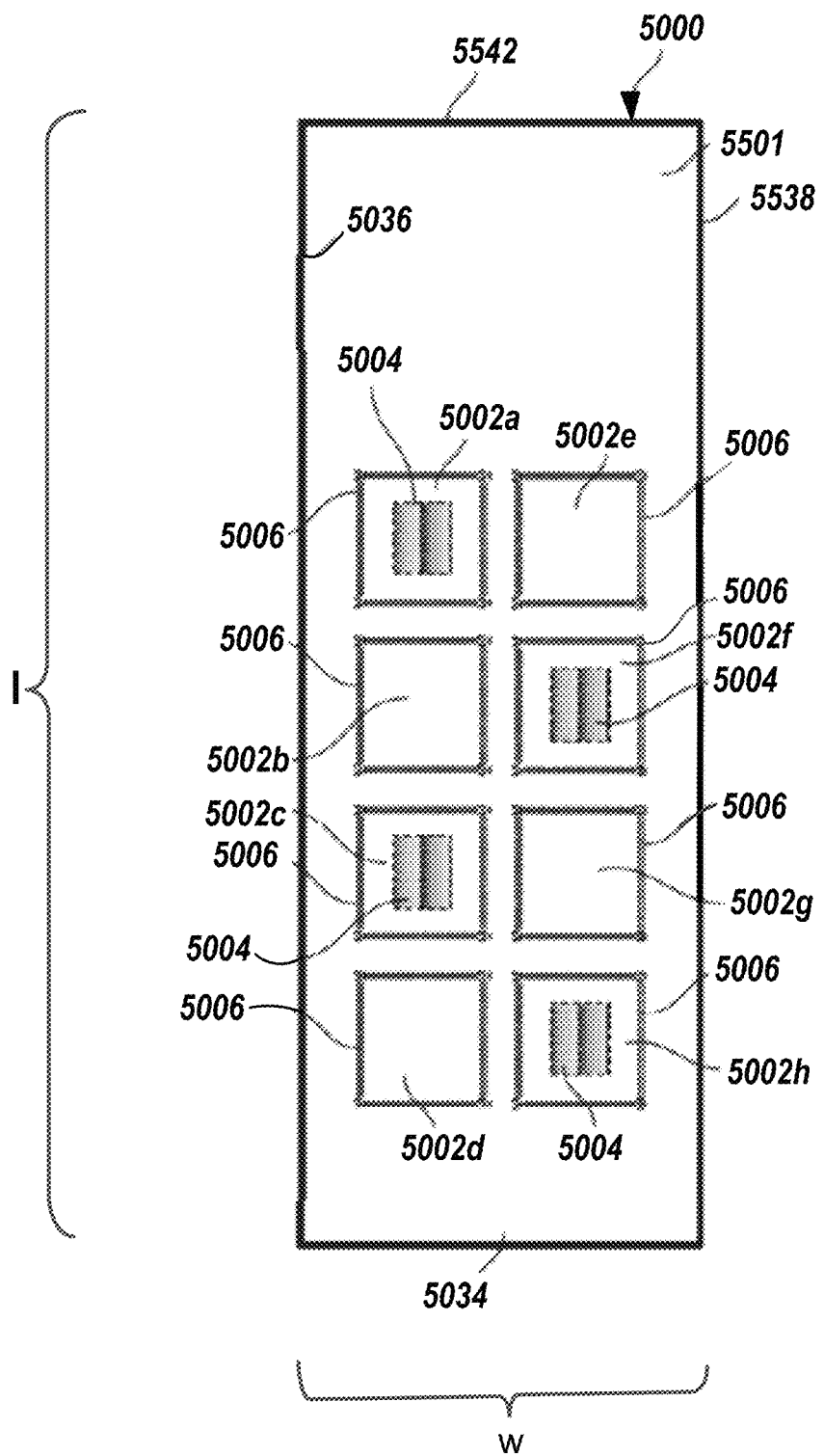
FIG. 14 illustrates another example substrate.

Referring to FIG. 14, another example substrate 5000 is described. The substrate 5000 can be used to implement the substrates 4002, and 4802 described herein. The substrate 5000 has a surface 5501 that includes substrate regions 5002*a-h*. The substrate 5000 can include a first substrate region 5002*a*, a second substrate region 5002*b*, a third substrate region 5002*c*, a fourth substrate region 5002*d*, a fifth substrate region 5002*e*, a sixth substrate region 5002*f*, a seventh substrate region 5002*g*, and an eighth substrate region 5002*h*. In some embodiments, substrate 5000 can have less than eight substrate regions or more than eight substrate regions. Each substrate region can be enclosed within a defined perimeter of a frame 5006, for example a frame comprising fiducial markers.

In some implementations, the eight substrate regions 5002*a-h* can be positioned at the center of the substrate 5000. For example, the eight substrate regions 5002*a-h* can be centered on the substrate 5000 such that a first distance extending from an outer edge of a frame 5006 of one of the first substrate region 5002*a*, second substrate region 5002*b*, third substrate region 5002*c*, or fourth substrate region 5002*d* to a longitudinal edge (i.e., along length l) of the substrate 5000 is substantially the same to a second distance extending from an outer edge of a frame 5006 of one of the fifth substrate region 5002*e*, sixth substrate region 5002*f*, seventh substrate region 5002*g*, or eighth substrate region 5002*h* to a longitudinal edge (i.e., along length l) of substrate 5000. For example, the substrate arrays can be positioned about 28.5 mm from the top edge 5032 of substrate, about 11.25 mm from the bottom edge 5034 of substrate, and about 3.5 mm from the left edge 5036 and right edge 5038 of substrate, when the substrate is oriented vertically as is shown in FIG. 14.

In some embodiments, the eight substrate regions 5002*a-h* can be centered on the substrate 5000 such that a first distance extending from an outer edge of a frame 5006 of one of the first substrate region 5002*a*, second substrate region 5002*b*, third substrate region 5002*c*, or fourth substrate region 5002*d* to a latitudinal edge (i.e., along width w) of the substrate 5000 is substantially the same to a second distance extending from an outer edge of a frame 5006 of one of the fifth substrate region 5002*e*, sixth substrate region 5002*f*, seventh substrate region 5002*g*, or eighth substrate region 5002*h* to a longitudinal edge (i.e., along width w) of the substrate 5000.

In some embodiments, the substrate 5000 can be rectangular in shape. In some embodiments, the substrate 5000 has a length l of about 100 mm to about 10 mm (e.g., 90 mm or less, 85 mm or less, 90 mm or less, 75 mm or less, 70 mm or less, 65 mm or less, 60 mm or less, 55 mm or less, 50 mm or less, 45 mm or less, 40 mm or less, 35 mm or less, 30 mm or less, 25 mm or less, 20 mm or less, 15 mm or less). In some embodiments, the substrate 5000 has a width w of about 100 mm to about 10 mm (e.g., 90 mm or less, 85 mm or less, 90 mm or less, 75 mm or less, 70 mm or less, 65 mm or less, 60 mm or less, 55 mm or less, 50 mm or less, 45 mm or less, 40 mm or less, 35 mm or less, 30 mm or less, 25 mm or less, 20 mm or less, 15 mm or less). In some embodiments, substrates of the disclosure can be square or circular in shape. In some embodiments, substrates of the disclosure can be rectangular, triangular, hexagonal, octagonal, pentagonal, or any other suitable two-dimensional, geometric shape.

In some embodiments, the substrate 5000 includes 1, 2, 3, 4, 5, 6, 7, 8, 9, 10 or more substrate arrays. The substrate 5000 includes four substrate arrays 5004, as shown in FIG. 14. The substrate 5000 can include a substrate array 5004 arranged within the frame 5006. For example, the substrate array 5004 can be positioned at the center of a frame 5006. In some embodiments, the substrate arrays 5004 can be the same (e.g., can have a same pattern). In some embodiments, the substrate arrays 5004 can be the different (e.g., can have a different pattern). The four substrate arrays 5004, shown in FIG. 14, can be repeated and arranged in a checked pattern. That is, substrate array 5004 is positioned at the center of the first substrate region 5002*a*, the third substrate region 5002*c*, the sixth substrate region 5002*f*, and the eighth substrate region 5002*h*. In some embodiments, the checked pattern is meant to occupy as much of the surface of the substrate to ensure consistency of image acquisition when scanning different regions of the substrate.

In some embodiments, the substrate regions 5002*a-h* can be arranged vertically in two columns, as shown in FIG. 14. In some embodiments, the substrate regions are arranged on the substrate in one column. In some embodiments, the substrate regions are arranged on the substrate in 2, 3, 4, 5, 6, 7, 8, 9, 10, or more columns. In some embodiments, the substrate arrays 5004 can be positioned adjacent to each other. For example, in some embodiments, the substrate arrays 5004 can be arranged vertically in a column (e.g., positioned on the first four substrate regions 5002*a*-2402*d*). Alternatively, in other embodiments, the substrate arrays 5004 can be positioned on the substrate regions 5002*a*, 5002*b*, 5002*e*, and 5002*f*. In some embodiments, the substrate arrays 5004 can be positioned on the substrate regions 5002*e*, 5002*f*, 5002*g*, and 5002*h*. In some embodiments, the substrate arrays 5004 can be positioned on the substrate regions 5002*c*, 5002*d*, 5002*e*, and 5002*h*. In some embodiments, the substrate arrays 5004 can be positioned on the substrate regions 5002*e*, 5002*b*, 5002*g*, and 5002*d*. In some embodiments, the substrate arrays 5004 are not arranged in a particular pattern. In some embodiments, the substrate arrays 5004 vary individually in size. For example, in some embodiments, a first substrate array may have a greater size than the size of a second substrate array. In some embodiments, a first substrate array may have a smaller size than the size of a second substrate array. In some embodiments, the distance between substrate arrays may vary and be different. For example, in some embodiments, the distance between a first substrate array and a second substrate array may be different than the distance between a third substrate array and a fourth substrate array. In various embodiments, the substrate 5000 can have eight substrate arrays 5004 or less (e.g., 7 substrate arrays or less, 6 substrate arrays or less, 5 substrate arrays or less, 4 substrate arrays or less, 3 substrate arrays or less, 2 substrate arrays or less). In some embodiments, the substrate arrays are arranged on the substrate in one column. In some embodiments, the substrate arrays are arranged on the substrate in 2, 3, 4, 5, 6, 7, 8, 9, 10, or more columns.

Referring to FIGS. 15-22, an example substrate cassette is described. In some implementations, an example system 6102 is configured to heat a substrate and includes a plate 6110 and a substrate holder 6150. The substrate holder 6150 can be used to replace the substrate cassette 4010, 4810 described herein. The plate 6110 can be configured to be received by a heating device (e.g., a thermocycler) and provide heat transfer between the heating device and the substrate holder 6150. The substrate holder 6150 holds one or more substrates (such as one or more microscope slides), and can removably couple to the plate 6110 to facilitate heat transfer from the plate 6110 to the one or more substrates.

Figure 15B:
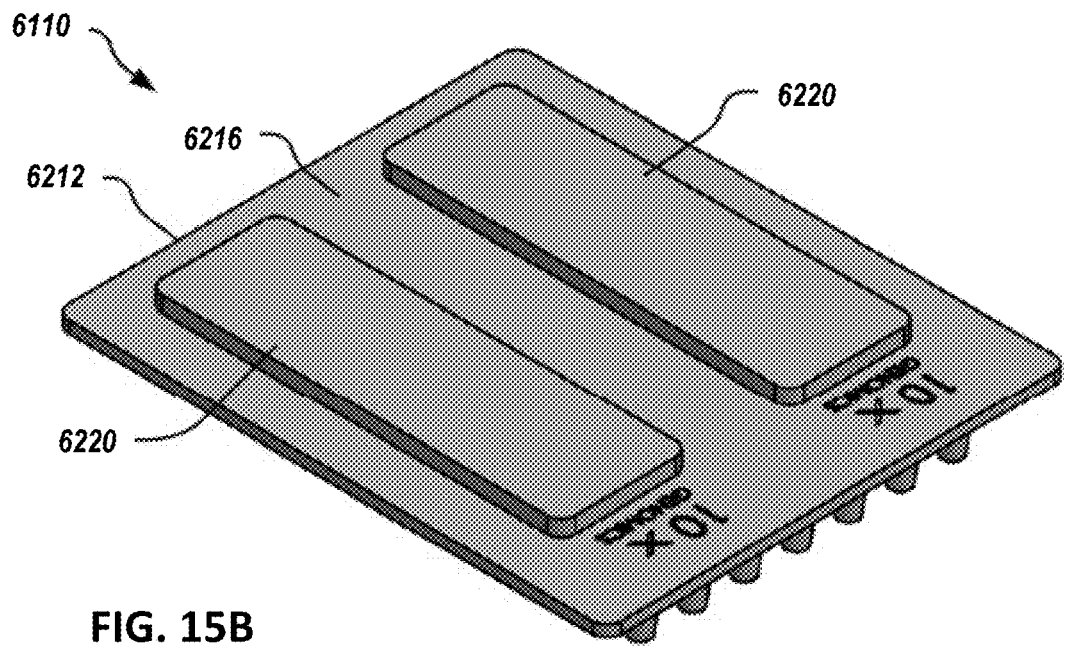
Figure 15C:
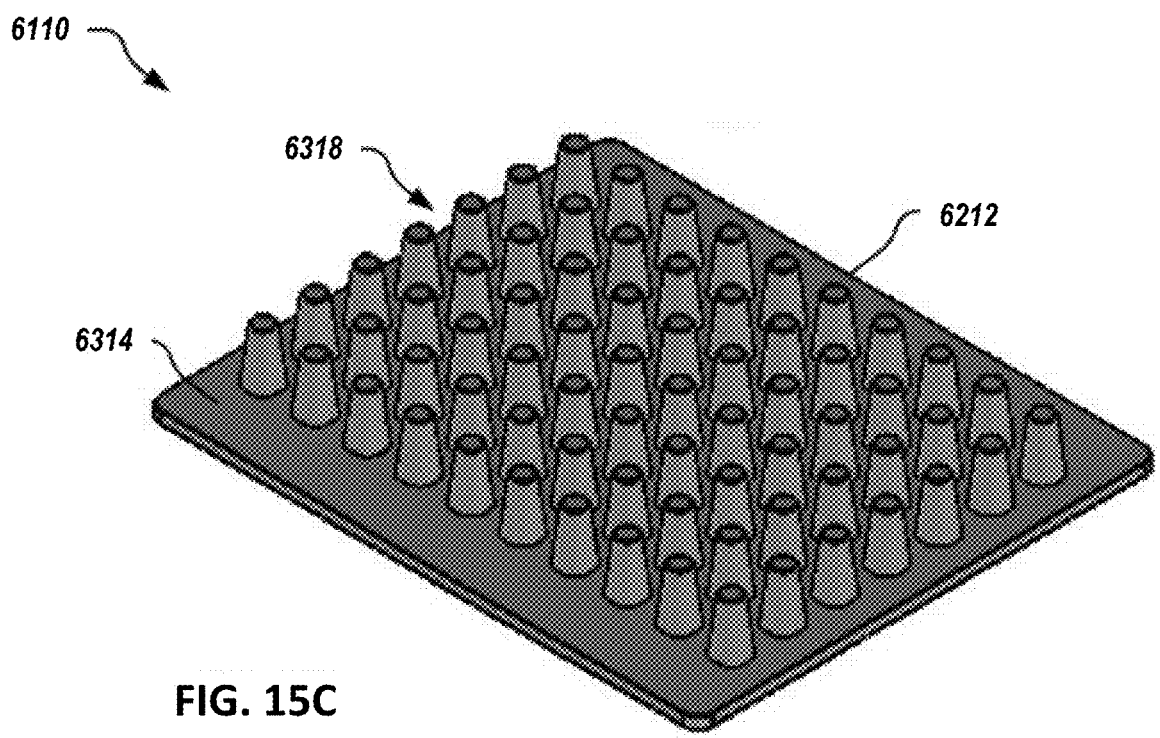
Figure 16:
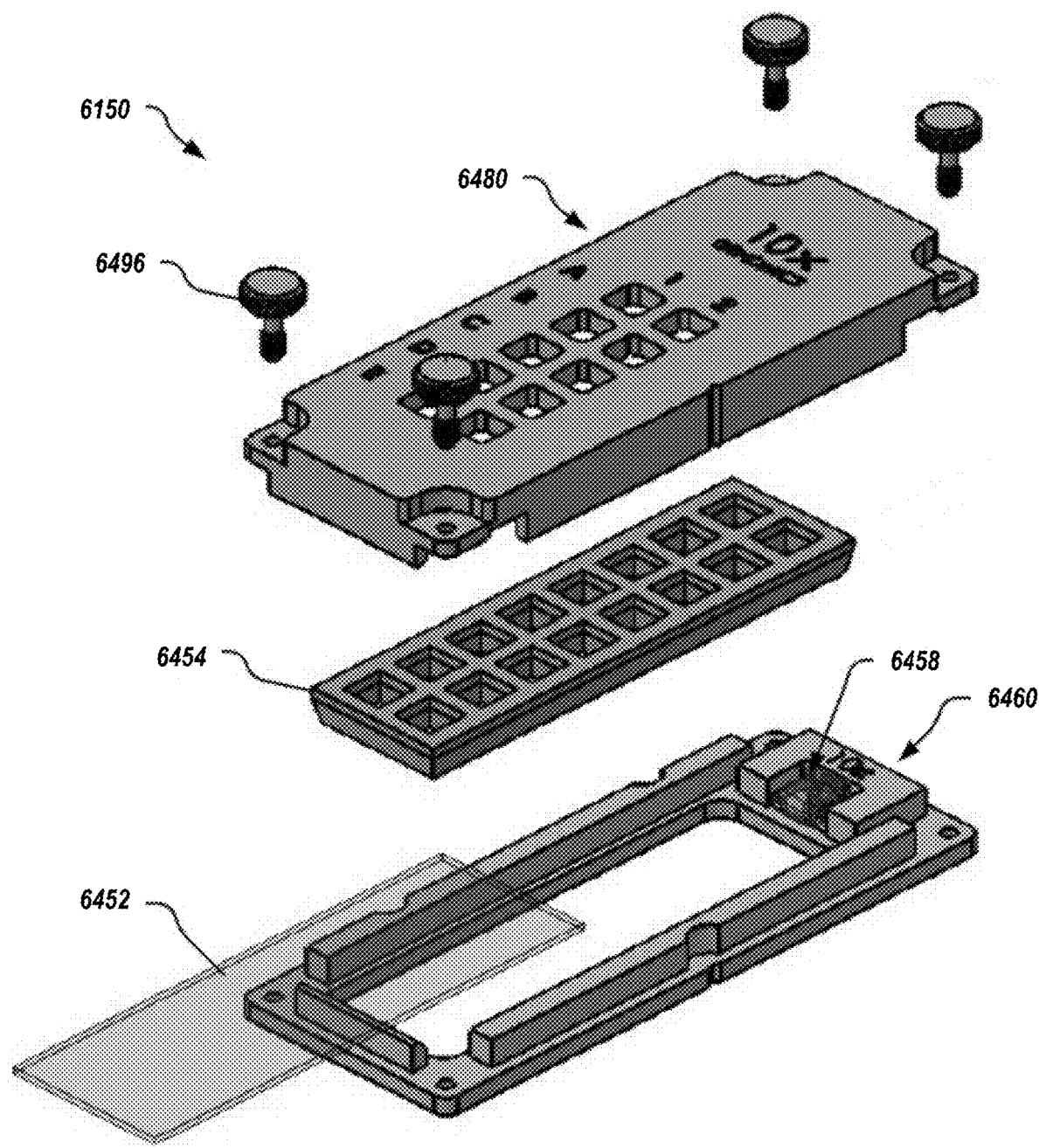
FIG. 16 is an exploded view of the substrate holder of FIG. 15.

Referring to FIGS. 15B and 15C, the plate 6110 can include a platform 6212 with a first surface 6314 and a second surface 6216. The plate 6110 can further include a plurality of members 6318 extending from the first surface 6314. In some embodiments, the plate 6110 can include one or more support members 6220.

The plate 6110 can be generally formed of thermally conductive material to facilitate heat transfer between a heating device and the substrate holder 6150. In some embodiments, the plate 6110 can be made of a metal such as (but not limited to) aluminum and/or stainless steel.

In general, the platform 6212 is configured to be received by a heating device. More specifically, the platform 6212 is generally configured such that thermal transfer occurs between the heating elements of a heating device and the platform 6212. The heat transferred to the platform 6212 is then further transferred to a substrate, as will be discussed in greater detail below.

The plurality of members 6318 can be dimensioned to be received by different regions of a heating device. For example, in some embodiments, the plurality of members 6318 can be dimensioned to be received within individual sample wells of a thermocycler (for example, thermocycler wells that are generally dimensioned to receive small volume test tubes such as 200 µL tubes). In general, the platform 6212 can include any number of members 6318. For example, in some embodiments, the platform 6212 includes between 4 members and 96 members. Typically, heat is more evenly transferred to the platform 6212 when the number of members 6318 is larger, and they are distributed relatively evenly on the surface 6314.

The support member 6220 can extend from the platform 6212 and be configured to couple to the substrate holder 6150. In some embodiments, the support member 6220 can include one or more recesses or protrusions that couple to one or more complementary protrusions or recesses on the substrate holder 6150 to aid in coupling the substrate holder 6150 to the plate 6110. In some embodiments, the support member 6220 can be entirely received by a portion of the substrate holder 6150. In some embodiments, a portion of the support member 6220 can be received by a portion of the substrate holder 6150. In some embodiments, the support member 6220 can be substantially flat on a top face. In some embodiments, the support member 6220 can be sized and positioned such that the plate 6110 can include multiple support members 6220. For example, in some embodiments, the plate 6110 can include two support members 6220.

Referring generally to FIGS. 16-22, a substrate holder 6150 can include a bottom member 6460 and a top member 6480. In some embodiments, the substrate holder 6150 can further include a slide 6452. In some embodiments, the substrate holder 6150 can include a gasket 6454 (see also FIG. 21).

Figure 17A:
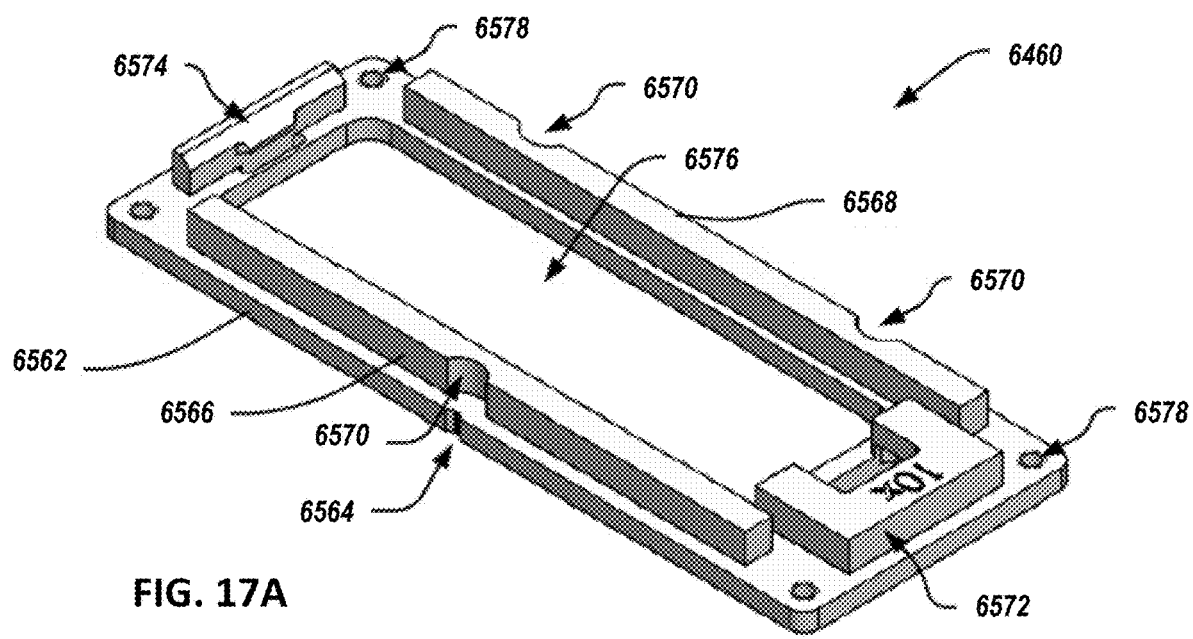
FIGS. 17A-B are A) a top perspective view of a bottom member of the substrate, and B) a bottom perspective view of the bottom member of FIG. 16.
Figure 17B:
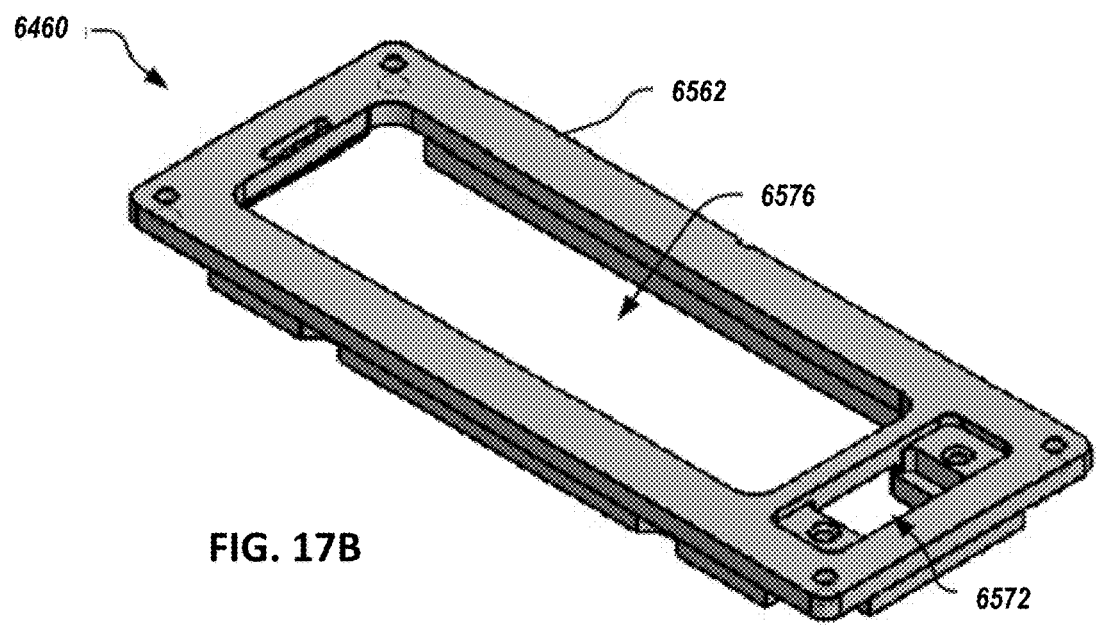
Figure 18:
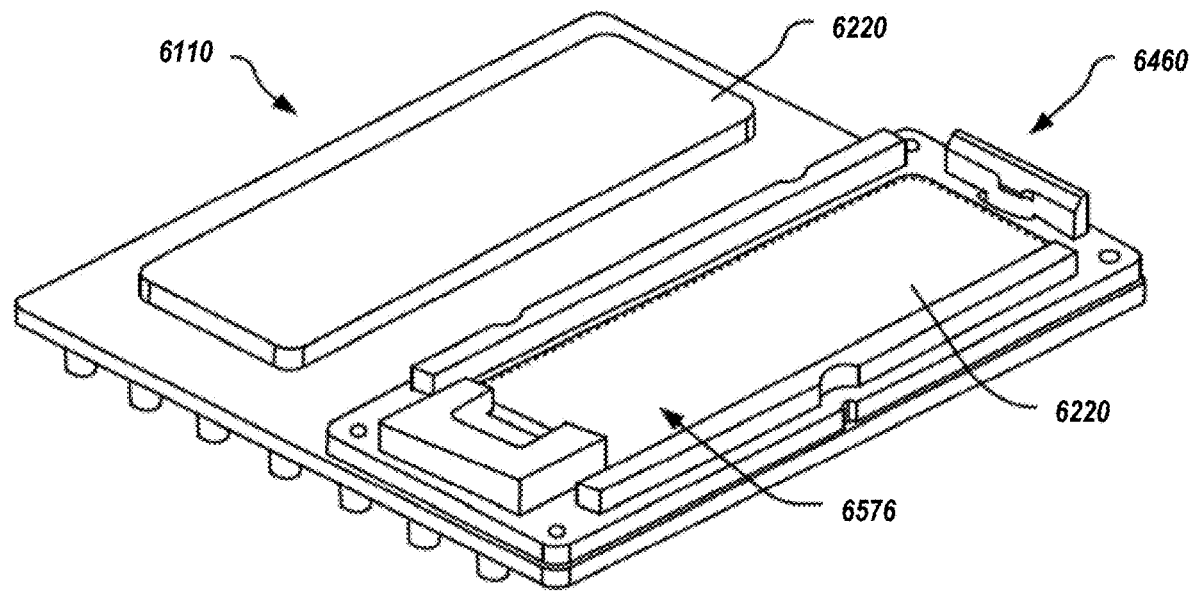
FIG. 18 is a perspective view of the bottom member of FIG. 17A coupled to the plate of FIG. 15.
Figure 19:
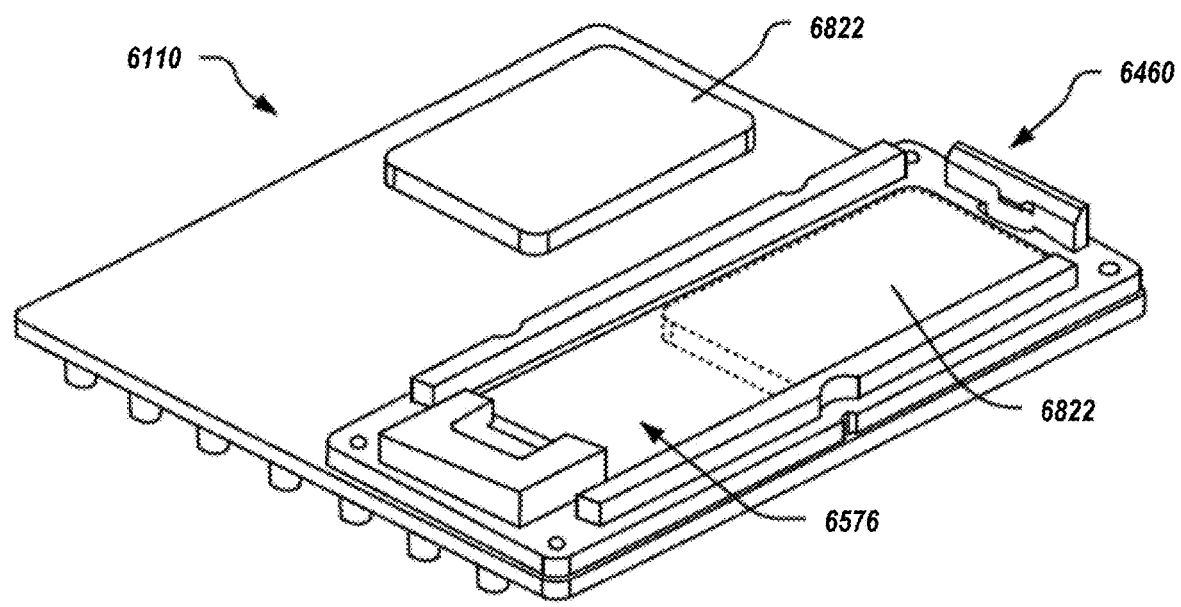
FIG. 19 is a perspective view of the bottom member of FIG. 17A coupled to a second plate embodiment.
Figure 20B:
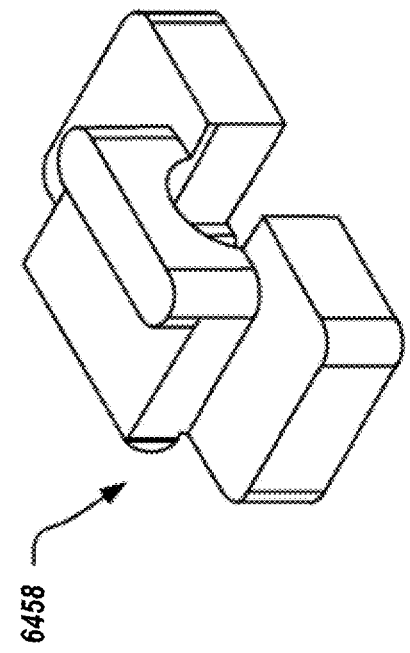
FIGS. 20A-B are A) a front perspective view of a fastener for use with the bottom member of FIG. 17 and B) a back perspective view of the fastener.
Figure 20A:
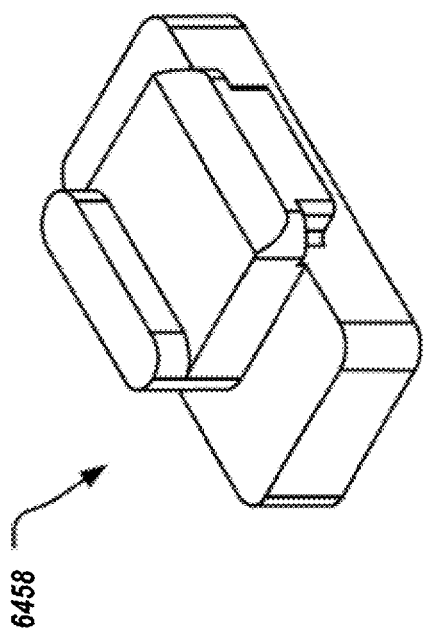
Figure 21:
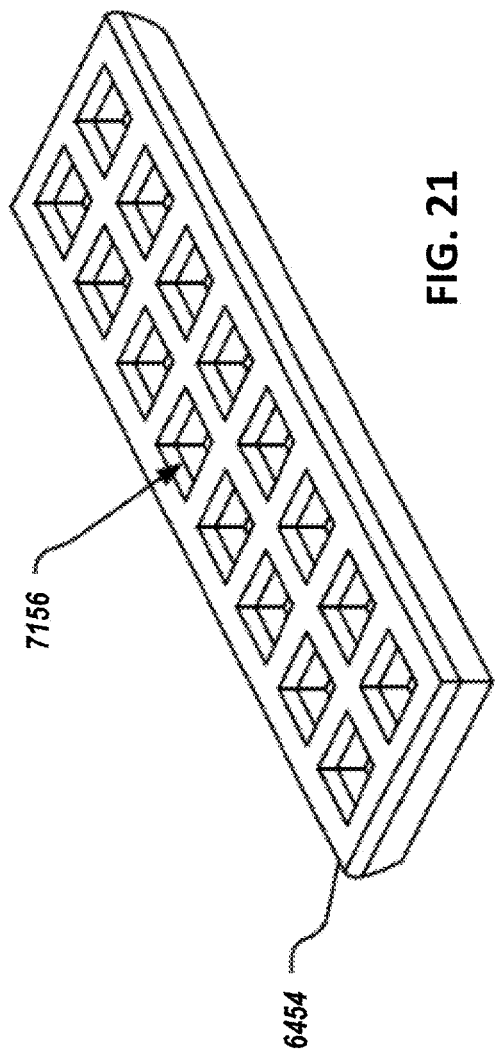
FIG. 21 is a perspective view of a gasket for use with the substrate holder of FIG. 16.

Referring to FIGS. 17A and 17B, the bottom member 6460 can include a base 6562, a first side wall 6566 and a second side wall 6568. The bottom member 6460 can be configured to mount slide 6452.

In some embodiments, the base 6562 can include a marker 6564. The marker 6564 can aid in coupling the bottom member 6460 and the top member 6480 in a certain orientation. For example, in some embodiments, the bottom member 6460 and the top member 6480 may only be able to couple together in a single orientation. In some embodiments, the marker 6564 can be a line, groove, indent, protrusion, symbol, color, etc. to distinguish one side of the base 6562 from another side of the base 6562.

The first side wall 6566 and the second side wall 6568 can be positioned on opposing longitudinal sides of the base 6562. The side walls 6566 and 6568 can extend substantially perpendicular from the base 6562. In some embodiments, the side walls 6566 and 6568 are slightly offset on edges of the base 6562 such that a portion of the base 6562 is exposed on either side of both side walls 6566 and 6568. The side walls 6566 and 6568 can aid in securing the slide 6452 in the bottom member 6460. In some embodiments, when the slide 6452 is secured in the bottom member 6460, the slide 6452 may rest on the base 6562. In some embodiments, the side walls 6566 and 6568 can be configured to engage with the top member 6480. For example, in some embodiments, the side walls 6566 and 6568 can include one or more recesses 6570. In some embodiments, the side wall 6566 can include a single recess 6570, while the side wall 6568 includes multiple recesses (e.g., two recesses). Such a configuration can provide single direction coupling of the bottom member 6460 and the top member 6480 for ease of use.

The base 6562 can further include means for mounting the slide 6452. For example, in some embodiments, the base 6562 can include a fastener housing 6572 and an end securing member 6574. The end securing member 6574 can aid in securing the slide 6452 in the bottom member 6460. In some embodiments, the end securing member 6574 can include a ridge to limit movement of the slide 6452 away from the base 6562. The fastener housing 6572 can provide housing for a fastener 6458 (see e.g., FIG. 20). The fastener 6458 can be a clip, ridge, or other means of removably coupling the slide 6452 to the bottom member 6460. In some embodiments, the fastener 6458 can include a spring such that pushing the slide 6452 against the fastener 6458 causes the fastener 6458 to move past the ridge of the end securing member 6574, allowing the slide 6452 to enter the bottom member 6460. Once the slide 6452 is released, the spring can return the fastener 6458 to a more neutral position, causing the slide 6452 to abut the end securing member 6574.

Figure 25:
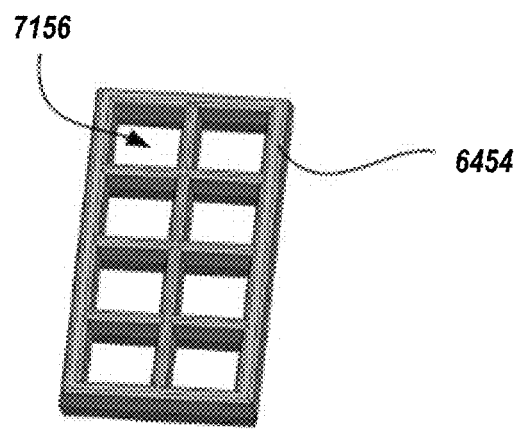
FIG. 25 is a perspective view of an example gasket.

The bottom member 6460 can include means for coupling to the support member 6220 of the plate 6110. For example, in some embodiments, the base 6562 can include an aperture 6576 extending through the base 6562 within the side walls 6566 and 6568. Referring to FIGS. 25 and 26, the bottom member 6460 is shown coupled to the plate 6110. In some embodiments, the aperture 6576 can be sized such that the support member 6220 substantially fills the aperture 6576 (see FIG. 18). In some embodiments, the aperture 6576 can be larger than the support member 6822, such that the support member 6220 only fills a portion of aperture 6576 (see FIG. 19). In some embodiments, the support member 6220, the bottom member 6460 and the aperture 6576 are configured such that the slide 6452 is in close proximity to the support member 6220. In some embodiments, the support member 6220, the bottom member 6460 and the aperture 6576 are configured such that the slide 6452 is in direct contact with the support member 6220. In some embodiments, the support member 6220, the bottom member 6460 and the aperture 6576 are configured such that a portion of a sample region of the slide 6452 is in proximity to the support member 6220. In some embodiments, the portion of the sample region of the slide 6452 is 50% to 100% of the sample region. In some embodiments, the portion of the sample region is at least 60% of the sample region. In some embodiments, the portion of the sample region is at least 75% of the sample region. In some embodiments, the portion of the sample region is at least 80% of the sample region. In some embodiments, the portion of the sample region is at least 85% of the sample region.

Referring back to FIGS. 16-22, the bottom member 6460 can include an engagement mechanism for coupling the bottom member 6460 to the top member 6480. In some embodiments, the engagement mechanism includes screws 6496. Accordingly, the base 6562 can include one or more threaded apertures 6578 configured to receive the screws 6496. The base 6562 can be sized such that the screws 6496 do not protrude underside of the base 6562.

The gasket 6454 can be positioned inside the substrate holder 6150. The gasket 6454 can include a plurality of apertures 7156 (see also FIG. 21) that can create a plurality of wells when the gasket 6454 abuts the slide 6452. In some embodiments, the gasket 6454 can be made of rubber, silicone, or a similar material to create a seal with the slide 6452. In some embodiments, the gasket 6454 can be made of a material that is hydrophobic. Accordingly, different reactions can be conducted in the various wells of the gasket 6454. In some embodiments, the engagement of the bottom member 6460 and the top member 6480 creates ample pressure to maintain division between the wells created by the apertures 7156.

Figure 22A:
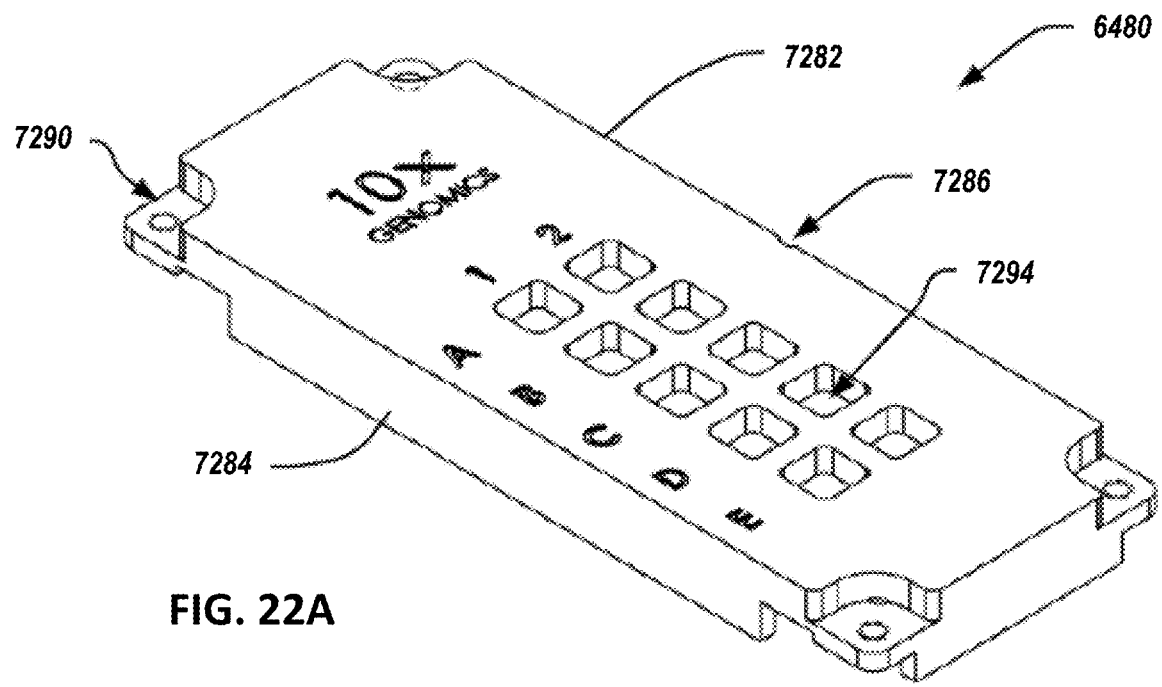
FIGS. 22A-B are a A) top perspective view of a top member of the substrate holder, and B) a bottom perspective view of the top member of FIG. 16.
Figure 22B:
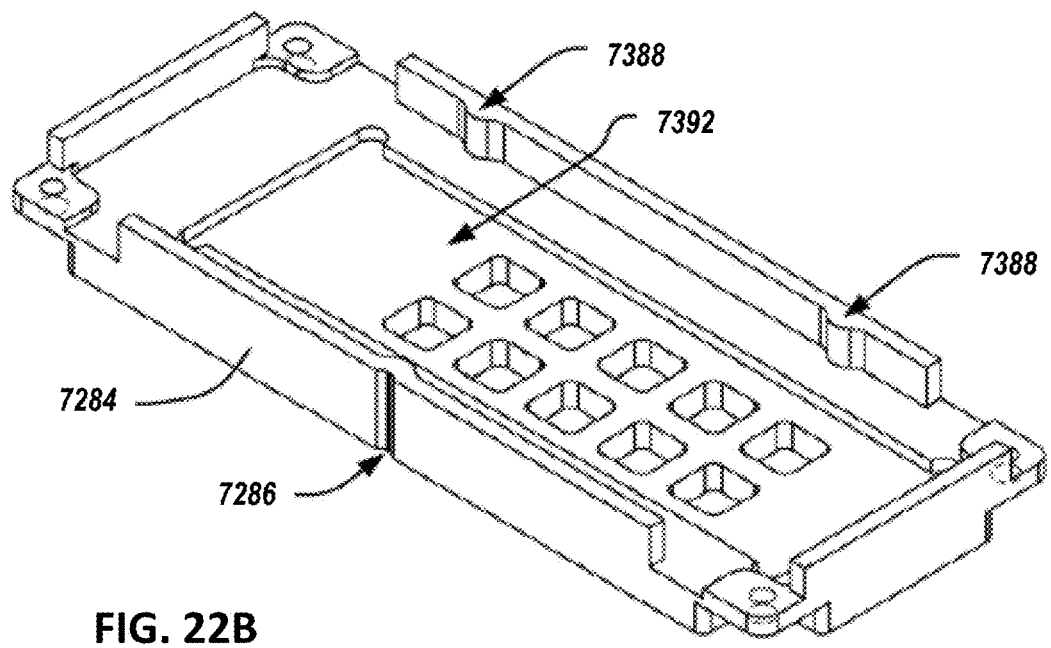

Referring to FIGS. 22A and 22B, the top member 6480 can include a body 7282 with walls 7284. In some embodiments, one side of the body 7282 and/or the wall 7284 can include a marker 7286. Marker 7286 can aid in coupling the bottom member 6460 and the top member 6480 in a certain orientation. For example, in some embodiments, the bottom member 6460 and the top member 6480 may only be able to couple together in a single orientation. In some embodiments, the marker 7286 can be a line, groove, indent, protrusion, symbol, color, etc. to distinguish one side of the body 7282 from another side of the body 7282.

In some embodiments, the walls 7284 can be configured to engage with the bottom member 6460. For example, in some embodiments, the walls 7284 can include one or more protrusions 7388. In some embodiments, a first wall 7284 can include a single protrusion 7388, while a second wall 7284 can includes multiple protrusions 7388 (e.g., two protrusions). Such a configuration can provide single direction coupling of the bottom member 6460 and the top member 6480 for ease of use.

The body 7282 can further include an engagement mechanism for coupling the top member 6480 to the bottom member 6460. In some embodiments, the engagement mechanism includes screws 6496. Accordingly, the body 7282 can include one or more threaded apertures 7290 configured to receive the screw 6496. The body 7282 can be configured such that when the apertures 7290 receive the screws 6496, the heads of the screws 6496 are flush or lower than an upper face of the body 7282. Accordingly, the top member 6480 can be configured such that a top plate of a heating device can abut the top member 6480, providing heating of the substrate holder 6150.

In some embodiments, the body 7282 can include a recess 7392 on the underside of the body 7282. In some embodiments, the recess 7392 can receive the gasket 6454. In some embodiments, the recess 7392 can removably couple the gasket 6454. In some embodiments, the body 7282 can include the gasket 6454, such that the gasket 6454 is integrated with the body 7282.

In some embodiments, the body 7282 can include a plurality of apertures 7294. In some embodiments, the plurality of apertures 7294 can be configured to enable reagents to be added to the substrate on the slide 6452. In some embodiments, the plurality of apertures 7294 can be configured to be aligned with the plurality of apertures 7156 of the gasket 6454. In some embodiments, the plurality of apertures 7294 can be configured with a format and spacing to enable use with a multichannel pipette. In some embodiments, the plurality of apertures 7294 can be located on only a portion of the body 7282. In some embodiments, the body 7282 can include labels or markings adjacent to the plurality of apertures 7294.

While the substrate holder 6150 is described as including multiple pieces (e.g., the bottom member 6460, the top member 6480, the slide 6452, the gasket 6454, etc.), components of the substrate holder 6150 can be integrated with one another. For example, in some embodiments, the gasket 6454 can be integrated with the top member 6480. As another example, the top member 6480 and the bottom member 6460 can be a single piece that is configured to receive the slide 6452.

In some embodiments, the substrate holder 6150 can be made of a material that is reusable. For example, in some embodiments, the substrate holder 6150 can be washed and sanitized for reuse. Optionally, the gasket 6454 can be reusable or replaceable in such an embodiment. In some embodiments, the substrate holder 6150 can be made for single use and can be disposable.

Referring to FIGS. 23-25, another example substrate cassette is described. An example device 7498 can be used to replace the substrate cassettes 4010, 4810 described herein. The device 7498 can include a substrate holder 7400, a gasket 6454, and a substrate, such as a glass slide 6452. The slide 6452 includes a first surface and a second surface. In some embodiments, the substrate holder 7400 is configured to receive the slide 6452. In some embodiments, the substrate holder 7400 includes an attachment mechanism to hold the slide 6452 to the substrate holder 7400. The second surface of the slide 6452 can provide a substrate for receiving a sample. In some embodiments, the substrate holder 7400 is plastic component (e.g., injection molded plastic component). In some embodiments, the gasket 6454 is configured to be positioned in between the substrate holder 7400 and the slide 6452. In some embodiments, the device 7498 (or any one of its components) can be a single-use device (or component). In some embodiments, the device 7498 is entirely disposable or at least partially composed of disposable components.

Figure 23A:
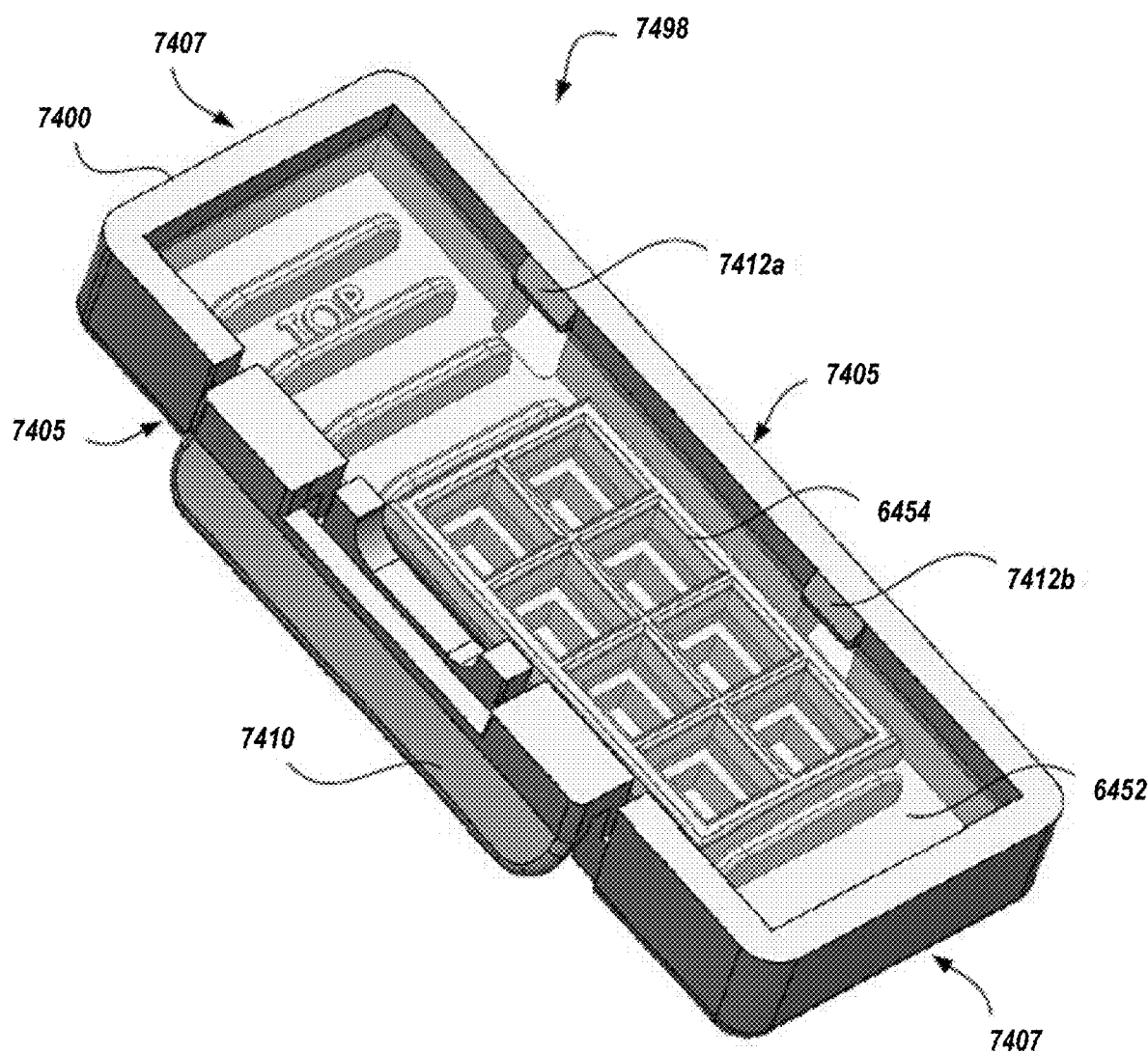
FIGS. 23A-C are A) a perspective view of an example substrate holder, B) an exploded view of the substrate holder, and C) a partial, perspective view of the substrate holder.
Figure 23B:
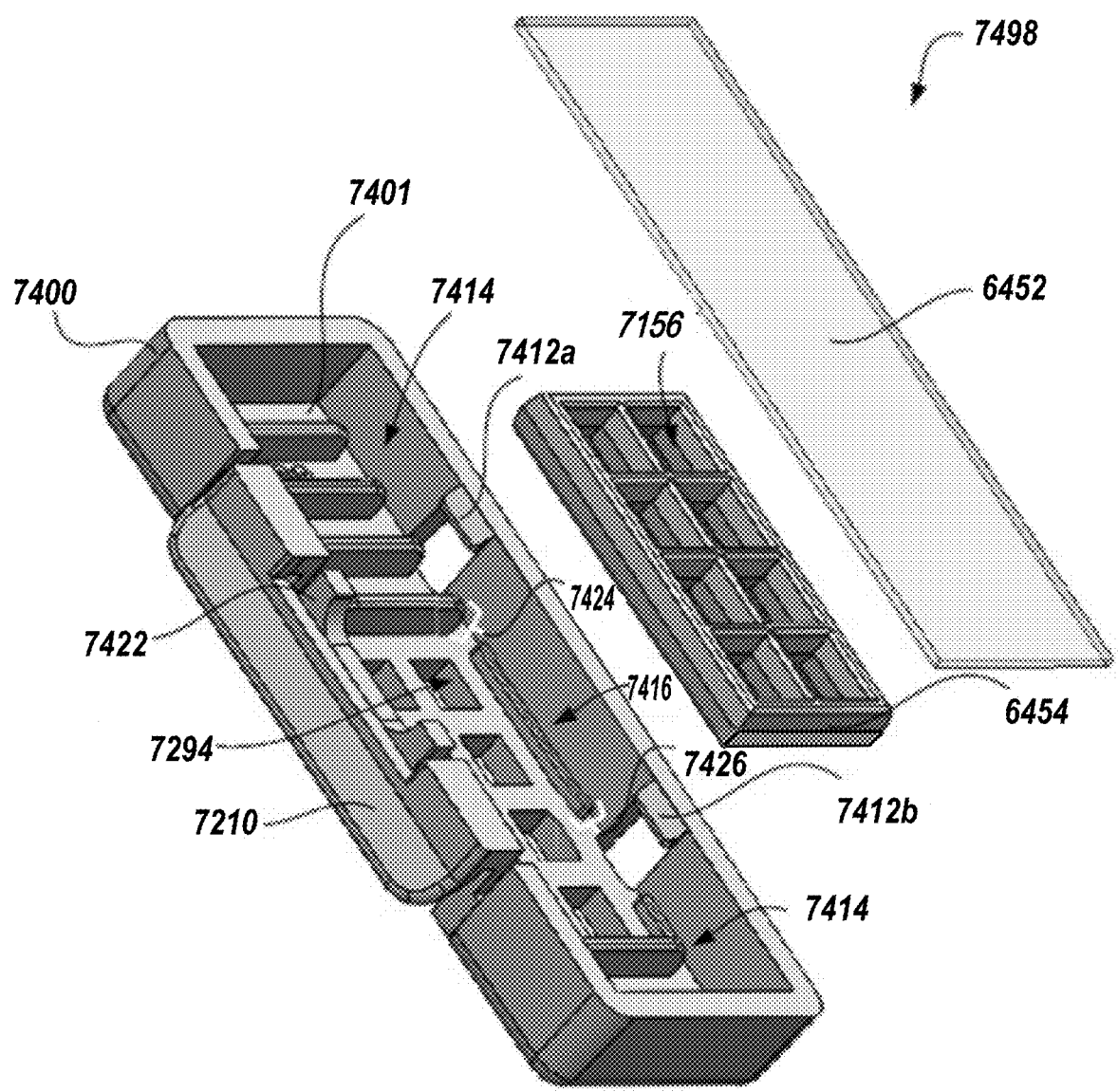
Figure 23C:
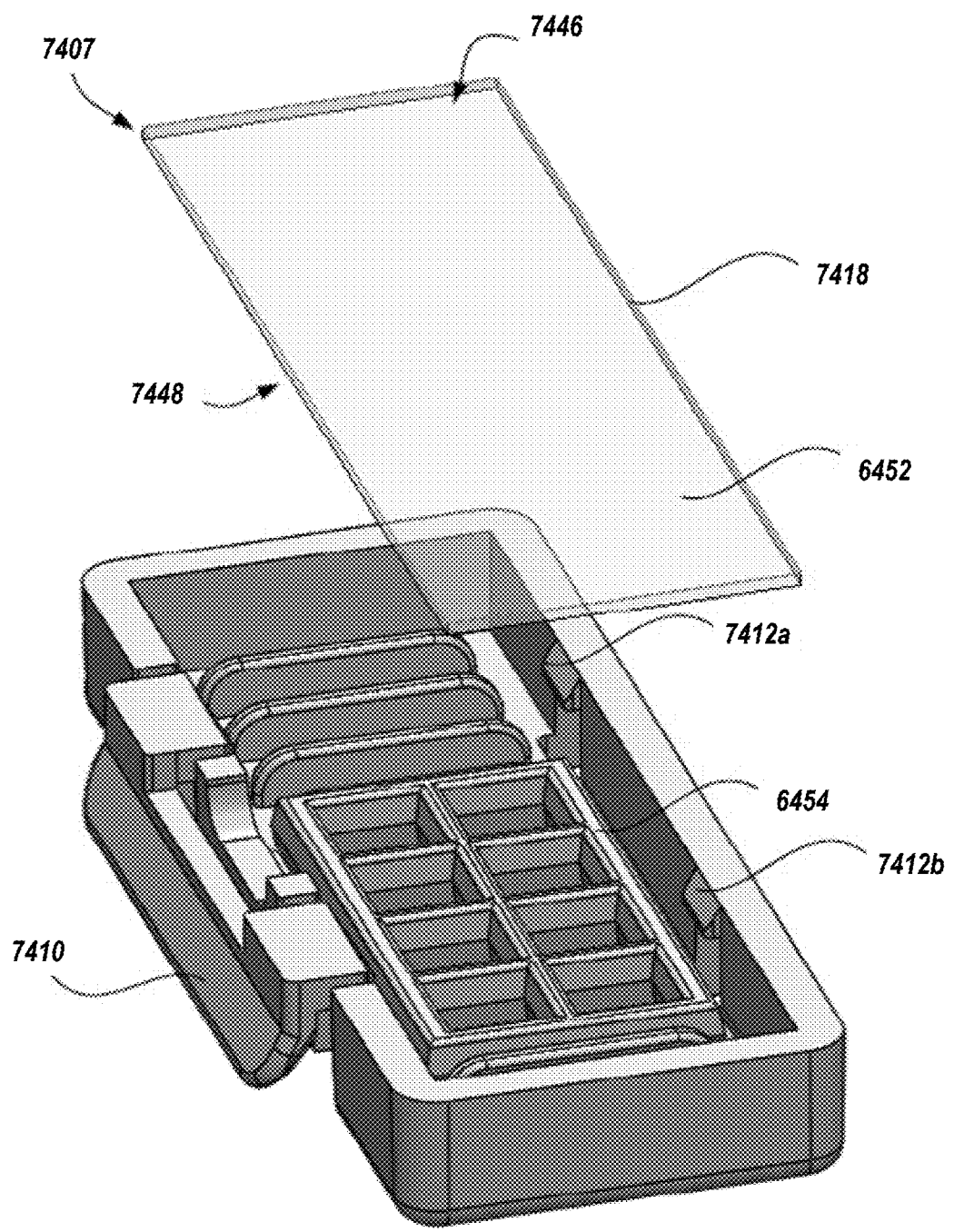

FIG. 23A shows the device 7498 in an assembled state. In particular, FIG. 23A shows the substrate holder 7400 receiving the gasket 6454 and the slide 6452. The substrate holder 7400 has longitudinal sides 7405 and latitudinal sides 7407. The substrate holder 7400 can include one or more fasteners, such as a side mounted press latch 7410 for snap engagement. Any type of fastener that allows releasable engagement can be used, such as, for example, screws and press fit type connectors. The press latch 7410 can be mounted in a longitudinal side 7505 of the substrate holder 7400, as shown in FIGS. 23A-23C. Alternatively, in some embodiments, the press latch 7410 can be mounted in a latitudinal side 7407 of the substrate holder 7400. In some embodiments, the substrate holder 7400 can include two, three, or four press latches. The press latch 7410 can be configured to engage the slide 6452. In some embodiments, the press latch 7410 can be a lever, a clip, or a clamp. In some embodiments, the press latch 7410 can further include one or more springs.

The substrate holder 7400 can further include one or more engagement features, such as a first tab 7412a and a second tab 7412b. The first and second tabs 7412a and 7412b, respectively, can protrude from a longitudinal side 7505 of the substrate holder 7400 that opposes the longitudinal side having the press latch 7410. In some embodiments, the substrate holder 7400 includes three, four, five, six, seven, eight, nine, ten or more tabs. In some embodiments, the tabs protrude from a longitudinal side 7505 or a latitudinal side 7407 of the substrate holder 7400. The first and second tabs 7412a and 7412b can be configured to engage the slide 6452. In some embodiments, the first and second tabs 7412a and 7412b are rigid and do not flex when engaging the slide 6452. In some embodiments, the tabs 7412a and 7412b can be flexible.

Referring to FIG. 23B, the substrate holder 7400 includes a bottom surface 7401. The bottom surface 7401 includes a plurality of latitudinal ribs 7414 and longitudinal ribs 7416 configured to support the slide 6452 and the gasket 6454 when the device 7498 is assembled. The bottom surface 7401 further defines a plurality of apertures 7294 that are configured to align with the plurality of apertures 7156 defined by the gasket 6454, when the device 7498 is assembled. The substrate holder 7400 further includes a c-shaped tab 7422 shaped to provide the user with an ergonomic grip surface to help facilitate engagement with the press latch 7410.

Referring to FIG. 23C, the slide 6452 includes a first surface 7446, a second surface 7448, and a side edge 7418. When inserting the slide 6452 into the substrate holder 7400, the side edge 7418 can be inserted first such that first and second tabs 7412a and 7412b engage the side edge 7418 as the slide 6452 rests on the gasket 6454 an on the plurality of latitudinal ribs 7414. In some embodiments, the side 7418 can measure about 6 inches. In some embodiments, the sides shorter than the side 7418 can measure about 1 inch. In some embodiments, the slide 6452 can measure about 75 millimeters (mm) by 25 mm. In some embodiments, the slide 6452 can measure about 75 millimeters (mm) by 50 mm. In some embodiments, the slide 6452 can measure about 48 millimeters (mm) by 28 mm. In some embodiments, the slide 6452 can measure about 46 millimeters (mm) by 27 mm. In some embodiments, the slide 6452 is a glass slide.

Figures 24A, 24B:
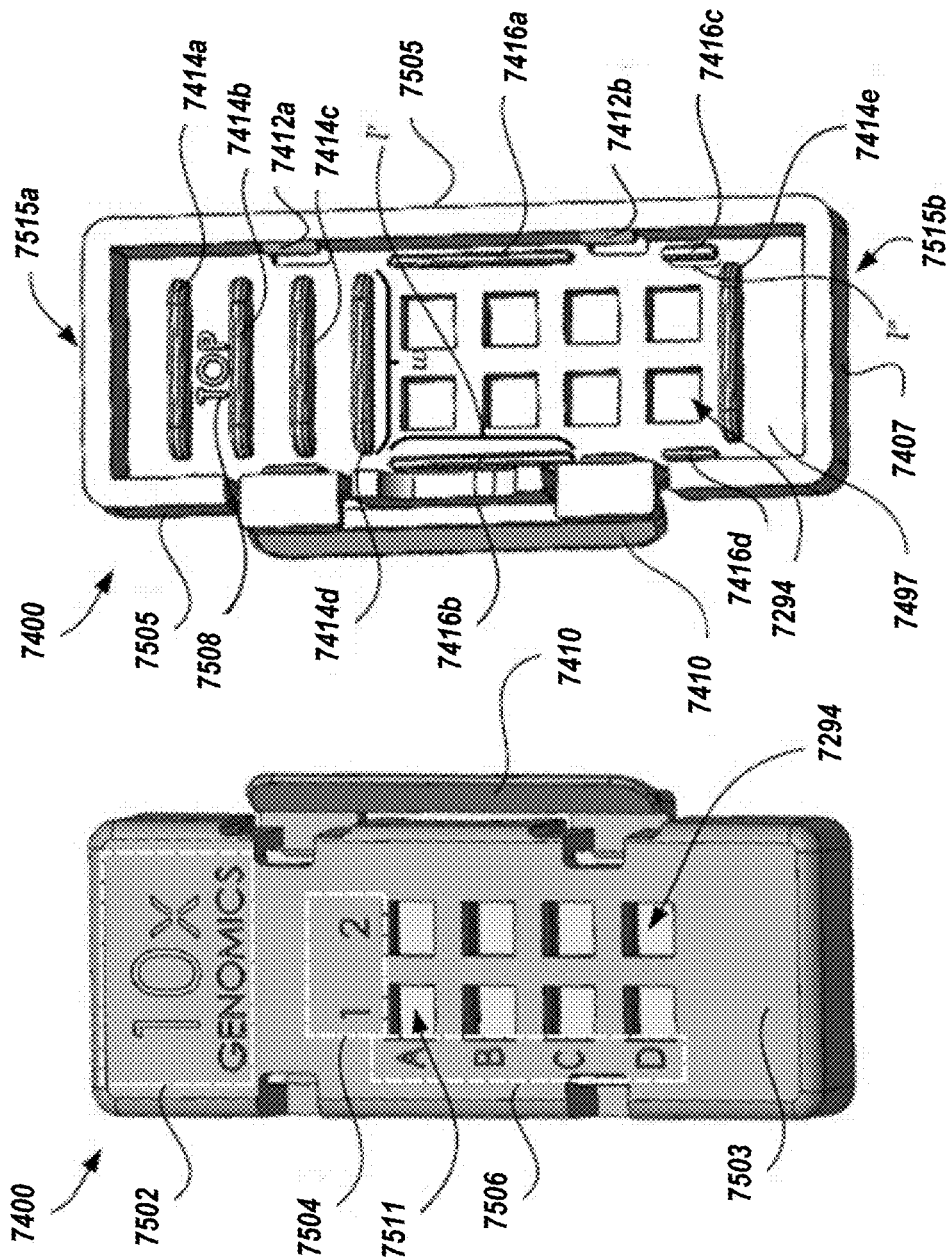
FIGS. 24A-C are A) a top perspective view of the substrate, B) a bottom perspective view of the substrate, and C) a side perspective view of the substrate holder of FIG. 23A.

Referring to FIG. 24A, the substrate holder 7400 includes a top surface 7503. The top surface 7503 defines the plurality of apertures 7294. Furthermore, the top surface 7503 includes a logo 7502, a first identifier 7504, and a second identifier 7506. The first identifier 7504 can identify the columns of the plurality of apertures 7294. The second identifier 7506 can identify the rows of the plurality of apertures 7294. In some embodiments, the first identifier 7504 and the second identifier 7506 are letters or numbers. In some embodiments, the first identifier 7504 and the second identifier 7506 can aid in aligning and/or inserting the slide 6452 into the substrate holder 7400 in a certain orientation. In some embodiments, the slide 6452 may include samples (e.g., biological material samples) on a portion of its surface that align with one or more of the plurality of apertures 7294. In some embodiments, the samples (e.g., biological material samples) may be identified in the same manner as the corresponding aperture of the plurality of apertures 7294. For example, in some embodiments, the slide 6452 may include a sample named "A1" that corresponds with the aperture 7511 labeled as "A1" by the first identifier 7504 and the second identifier 7506 in FIG. 24A. As such, in some embodiments, the first identifier 7504 and the second identifier 7506 guide a user to correctly place the slide 6452 into the substrate holder 7400. In some embodiments, the first identifier 7504 and the second identifier 7506 can be a line, groove, indent, protrusion, symbol, color, etc. to distinguish the rows and columns of the plurality of apertures 7294.

Referring to FIG. 24B, the substrate holder 7400 includes a first latitudinal rib 7414a, a second latitudinal rib 7414b, a third latitudinal rib 7414c, a fourth latitudinal rib 7414d, and a fifth latitudinal rib 7414e having a width w. The plurality of latitudinal ribs 7414 is configured to support a slide 6452. The first, second, third, fourth, and fifth latitudinal ribs 7414a, 7414b, 7414c, 7414d, and 7414e can have an equal width w, as shown in FIG. 24B. In some embodiments, the widths of the plurality of latitudinal ribs can vary. The first, second, and third latitudinal ribs 7414a, 7414b, and 7414c, respectively, extend perpendicular from the bottom surface 7401 near a first end 7515a of the substrate holder 7400. The fifth latitudinal rib 7414e extends substantially perpendicular from the bottom surface 7401 near a second end 7515b of the substrate holder 7400. In some embodiments, the substrate holder 7400 may include 6, 7, 8, 9, 10, 15, 20 or more latitudinal ribs.

The substrate holder 7400 further includes a first longitudinal rib 7416a, a second longitudinal rib 7416b, a third longitudinal rib 7416c, and a fourth longitudinal rib 7416d that extend substantially perpendicular from the bottom surface 7401. The plurality of longitudinal ribs 7416 is configured to provide longitudinal support to the gasket 6454. For example, in some embodiments, the plurality of longitudinal ribs 7416 abuts the longitudinal sides of the gasket 6454. Furthermore, together with the fourth and fifth latitudinal ribs 7414c and 7414e, the plurality of longitudinal ribs frame an area of the bottom surface 7401 (e.g., gasket area) that is sufficiently sized and configured to receive the gasket 6454. The first longitudinal rib 7416a, second longitudinal rib 7416b, third longitudinal rib 7416c, and fourth longitudinal rib 7416d can be disposed parallel to the longitudinal sides 7505 along the side edges. The first longitudinal rib 7416a, second longitudinal rib 7416b, third longitudinal rib 7416c, and fourth longitudinal rib 7416d have a second height 7426, as shown in FIG. 24B. The first, second, third, fourth, and fifth latitudinal ribs 7414a, 7414b, 7414c, 7414d, and 7414e have a first height 7424, as shown in FIG. 32B. The first height 7424 can be greater than the second height 7426, as shown in FIGS. 32-33. In some embodiments, the first height 7424 is equal to the second height 7426 (see FIG. 23B). In some embodiments, the first height 7424 is less than the second height 7426. The first and second longitudinal ribs 7416a and 7416b have a length l'. The third and fourth longitudinal ribs 7416c and 7416d have a length l". The length l' is can be greater than the length l", as shown in FIG. 23B. In some embodiments, the length l' is equal to the length l". In some embodiments, the length l' is less than the length l". In some embodiments, the substrate holder 7400 may include 5, 6, 7, 8, 9, 10, 15, 20 or more longitudinal ribs.

The substrate holder 7400 further includes a third identifier 7508 that aids a user in positioning and/or orienting the substrate holder 7400. For example, in some embodiments, the third identifier 7508 aids in identifying the first end 7515a or aids in distinguishing the first end 7515a from the second end 7515b. Still yet in further embodiments, the third identifier can be a line, groove, indent, protrusion, symbol, color, etc. that aids a user in correctly positioning slide 6452 into the substrate holder 7400.

Figure 24C:
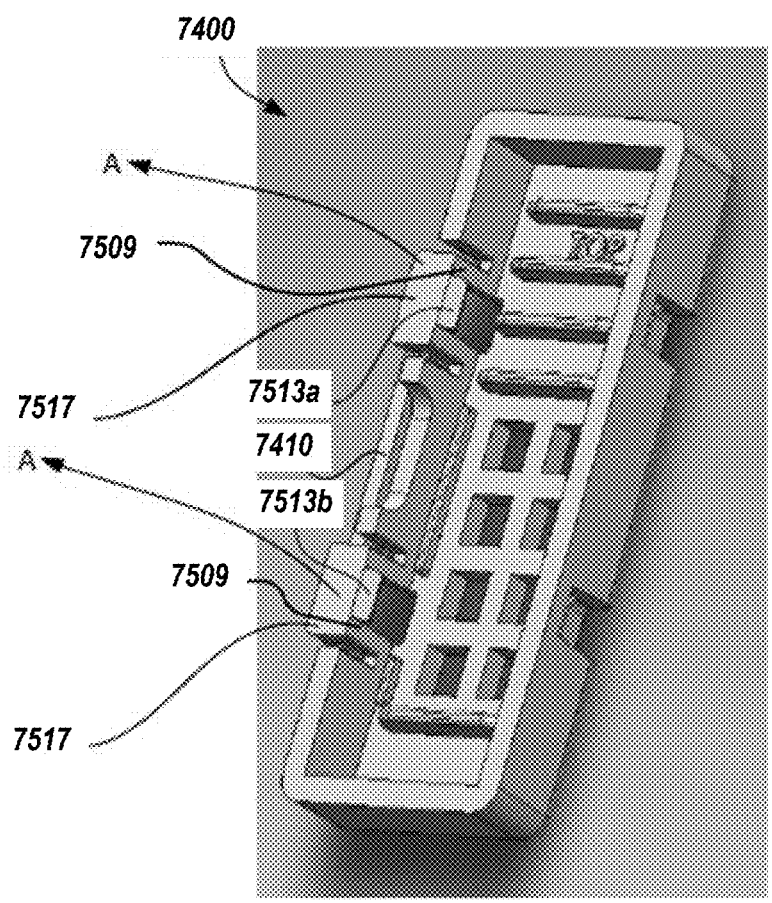

Referring to FIG. 24C, the substrate holder includes a first flexible tab 7513a and a second flexible tab 7513b. The first and second flexible tabs 7513a and 7513b, respectively, can protrude from top portions 7517 of the press latch 7410 that oppose the longitudinal side 7505 having the first and second tabs 7412a and 7412b. The first and second flexible tabs 7513a and 7513b can protrude from an interior surface 75109 of the top portions 7517 of the press latch 7410. To utilize the substrate holder 7400, a user can grip the substrate holder 7400 in one hand with the bottom surface 7401 face up (i.e., facing the user). Next, the user can place the gasket 6454 over the plurality of apertures 7294. The user can depress the press latch 7410 with one hand, this flexes the first and second flexible tabs 7513a and 7513b on one longitudinal side 7505 open, in the direction of arrows A. As such, the user can load the slide 6452 into the first and second tabs 7412a and 7412b first, and subsequently hinge slide 6452 into opposite longitudinal side (i.e., the side having the first and second flexible tabs 7513a and 7513b). Lastly, the user can release the press latch 7410 so the slide 6452 can snap into the first and second flexible tabs 7513a and 7513b.

Referring to FIG. 25, the gasket 6454 includes a plurality of apertures 7156. In some embodiments, the gasket 6454 includes eight apertures. In some embodiments, the gasket 6454 includes sixteen apertures. In some embodiments, the gasket 6454 includes 24 apertures. In some embodiments, the gasket 6454 includes 96 apertures. In some embodiments, the gasket 6454 is made from a material that can withstand temperatures up to about 60 degrees Celsius. In some embodiments, the gasket 6454 is made from a heat-resistant material. In some embodiments, the gasket 6454 is made from a flexible or pliable material. Non-limiting examples of flexible or pliable materials include rubber, silicone, and polyurethane. It is contemplated that the number of apertures is the same as the number of sample arrays on a substrate.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774, 374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/ 0277663, 2020/024641, 2019/330617, 2019/264268, 2020/ 256867, 2020/224244, 2019/194709, 2019/161796, 2019/ 085383, 2019/055594, 2018/216161, 2018/051322, 2018/ 0245142, 2017/241911, 2017/089811, 2017/067096, 2017/ 029875, 2017/0016053, 2016/108458, 2015/000854, 2013/ 171621, WO 2018/091676, WO 2020/176788, Rodriques et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/ 176788 and/or U. S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof, (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., Splint® ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method for capturing analytes from one or more biological samples, the method comprising:
   placing the one or more biological samples in contact with capture probes on a substrate, the one or more biological samples including the analytes;
   inserting the substrate into a substrate holder of a substrate cassette;
   subsequent to placing the one or more biological samples in contact with the capture probes on the substrate and inserting the substrate into the substrate holder, arranging the substrate cassette and the substrate to align one or more apertures of the substrate cassette with one or more substrate regions of the substrate and define one or more buffer chambers on the one or more substrate regions;
   supplying buffers in the one or more buffer chambers;
   arranging a cathode to place one or more electrode plates of the cathode within the one or more buffer chambers; and
   generating electric fields between the one or more substrate regions and the one or more electrode plates to cause the analytes in the one or more biological samples to migrate toward the capture probes on the substrate, wherein the substrate functions as an anode that is removably coupled to the substrate cassette.

2. The method of claim 1, wherein the capture probes are immobilized on the one or more substrate regions, and
   wherein the one or more biological samples are placed in contact with the capture probes on the one or more substrate regions.

3. The method of claim 1, wherein the one or more substrate regions include one or more wells recessed on the substrate.

4. The method of claim 1,
   wherein the substrate holder comprises a substrate mount for securing the substrate,
   wherein the substrate cassette comprises:
   a gasket including one or more gasket apertures configured to align with the one or more substrate regions when the substrate is secured by the substrate holder, wherein the one or more apertures include the one or more gasket apertures, and wherein the substrate holder comprises:
   one or more holder apertures configured to align with the one or more gasket apertures when the substrate is secured by the substrate holder, wherein the one or more apertures include the one or more gasket apertures and the one or more holder apertures.

5. The method of claim 1, further comprising:
   providing a substrate cover including one or more cover apertures and mounting the cathode; and
   placing the substrate cover onto the substrate cassette such that the one or more cover apertures of the substrate cover are aligned with the one or more apertures of the substrate cassette, respectively, and such that the one or more electrode plates of the cathode extends through the one or more cover apertures into the one or more apertures of the substrate.

6. The method of claim 1, wherein the substrate is coated with a conductive material, and
   wherein the conductive material includes at least one of tin oxide (TO), indium tin oxide (ITO), a transparent conductive oxide (TCO), aluminum doped zinc oxide (AZO), or fluorine doped tin oxide (FTO).

7. The method of claim 1, further comprising:
   arranging one or more spacers between the substrate and the cathode to define the one or more buffer chambers.

8. The method of claim 7, wherein the one or more spacers comprise a non-conductive material.

9. The method of claim 1, wherein said arranging the cathode to place the one or more electrode plates of the cathode within the one or more buffer chambers further comprises at least partially immersing the one or more electrode plates of the cathode in the buffers supplied in the one or more buffer chambers.

10. The method of claim 9, wherein the buffers supplied in the one or more buffer chambers include a permeabilization reagent.

11. The method of claim 1, wherein the buffers supplied in the one or more buffer chambers include at least one of a permeabilization reagent, a permeabilization buffer, a permeabilization enzyme, a buffer without a permeabilization reagent, a permeabilization gel, or a permeabilization solution.

12. The method of claim 1, further comprising:
   providing, from a power supply, a voltage between the substrate and the cathode through electrical wires connecting the power supply to the substrate and the cathode.

13. The method of claim 12, further comprising:
   connecting the electrical wires from the power supply to the substrate and the cathode prior to providing the voltage.

14. The method of claim 1, wherein the one or more biological samples each comprises a cell or a tissue including a cell, and wherein the analytes comprise one of a protein or a nucleic acid.

15. The method of claim 1, wherein the substrate cassette comprises a non-conductive material, and wherein the non-conductive material is one of plastic, glass, porcelain, or rubber.

16. The method of claim 1, further comprising:
   immersing at least a portion of the one or more electrode plates of the cathode in a buffer supplied in the one or more buffer chambers; and
   providing a voltage between the substrate cassette and the one or more electrode plates to generate the electric fields between the one or more substrate regions and the one or more electrode plates.

17. The method of claim 16, wherein the capture probes are immobilized on the one or more substrate regions, and
   wherein the one or more biological samples are placed in contact with the capture probes on the one or more substrate regions.

18. The method of claim 17, wherein the one or more substrate regions include one or more wells recessed on the substrate cassette.

19. The method of claim 16, wherein the substrate cassette is coated with a conductive material, and
   wherein the conductive material includes at least one of tin oxide (TO), indium tin oxide (ITO), a transparent conductive oxide (TCO), aluminum doped zinc oxide (AZO), or fluorine doped tin oxide (FTO).

20. The method of claim 16, wherein the substrate cassette comprises a non-conductive material, and wherein the non-conductive material is one of plastic, glass, porcelain, or rubber.

* * * * *